United States Patent
Chin et al.

(10) Patent No.: US 11,732,001 B2
(45) Date of Patent: Aug. 22, 2023

(54) METHODS OF INCORPORATING AN AMINO ACID COMPRISING A BCN GROUP INTO A POLYPEPTIDE USING AN ORTHOGONAL CODON ENCODING IT AND AN ORTHOGONAL PYLRS SYNTHASE

(71) Applicant: United Kingdom Research and Innovation, Swindon (GB)

(72) Inventors: Jason Chin, Cambridgeshire (GB); Kathrin Lang, Cambridgeshire (GB)

(73) Assignee: United Kingdom Research and Innovation, Swindon (GB)

( * ) Notice: Subject to any disclaimer, the term of this patent is extended or adjusted under 35 U.S.C. 154(b) by 0 days.

(21) Appl. No.: 16/872,826

(22) Filed: May 12, 2020

(65) Prior Publication Data

US 2020/0271658 A1 Aug. 27, 2020

Related U.S. Application Data

(62) Division of application No. 14/401,803, filed as application No. PCT/GB2013/051249 on May 15, 2013, now abandoned.

(30) Foreign Application Priority Data

May 18, 2012 (GB) .................................. 1208875
Jun. 8, 2012 (GB) .................................. 1210303

(51) Int. Cl.
*C07K 1/00* (2006.01)
*G01N 33/58* (2006.01)
(Continued)

(52) U.S. Cl.
CPC ............ *C07K 1/006* (2013.01); *C07C 271/22* (2013.01); *C07K 1/13* (2013.01); *C07K 2/00* (2013.01);
(Continued)

(58) Field of Classification Search
CPC . C07K 1/006; C07K 1/13; C07K 2/00; C12N 9/93; C12Y 601/01026; G01N 33/582; C07C 2602/24; C07C 271/22
See application file for complete search history.

(56) References Cited

U.S. PATENT DOCUMENTS 7,829,659 B2 11/2010 Grabstein et al.
9,868,956 B2 1/2018 Nguyen et al.
(Continued)

FOREIGN PATENT DOCUMENTS

CA 2885796 A1 3/2014
CN 101076598 A 11/2007
(Continued)

OTHER PUBLICATIONS

Lang et al., Genetically encoded norbornene directs site-specific cellular protein labelling via a rapid bioorthogonal reaction, Nat. Chem., vol. 4:298-304 (Published online Feb. 5, 2012) (Year: 2012).*

(Continued)

*Primary Examiner* — Randall L Beane
(74) *Attorney, Agent, or Firm* — Clark & Elbing LLP

(57) ABSTRACT

The invention relates to a polypeptide comprising an amino acid having a bicyclo[6.1.0]non-4-yn-9-ylmethanol (BCN) group, particularly when said BCN group is present as: a residue of a lysine amino acid. The invention also relates to a method of producing a polypeptide comprising a BCN group, said method comprising genetically incorporating an amino acid comprising a BCN group into a polypeptide. The invention also relates to an amino acid comprising bicyclo [6.1.0]non-4-yn-9-ylmethanol (BCN), particularly and amino acid which is bicyclo[6.1.0]non-4-yn-9-ylmethanol (Continued)

(BCN) lysine. In addition the invention relates to a PylRS tRNA synthetase comprising the mutations Y271M, L274G and C313A.

13 Claims, 31 Drawing Sheets
(10 of 31 Drawing Sheet(s) Filed in Color)
Specification includes a Sequence Listing.

(51) Int. Cl.
  C07K 2/00      (2006.01)
  C07C 271/22    (2006.01)
  C07K 1/13      (2006.01)
  C12N 9/00      (2006.01)

(52) U.S. Cl.
  CPC ........ C12N 9/93 (2013.01); C12Y 601/01026 (2013.01); G01N 33/582 (2013.01); C07C 2602/24 (2017.05)

(56) References Cited

U.S. PATENT DOCUMENTS

| | | | |
|---|---|---|---|
| 9,968,690 | B2 | 5/2018 | Chin et al. |
| 10,738,339 | B2 | 8/2020 | Chin et al. |
| 10,774,039 | B2 | 9/2020 | Elliott |
| 2011/0027829 | A1 | 2/2011 | Neumann et al. |
| 2012/0077186 | A1 | 3/2012 | Skach et al. |
| 2012/0077948 | A1 | 3/2012 | Nguyen et al. |
| 2013/0066063 | A1 | 3/2013 | Berry et al. |
| 2013/0137763 | A1 | 5/2013 | Van Delft et al. |
| 2015/0005481 | A1 | 1/2015 | Chin et al. |
| 2015/0148525 | A1 | 5/2015 | Chin et al. |
| 2015/0259721 | A1 | 9/2015 | Grabstein et al. |
| 2017/0015623 | A1 | 1/2017 | Elliot |
| 2017/0356023 | A1 | 12/2017 | Chin et al. |

FOREIGN PATENT DOCUMENTS

| | | |
|---|---|---|
| CN | 104203971 A | 12/2014 |
| CN | 105026574 A | 11/2015 |
| EP | 1911840 A1 | 4/2008 |
| EP | 2192185 A1 | 2/2010 |
| JP | 2007-514447 A | 6/2007 |
| WO | WO 2005/003294 A2 | 1/2005 |
| WO | WO 2006/034332 A2 | 3/2006 |
| WO | WO 2006/110182 A2 | 10/2006 |
| WO | WO 2007/090198 A2 | 8/2007 |
| WO | WO 2008/134761 A2 | 11/2008 |
| WO | WO 2009/056803 A1 | 5/2009 |
| WO | WO 2010/139948 A2 | 12/2010 |
| WO | WO 2011/039518 A2 | 4/2011 |
| WO | WO 2011/039519 A2 | 4/2011 |
| WO | WO 2011/130616 A1 | 10/2011 |
| WO | WO 2011/136645 A1 | 11/2011 |
| WO | WO 2011/156686 A2 | 12/2011 |
| WO | WO 2012/104422 A1 | 8/2012 |
| WO | WO 2012/175924 A2 | 12/2012 |
| WO | WO 2013/108044 A2 | 7/2013 |
| WO | WO 2013/171485 A1 | 11/2013 |
| WO | WO 2014/036492 A1 | 3/2014 |
| WO | WO 2014/044872 A1 | 3/2014 |
| WO | WO 2015/136265 A1 | 9/2015 |
| WO | WO 2016/066995 A1 | 5/2016 |
| WO | WO 2020/084307 A1 | 4/2020 |

OTHER PUBLICATIONS

Chen et al., Clicking 1,2,4,5-tetrazine and cyclooctynes with tunable reaction rates, Chem. Commun,. vol. 48:1736-1738 (online Nov. 24, 2011) (Year: 2011).*

Akey, David L., et al. "Structural basis for macrolactonization by the pikromycin thioesterase" Nature Chemical Biology 2.10 (2006): 537-542.
Berge, Stephen M., et al. "Pharmaceutical salts." Journal of Pharmaceutical Sciences (1977), 66(1), 1-19.
Bruner, Steven D., et al. "Structural basis for the cyclization of the lipopeptide antibiotic surfactin by the thioesterase domain SrfTE." Structure 10.3 (2002): 301-310.
Cravatt, Benjamin F., et al. "Activity-based protein profiling: from enzyme chemistry to proteomic chemistry." Annu. Rev. Biochem. 77 (2008): 383-414.
Di Cera, Enrico. "Serine proteases." IUBMB Life 61.5 (2009): 510-515.
Ekici, Özlem Doğan, et al. "Unconventional serine proteases: variations on the catalytic Ser/His/Asp triad configuration." Protein Science 17.12 (2008): 2023-2037.
Faure, Sophie, et al. "Asymmetric intramolecular [2+2] photocycloadditions: alpha- and beta-hydroxy acids as chiral tether groups". The Journal of Organic Chemistry. 67.4 (2002); 1061-1070.
Frueh, Dominique P., et al. "Dynamic thiolation-thioesterase structure of a non-ribosomal peptide synthetase." Nature 454.7206 (2008): 903-906.
Gehret, Jennifer J., et al. "Terminal alkene formation by the thioesterase of curacin A biosynthesis: structure of a decarboxylating thioesterase." Journal of Biological Chemistry 286.16 (2011): 14445-14454.
Giraldes, John W., et al. "Structural and mechanistic insights into polyketide macrolactonization from polyketide-based affinity labels." Nature Chemical Biology 2.10 (2006): 531-536.
Hay, R. W., et al. "Interaction of DL-2, 3-diaminopropionic acid and its methyl ester with metal ions. Part II. Hydrolysis kinetics." Journal of the Chemical Society, Dalton Transactions 1 (1973): 56-61.
Hedstrom, Lizbeth. "Serine protease mechanism and specificity." Chemical Reviews 102.12 (2002): 4501-4524.
Holliday, Gemma L., et al. "Understanding the functional roles of amino acid residues in enzyme catalysis." Journal of Molecular Biology 390.3 (2009): 560-577.
Hoyer, Katharina M., et al. "The iterative gramicidin s thioesterase catalyzes peptide ligation and cyclization." Chemistry & Biology 14.1 (2007): 13-22.
Koglin, et al., "Facile and Selective Nanoscale Labeling of Peptides in Solution by Using Photolabile Protecting Groups", J. Med. Chem. (2003); 46: 4369-4372.
Korman, Tyler Paz, et al. "Structure and function of an iterative polyketide synthase thioesterase domain catalyzing Claisen cyclization in aflatoxin biosynthesis." Proceedings of the National Academy of Sciences 107.14 (2010): 6246-6251.
Lan, Yun, et al. "Incorporation of 2, 3-diaminopropionic acid in linear cationic amphipathic peptides produces pH sensitive vectors." Chembiochem: a European Journal of Chemical Biology 11.9 (2010): 1266.
Liu, Bin, et al. "Structural analyses on intermediates in serine protease catalysis." Journal of Biological Chemistry 281.33 (2006): 24024-24035.
Liu, Chang C., et al. "Adding new chemistries to the genetic code." Annual Review of Biochemistry 79 (2010): 413-444.
Liu, Ye, Tengfei Zheng, et al. "Structural basis for phosphopantetheinyl carrier domain interactions in the terminal module of nonribosomal peptide synthetases." Chemistry & Biology 18.11 (2011): 1482-1488.
Long, Jonathan Z., et al. "The metabolic serine hydrolases and their functions in mammalian physiology and disease." Chemical Reviews 111.10 (2011): 6022-6063.
Magarvey, Nathan A., et al. "Characterization of the cereulide NRPS α-hydroxy acid specifying modules: activation of α-keto acids and chiral reduction on the assembly line." Journal of the American Chemical Society 128.33 (2006): 10698-10699.
May, Jürgen J., et al. "The dhb operon of bacillus subtilisEncodes the biosynthetic template for the catecholic siderophore 2, 3-dihydroxybenzoate-glycine-threonine trimeric ester bacillibactin." Journal of Biological Chemistry 276.10 (2001): 7209-7217.

(56) References Cited

OTHER PUBLICATIONS

Mayer, Scott C., et al. "Synthesis of new didemnin B analogs for investigations of structure/biological activity relationships." The Journal of Organic Chemistry 59.18 (1994): 5192-5205.
Mcgall, Glenn H., et al. "The efficiency of light-directed synthesis of DNA arrays on glass substrates." Journal of the American Chemical Society 119.22 (1997): 5081-5090.
Morimoto, Jumpei, et al. "Flexizymes: their evolutionary history and the origin of catalytic function." Accounts of Chemical Research, (2011), 44(12), 1359-1368.
Muñiz, A.A.A., "Structural and functional studies of cyclic depsipeptide biosynthesis", Thesis, McGill University, Canada, Apr. 1, 2019 (Apr. 1, 2019), pp. 1-211, XP055662394, Retrieved from the Internet: URL:http://digitool.library.mcgill.ca/R/-?func=dbin-jump-full&current base=GEN01&object_id=168964 [retrieved on Jan. 28, 2020].
Neumann, Heinz, et al. "Genetically encoding N ε-acetyllysine in recombinant proteins." Nature Chemical Biology 4.4 (2008): 232-234.
Nguyen, Duy P., et al. "Genetically encoded 1, 2-aminothiols facilitate rapid and site-specific protein labeling via a bioorthogonal cyanobenzothiazole condensation." Journal of the American Chemical Society 133.30 (2011): 11418-11421.
Otto, Hans-Hartwig, et al. "Cysteine proteases and their inhibitors." Chemical Reviews 97.1 (1997): 133-172.
PCT/GB2019/053023, International Preliminary Report on Patentability dated Apr. 27, 2021, 12 pages.
PCT/GB2019/053023, International Search Report and Written Opinion dated Mar. 31, 2020, 17 pages.
PCT/GB2019/053023, Invitation to pay additional fees, dated Feb. 7, 2020, 13 pages.
Pendrak, Israil, et al. "Synthesis and anti-HSV activity of methylenedioxy mappicine ketone analogs." The Journal of Organic Chemistry 60.9 (1995): 2912-2915.
Phan, Jason, et al. "Structural basis for the substrate specificity of tobacco etch virus protease." Journal of Biological Chemistry 277.52 (2002): 50564-50572.
Radzicka, Anna, et al. "Rates of uncatalyzed peptide bond hydrolysis in neutral solution and the transition state affinities of proteases." Journal of the American Chemical Society 118.26 (1996): 6105-6109.
Robbel, Lars, et al. "TioS T-TE-a prototypical thioesterase responsible for cyclodimerization of the quinoline-and quinoxaline-type class of chromodepsipeptides." The FEBS Journal 276.6 (2009): 1641-1653.
Samel, Stefan A., et al. "The thioesterase domain of the fengycin biosynthesis cluster: a structural base for the macrocyclization of a non-ribosomal lipopeptide." Journal of Molecular Biology 359.4 (2006): 876-889.
Scaglione, Jamie B., et al. "Biochemical and structural characterization of the tautomycetin thioesterase: analysis of a stereoselective polyketide hydrolase." Angewandte Chemie International Edition 49.33 (2010): 5726-5730.
Shaw-Reid, Cathryn A., et al. "Assembly line enzymology by multimodular nonribosomal peptide synthetases: the thioesterase domain of *E. coli* EntF catalyzes both elongation and cyclolactonization." Chemistry & Biology 6.6 (1999): 385-400.
Tanovic, Alan, et al. "Crystal structure of the termination module of a nonribosomal peptide synthetase." Science 321.5889 (2008): 659-663.
Trauger, John W., et al. "Cyclization of backbone-substituted peptides catalyzed by the thioesterase domain from the tyrocidine nonribosomal peptide synthetase." Biochemistry 40.24 (2001): 7092-7098.
Trauger, John W., et al. "Peptide cyclization catalysed by the thioesterase domain of tyrocidine synthetase." Nature 407.6801 (2000): 215-218.
Tsai, Shiou-Chuan, et al. "Crystal structure of the macrocycle-forming thioesterase domain of the erythromycin polyketide synthase: versatility from a unique substrate channel." Proceedings of the National Academy of Sciences 98.26 (2001): 14808-14813.
Tsai, Shiou-Chuan, et al. "Insights into channel architecture and substrate specificity from crystal structures of two macrocycle-forming thioesterases of modular polyketide synthases." Biochemistry 41.42 (2002): 12598-12606.
Tseng, Claire C., et al. "Characterization of the surfactin synthetase C-terminal thioesterase domain as a cyclic depsipeptide synthase." Biochemistry 41.45 (2002): 13350-13359.
Virdee, S., et al. "Semisynthetic Src SH2 domains demonstrate altered phosphopeptide specificity induced by incorporation of unnatural lysine derivatives." Chemistry & Biology. (2010), 17(3), 274-284.
Virdee, Satpal, et al. "Engineered diubiquitin synthesis reveals Lys29-isopeptide specificity of an OTU deubiquitinase." Nature Chemical Biology 6.10 (2010): 750-757.
Whicher, Jonathan R., et al. "Structure and function of the RedJ protein, a thioesterase from the prodiginine biosynthetic pathway in *Streptomyces coelicolor*." Journal of Biological Chemistry 286.25 (2011): 22558-22569.
Yang, Wei, et al. "Understanding the relative acyl-transfer reactivity of oxoesters and thioesters: computational analysis of transition state delocalization effects." Journal of the American Chemical Society 123.44(2001): 11004-11009.
Ambrogelly, et al., "Pyrrolysine is not hardwired for cotranslational insertion at UAG codons," Proc. Natl. Acad. Sci. USA (2007); 104(9): 3141-3146.
Kiick al., "Incorporation of azides into recombinant proteins for chemoselective modification by the Staudinger ligation," Proc. Natl. Acad. Sci. USA (2002); 99(1): 19-24.
Polycarpo, et al., "An aminoacyl-tRNA synthetase that specifically activates pyrrolysine," Proc. Natl. Acad. Sci. USA (2004); 101(34): 12450-12454.
Xie and Schultz, "Adding amino acid to the genetic repertoire", Current Opinion in Chemical Biology (2005); 9: 548-554.
Agard, et al., "A Strain-Promoted [3+2] Azide-Alkyne Cycloaddition for Covalent Modification of Biomolecules in Living Systems". J. Am. Chem. Soc., vol. 126:15046-15047 (Nov. 2, 2004).
Barker, et al., "Tetrazine-Norbornene Click Reactions to Functionalize Degradable Polymers Derived from Lactid Macromol", Rapid Commun. (2011); 32(17), pp. 1362-1366.
Bianco, et al. "Expanding the genetic code of *Drosophila melanogaster*" Nature Chemical Biology (Sep. 2012); 8(9); pp. 748-750.
Blackman, et al. "Tetrazine Ligation: Fast Bioconjugation Based on Inverse-Electron-Demand Diels-Alder Reactivity" J. Am. Chem. Soc., 2008, vol. 130, pp. 13518-13519.
Blight, et al. "Direct charging of tRNAcua with pyrrolysine in vitro and in vivo" Nature, vol. 43, Sep. 16, 2004, pp. 333-335.
Bulygin, et al., "Three distinct peptides from the N domain of translation termination factor eRF1 surround stop codon in the ribosome" RNA (2010), 16:1902-1914.
Canalle, et al., "Clickable Enzyme-linked Immunosorbent Assay". BioMacromolecules (2011); vol. 12: 3692-3697.
Chaen, et al., "Clicking 1,2,4,5-tetrazine and cyclooctynes with tunable reaction rates", Chem. Commun, vol. 48:1736-1738 (online Nov. 24, 2011).
Chin, "Reprogramming the genetic code" EMBO Journal, vol. 30:2312-2324 (2011).
Davis et al., "Designer proteins: applications of genetic code expansion in cell biology", Nature Reviews Molecular Cell Biology, vol. 13:168-182 (Mar. 2012).
Devaraj, et al. "Tetrazine-Based Cycloadditions: Application to Pretargeted Live Cell Imaging" Bioconjugate Chem. (2008); 19(12); pp. 2297-2299.
Dommerholt, et al., "Readily Accessible Bicyclononynes for Bioorthogonal Labeling and Three-Dimensional Imaging of Living Cells", Angew. Chem. Int. Ed., vol. 49:9422-9425 (Dec. 3, 2010).
Fekner, et al., "A Pyrrolysine Analogue for Protein Click Chemistry". Angew Chem Int Ed Engl. (2009); 48(9): 1633-1635.
International Search Report and Written Opinion—International Application No. PCT/GB2015/050694 European Patent Office; dated May 18, 2015; pp. 1-14.
Gaston, et al. "The complete biosynthesis of the genetically encoded amino acid pyrrolysine from lysine" Nature, vol. 471, No. 7340, Mar. 31, 2011, pp. 647-650.

(56) References Cited

OTHER PUBLICATIONS

Hao, et al. A readily synthesized cyclic pyrrolysine analogue for site-specific protein "click labeling" Chem. Commun.(2011); 47: 4502-4504.
Ilegems, Erwin, et al. "Downregulation cif eRFl by RNA interference increases mis-acylated tRNA suppression efficiency in human cells" Protein Engineering, Design & Selection, vol. 17, No. 12, pp. 821-827, 2004.
International Search Report and Written Opinion in International Application No. PCT/GB2013/051249, dated Oct. 14, 2013, 15 pages.
International Search Report and Written Opinion in International Application No. PCT/GB2010/001083, dated Mar. 28, 2011, 16 pages.
International Search Report and Written Opinion in International Application No. PCT/GB2015/053141 dated Feb. 2, 2016, 12 pages.
International Search Report and Written Opinion in International Application No. PCT/GB2015/050694, dated May 22, 2015, 12 pages.
International Search Report and Written Opinion for International Application No. PCT/GB2013/050121 dated Oct. 9, 2013, 20 pages.
International Preliminary Report on Patentability in International Application No. PCT/GB2015/053141 dated Feb. 3, 2017, 17 pages.
International Preliminary Report on Patentability in International Application No. PCT/GB2015/050694, dated Sep. 14, 2016, 8 pages.
International Preliminary Report on Patentability in International Application No. PCT/GB2013/051249, dated Nov. 18, 2014, 9 pages.
International Preliminary Report on Patentability in International Application No. PCT/GB2010/001083, dated Dec. 6, 2011, 9 pages.
International Preliminary Report on Patentability for International Application No. PCT/GB2013/050121 dated Jul. 22, 2014, 11 pages.
Koglin, et al., "Facile and Selective Nanoscale Labeling of Peptides in Solution by Using Photolabile Protecting Groups", J. Med. Chem., vol. 46:4369-4372 (2003).
Kolosov, et al., "Invariant amino acids essential for decoding function of polypeptide release factor eRF1", Nucleic Acids Research (2005); vol. 33, No. 19; p. 6418-6425.
Krzycki, et al. "The direct genetic encoding of pyrrolysine", Current Opinion in Microbiology, Current Biology Ltd, GB., vol. 8, No. 6, Dec. 1, 2005, pp. 706-712.
Lang, K., et al. "Genetically encoded norbornene directs site-specific protein labelling via a rapid bioorthogonal reaction" Nature Chemistry (Apr. 2012); vol. 4; pp. 298-304.
Lekomtsev, S., et al., "Different modes of stop codon restriction by the Stylonychia and Paramecium eRF1 translation termination factors" PNAS (2007); vol. 104, No. 26; pp. 10824-10829.
Li, et al., "A Pyrrolysine Analogue for Site-Specific Protein Ubiquitination". Angew Chem Int Ed Engl. (2009); 48(48): 9184-9187.
Malito, et al., "Crystal structure of a Baeyer-Villiger monooxygenase", PNAS, vol. 101 (36): 13157-13162 (Sep. 7, 2004) (Year: 2004).
Meeuwissen, et al., "Cofactor regeneration in polymersome nanoreactors: enzymatically catalysed Baeyer-Villiger reactions". J. Mater. Chem. (2011); vol. 21:18923-18926 and pp. 1-14 of Supplemental Information (Sep. 12, 2011).
Mukai, et al., "Adding L-lysine derivatives to the genetic code of mammalian cells with engineered pyrrolysyl-tRNA synthetases", Biochemical and Biophysical Research Communications (Jul. 11, 2008); vol. 371, Issue 4, pp. 818-822.
Nuemann, et al., "Genetically encoding N(epsilon)-acetyllysine in recombinant proteins", Nat Chem Biol. (Apr. 2008); 4(4): 232-234.
Nguyen, et al., "Genetic Encoding and Labeling of Aliphatic Azides and Alkynes in Recombinant Proteins via a Pyrrolysyl-tRNA Synthetase/ tRNACUA Pair and Click Chemistry". J Am Chem Soc. (Jul. 1, 2009); 131(25): 8720-8721.

Nozawa, et al., "Pyrrolysyl-tRNA synthetase:tRNAPyl structure reveals the molecular basis of orthogonality". Nature (Feb. 26, 2009); 457(7233): 1163-1167.
Prescher and Bertozzi, "Chemistry in living systems", Nature Chemical Biology (2005); vol. 1, No. 1, pp. 13-21.
Seit-Nebi, Alim, et al. "Conversion of omnipotent translation termination factor eRF1 into ciliate-like UGA-only unipotent eRF1" European Molecular Biology Organization, vol. 3, No. 9; pp. 881-886, 2002.
Sletten and Bertozzi, "Bioorthogonal Chemistry: Fishing for Selectivity in a Sea of Functionality" Angew. Chem. Int. Ed. (2009); 48(38), pp. 6974-6998.
Strable, et al., "Unnatural Amino Acid Incorporation into Virus-Like Particles". Bioconjug Chem. (Apr. 2008); 19(4): 866-875. Epub Mar. 5, 2008.
[Author Unknown] ThermoFisher Scientific, Amine-Reactive Crosslinker Chemistry, Thermo Fisher Scientific, ThermoFisher. com, attached as pdf, 8 pages (Apr. 18, 2012). (cited in U.S. Appl. No. 14/401,803 by the Examiner as having a published date of Apr. 18, 2012).
Virdee, et al. "Traceless and Site-Specific Ubiquitination of Recombinant Proteins" J. Am. Chem. Soc., 2011, vol. 133, pp. 10708-10711.
Yanagisawa, et al., "Multistep engineering of pyrrolysyl-tRNA synthetase to genetically encode N(epsilon)-(oazidobenzyloxycarbonyl)lysine for site-specific protein modification", Chem & Biol. (Nov. 24, 2008); 15(11): 1187-1197.
Yang et al., "Live-Cell Imaging of Cyclopropene Tags with Fluorogenic Tetrazine Cycloadditions", Angew Chem Int Ed Engl. (Jul. 23, 2012); 51(30): 7476-7479.
Zeglis, et al., "Modular Strategy for the Construction of Radiometalated Antibodies for Positron Emission Tomography Based on Inverse Electron Demand Diels-Alder Click Chemistry" Bioconjugate Chem. (2011); 22(10), pp. 2048-2059.
Zhang, "Synthesis of Cyclopropene r-Amino Acids via Enantioselective Desymmetrization", Organic Letters (2006); vol. 8, No. 14, pp. 2965-2968.
Aggarwal, Anup, et al. "Development of a novel lead that targets M. tuberculosis polyketide synthase 13." Cell 170.2 (Jul. 13, 2017): 249-259.
Alonzo, Diego A., et al. "Characterization of cereulide synthetase, a toxin-producing macromolecular machine." PLoS ONE 10.6 (Jun. 4, 2015): e0128569, 19pgs.
Argyropoulos, Panos, et al. "Towards a characterization of the structural determinants of specificity in the macrocyclizing thioesterase for deoxyerythronolide B biosynthesis." Biochimica et Biophysica Acta (BBA)-General Subjects 1860.3 (Mar. 1, 2016): 486-497.
Baker, Austin S., et al. "Optical control of protein function through unnatural amino acid mutagenesis and other optogenetic approaches." ACS Chemical Biology 9.7 (May 12, 2014): 1398-1407.
Cappadocia, Laurent, et al. "Ubiquitin-like protein conjugation: structures, chemistry, and mechanism." Chemical Reviews 118.3 (Feb. 24, 2018): 889-918.
Chin, Jason W. "Expanding and reprogramming the genetic code of cells and animals." Annual Review of Biochemistry 83 (Jun. 2, 2014): 379-408.
Cleary, Jennifer A., et al. "Quantifying tetrahedral adduct formation and stabilization in the cysteine and the serine proteases." Biochimica et Biophysica Acta (BBA)-Proteins and Proteomics 1854.10 (Oct. 1, 2015): 1382-1391.
Drake, Eric J., et al. "Structures of two distinct conformations of holo-non-ribosomal peptide synthetases." Nature 529.7585 (Jan. 14, 2016): 235-238.
Elliott, Thomas et al. "Proteome labeling and protein identification in specific tissues and at specific developmental stages in an animal" Nature Biotechnology (May 2014), vol. 32, No. 5, pp. 465-472. Epub Apr. 13, 2014.
Gavalda, Sabine, et al. "The polyketide synthase Pks13 catalyzes a novel mechanism of lipid transfer in mycobacteria." Chemistry & Biology 21.12 (Dec. 18, 2014): 1660-1669.

(56) References Cited

OTHER PUBLICATIONS

Guntaka, Naga Sandhya, et al. "Structure and functional analysis of ClbQ, an unusual intermediate-releasing thioesterase from the colibactin biosynthetic pathway." ACS Chemical Biology 12.10 (Oct. 20, 2017): 2598-2608.
Horsman, Mark E., et al. "Polyketide synthase and non-ribosomal peptide synthetase thioesterase selectivity: logic gate or a victim of fate?." Natural Product Reports 33.2 (Feb. 2016): 183-202. First Published Feb. 2, 2015.
Huguenin-Dezol, et al., "Trapping biosynthetic acyl-enzyme intermediates with encoded 2, 3-diaminopropionic acid". Nature (Jan. 1, 2019); 565(7737): 112-117.
Jaitzig, Jennifer, et al. "Reconstituted biosynthesis of the nonribosomal macrolactone antibiotic valinomycin in *Escherichia coli*." ACS Synthetic Biology 3.7 (Dec. 11, 2014): 432-438.
Kaya, et al. "A Genetically Encoded Norbornene Amino Acid for the Mild and Selective Modification of Proteins in a Copper-Free Click Reaction" Angew. Chem. Int. Ed. (Mar. 21, 2012); 571(18): 4466-4469.
Koglin, et al., "Structural basis for the selectivity of the external thioesterase of the surfactin synthetase". Nature (Aug. 14, 2008); 454(7206): 907-111.
Kryuchkova, P., "Two-step model of stop codon recognition by eukaryotic release factor eRF1", Nucleic Acids Research (Feb. 22, 2013); vol. 41, No. 8, pp. 4573-4586.
Lang, K., et al. "Genetic Encoding of Bicyclononynes and trans-Cyclooctenes for Site-Specific Protein Labeling in Vitro and in Live Mammalian Cells via Rapid Fluorogenic Diels-Alder Reactions" J. Am. Chem. Soc. (Jun. 13, 2012); 134, pp. 10317-10320.
Li, Jie, et al. "Palladium-triggered deprotection chemistry for protein activation in living cells." Nature Chemistry 6.4 (Apr. 2014): 352-361. Epub Mar. 16, 2014.
Ngo, Phong D., et al. "Serine protease catalysis: a computational study of tetrahedral intermediates and inhibitory adducts." The Journal of Physical Chemistry B 120.30 (Jul. 7, 2016): 7353-7359.
Nguyen, Duy P., et al. "Genetic encoding of photocaged cysteine allows photoactivation of TEV protease in live mammalian cells." Journal of the American Chemical Society, (Jan. 30, 2014); 136(6): 2240-2243.
Patterson, David M., et al., "Functionalized cyclopropenes as bioorthogonal chemical reporters." Journal of the American Chemical Society (Oct. 16, 2012); 134.45: 18638-18643.
Plass, et al., "Amino Acids for Diels-Alder Reactions in Living Cells" Angew. Chem. Int. Ed. (Mar. 30, 2012); 51(17): 4166-4170. Epub Mar. 30, 2012.
Plechanovova, Anna, et al. "Structure of a Ring E3 ligase and ubiquitin-loaded E2 primed for catalysis." Nature 489.7414 (Sep. 6, 2012): 115-120.
Rogerson, Daniel T., et al. "Efficient genetic encoding of phosphoserine and its nonhydrolyzable analog." Nature Chemical Biology 11.7 (Jul. 2015): 496-503. Epub Jun. 1, 2015.
Sachdeva, Amit, et al. "Concerted, Rapid, Quantitative, and Site-Specific Dual Labeling of Proteins" Journal of the American Chemical Society (May 23, 2014); 136: 7785-7788.
Schmied, Wolfgang H., et al. "Efficient Multisite Unnatural Amino Acid Incorporation in Mammalian Cells via Optimized Pyrrolysyl tRNA Synthetase/tRNA Expression and Engineered eRF1" Journal of the American Chemical Society (Oct. 28, 2014); 136: 15577-15583.
Swatek, Kirby N., et al. "Ubiquitin modifications." Cell Research 26.4 (Mar. 25, 2016): 399-422.
Verma, Sonia, et al. "Cysteine proteases: modes of activation and future prospects as pharmacological targets." Frontiers in Pharmacology 7 (Apr. 25, 2016): 107, 12 pages.
Yu and Lin, "Design of Spiro[2.3]hex-1-ene, a Genetically Encodable Double-Strained Alkene for Superfast Photoclick Chemistry" Journal of American Chemical Society (Mar. 4, 2014), 136, pp. 4153-4156, S1-S82.
Yu, Zhipeng, et al. "Genetically Encoded Cyclopropene Directs Rapid, Photoclick-Chemistry-Mediated Protein Labeling in Mammalian Cells" Angew. Chem. Int. Ed. (Sep. 20, 2012), 51, pp. 10600-10604.
Zhang, Michael Shaofei, et al. "Biosynthesis and genetic encoding of phosphothreonine through parallel selection and deep sequencing." Nature Methods 14.7 (May 29, 2017): 729-736.
Zhou, Yongjun, et al. "Iterative mechanism of macrodiolide formation in the anticancer compound conglobatin." Chemistry & Biology 22.6 (Jun. 18, 2015): 745-754.
Zhou, Yongjun, et al. "Macrodiolide formation by the thioesterase of a modular polyketide synthase." Angewandte Chemie 127.17 (Mar. 6, 2015): 5321-5324.
Huguenin-Dezot et al., "Trapping biosynthetic acyl-enzyme intermediates with encoded 2,3-diaminopropionic acid," available in PMC Jun. 20, 2019, published in final edited form as: Nature. 565(7737):112-117 (2019) (30 pages).

* cited by examiner

Figure 1
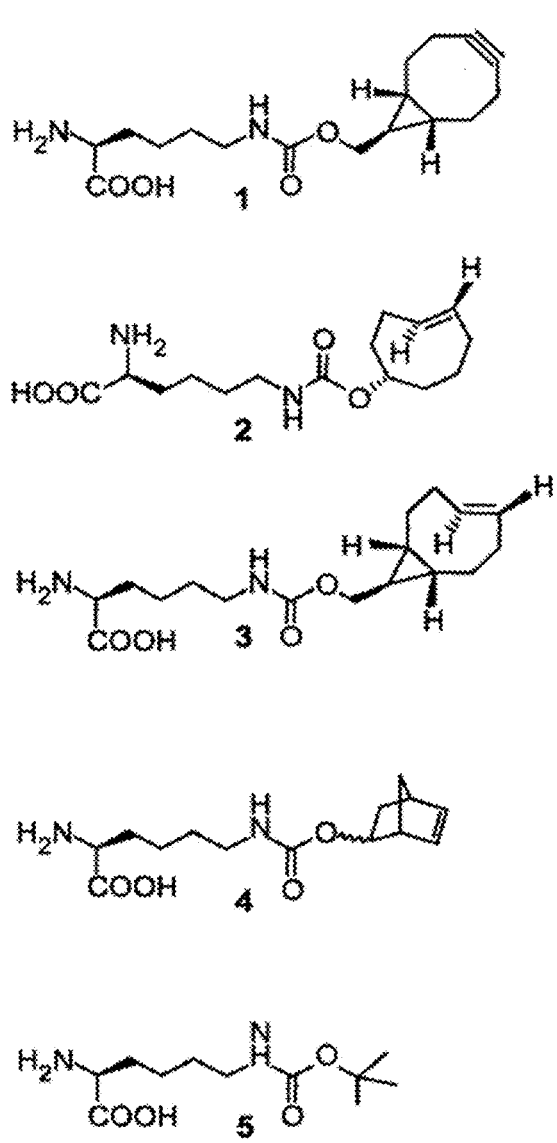
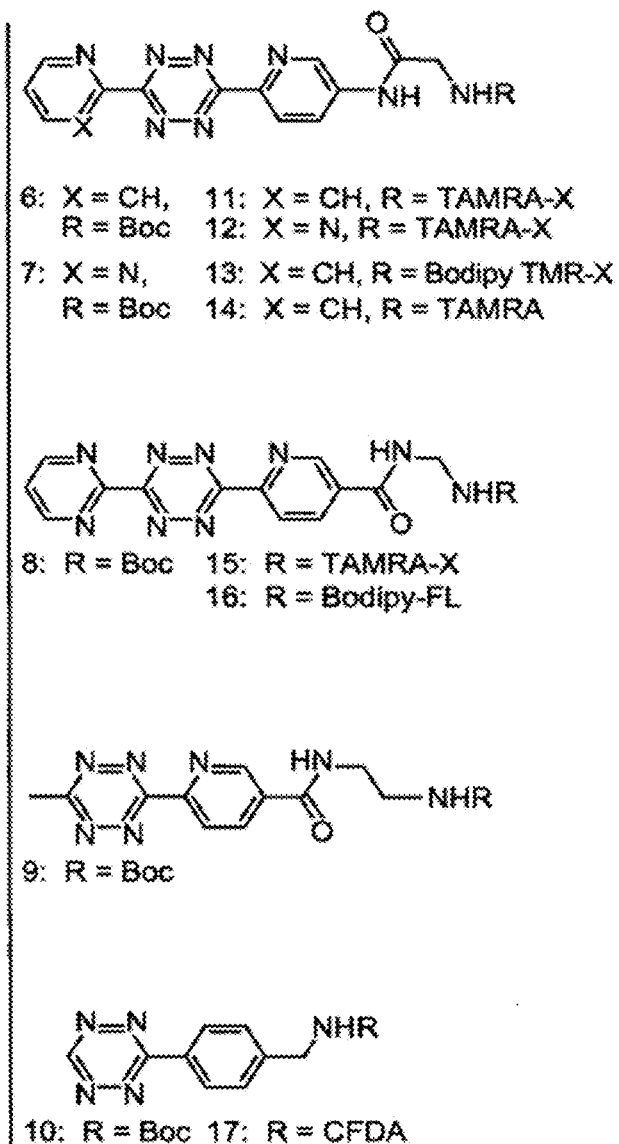

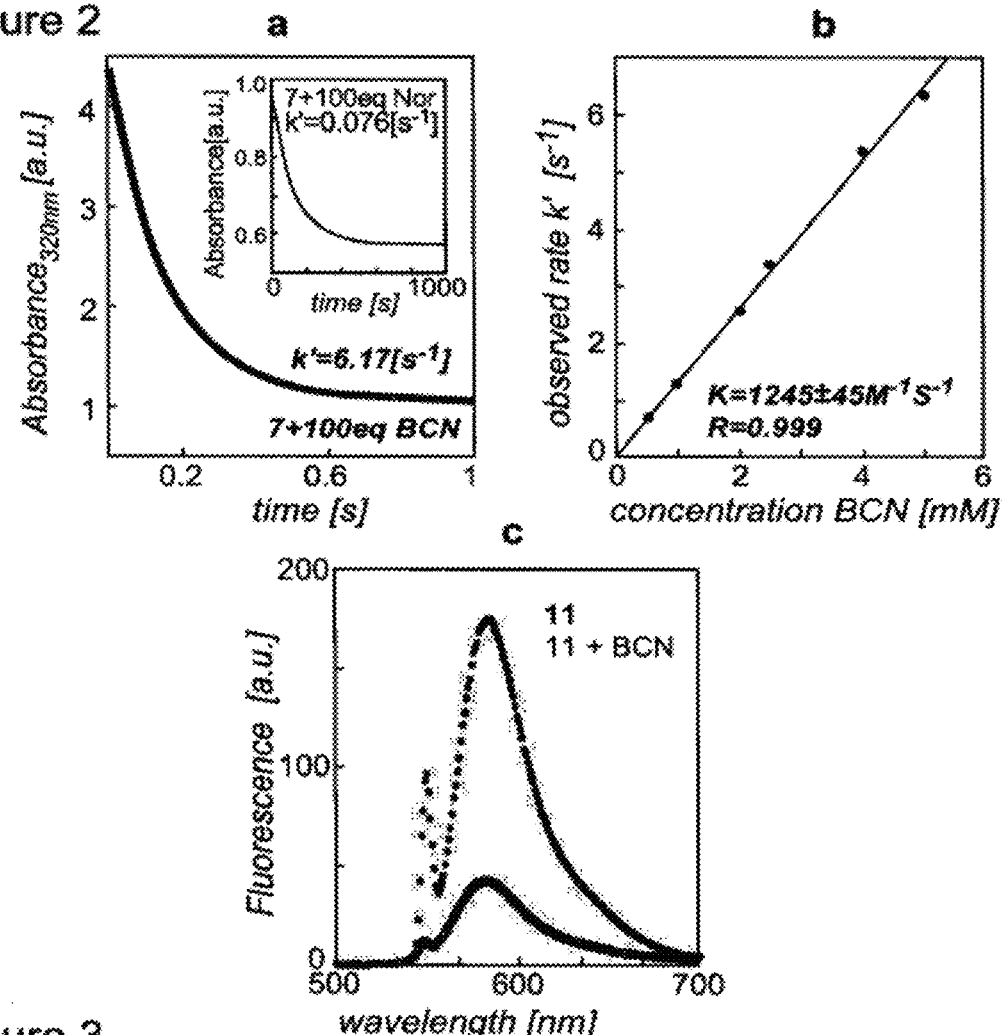
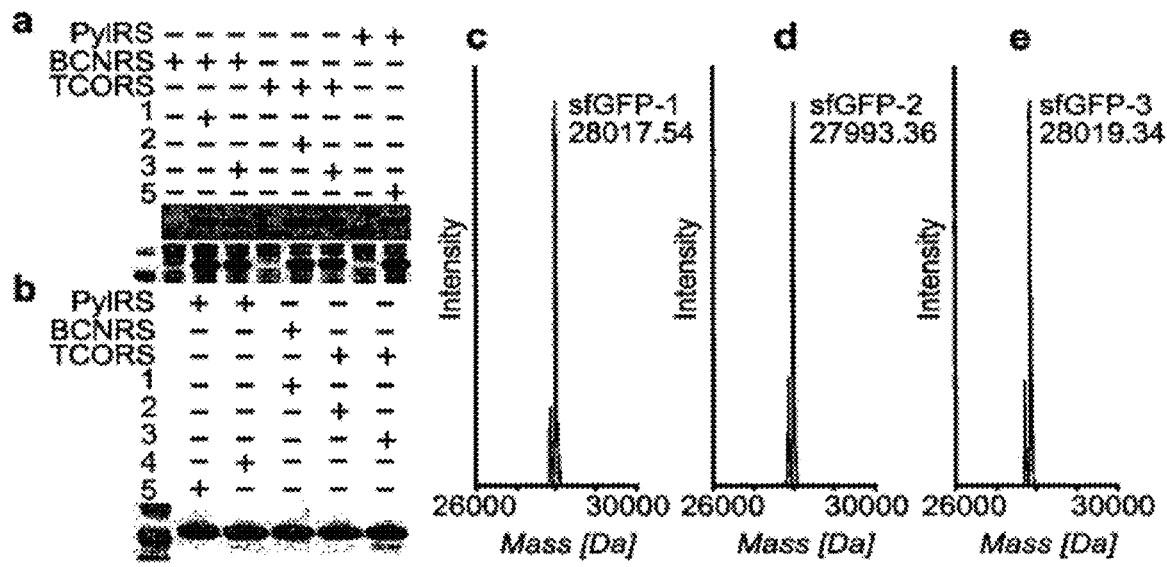

Figure 4
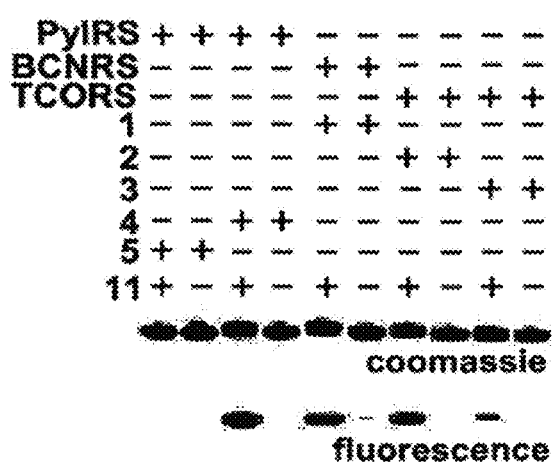
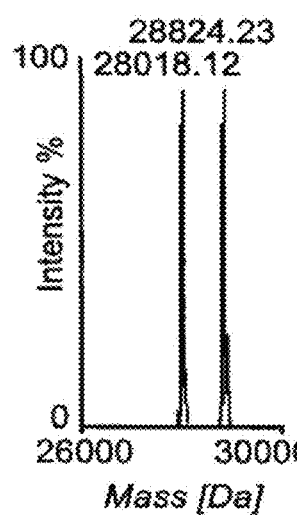 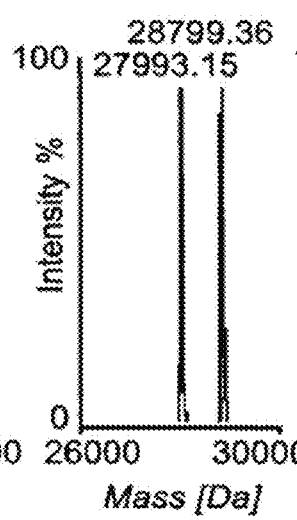 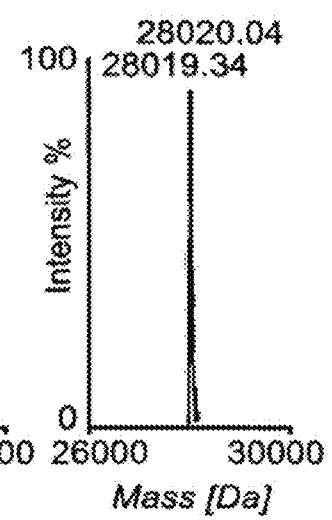
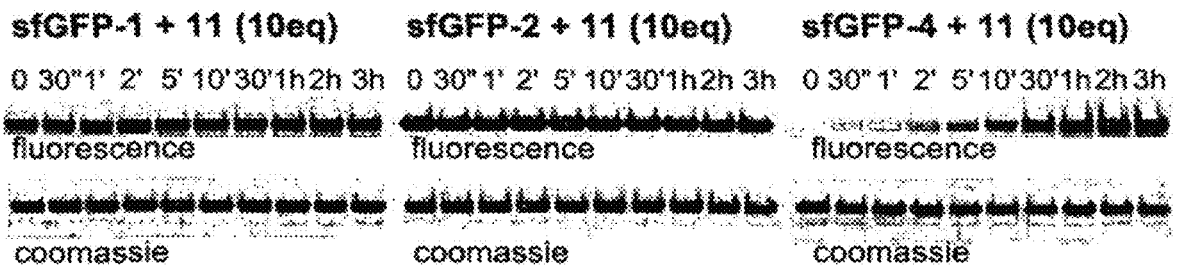

Figure 5
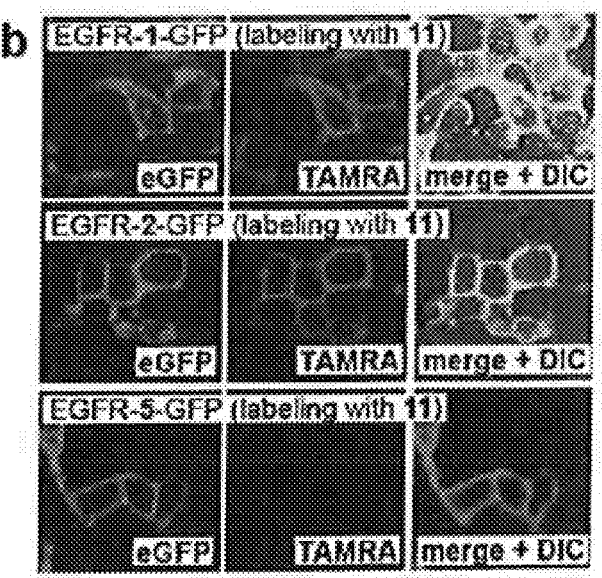
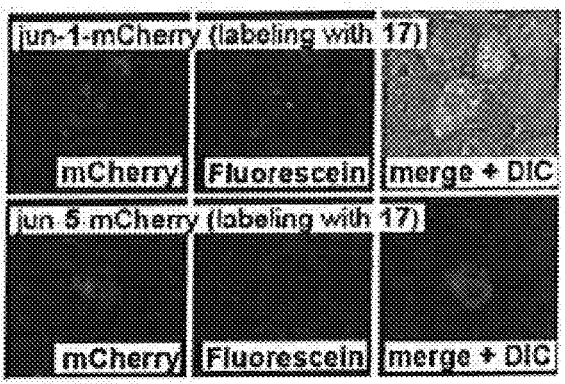

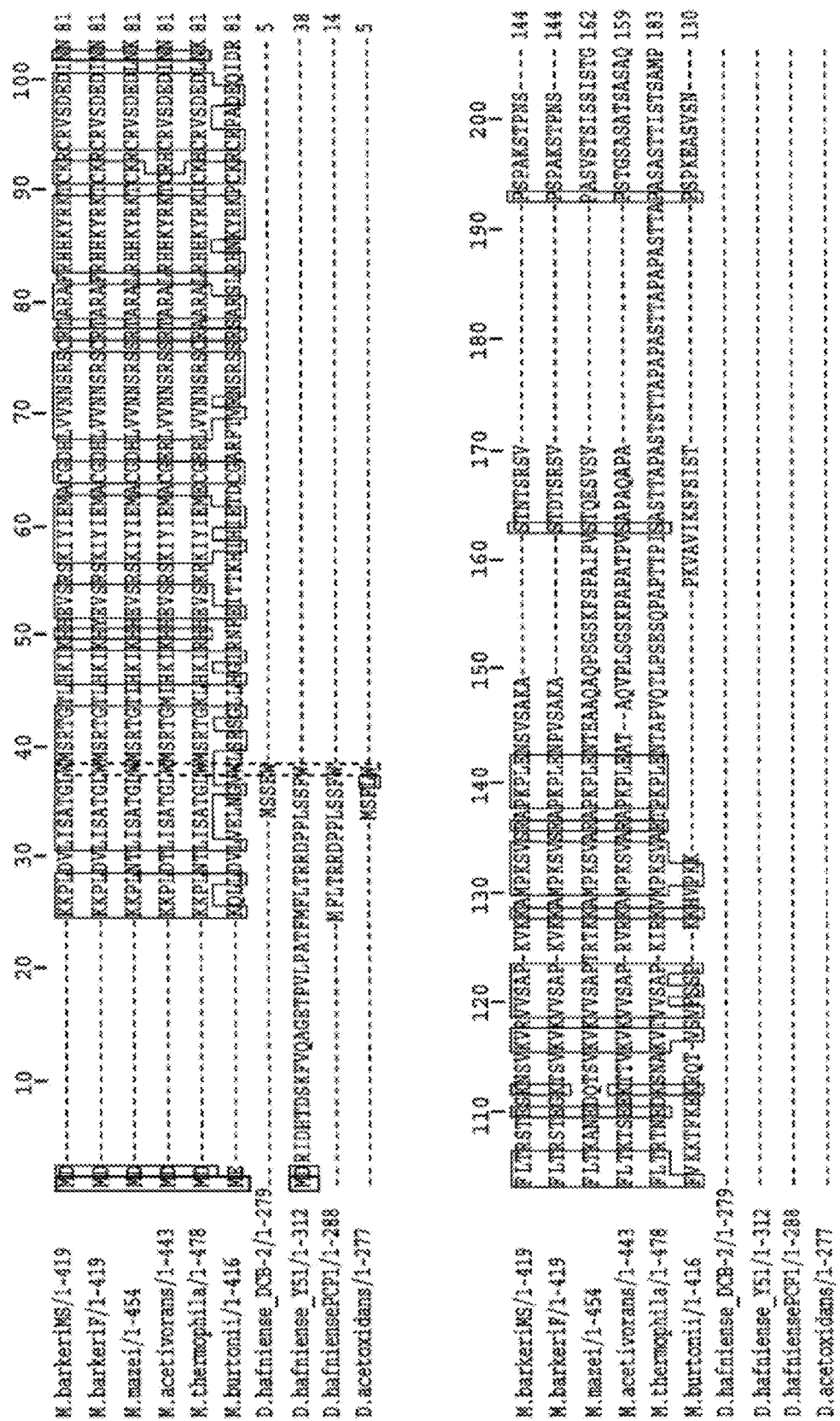
Figure 6 Alignment of PylS sequences

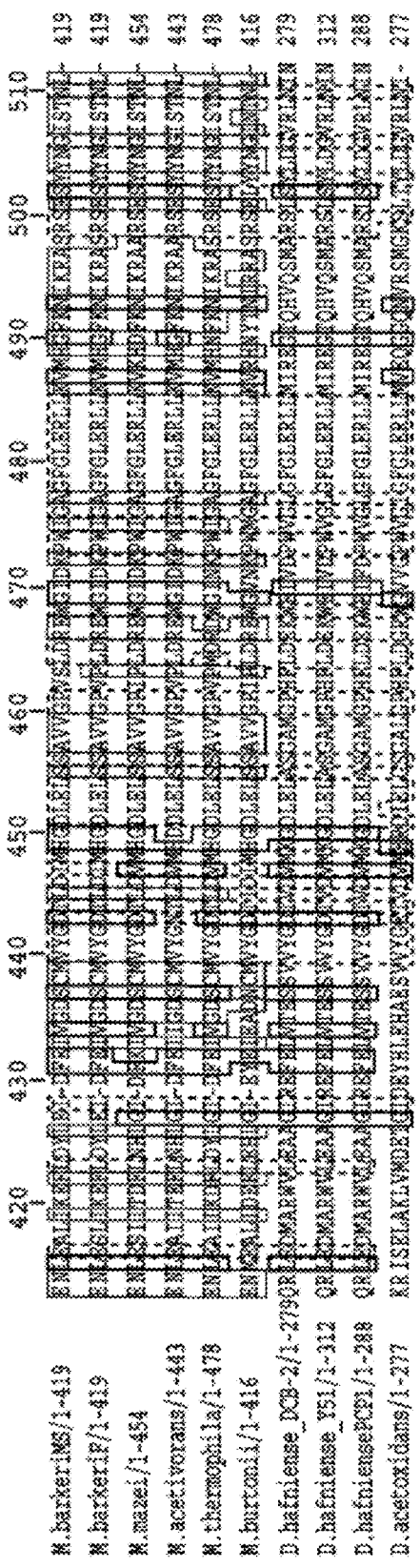
Figure 6 (Continued)
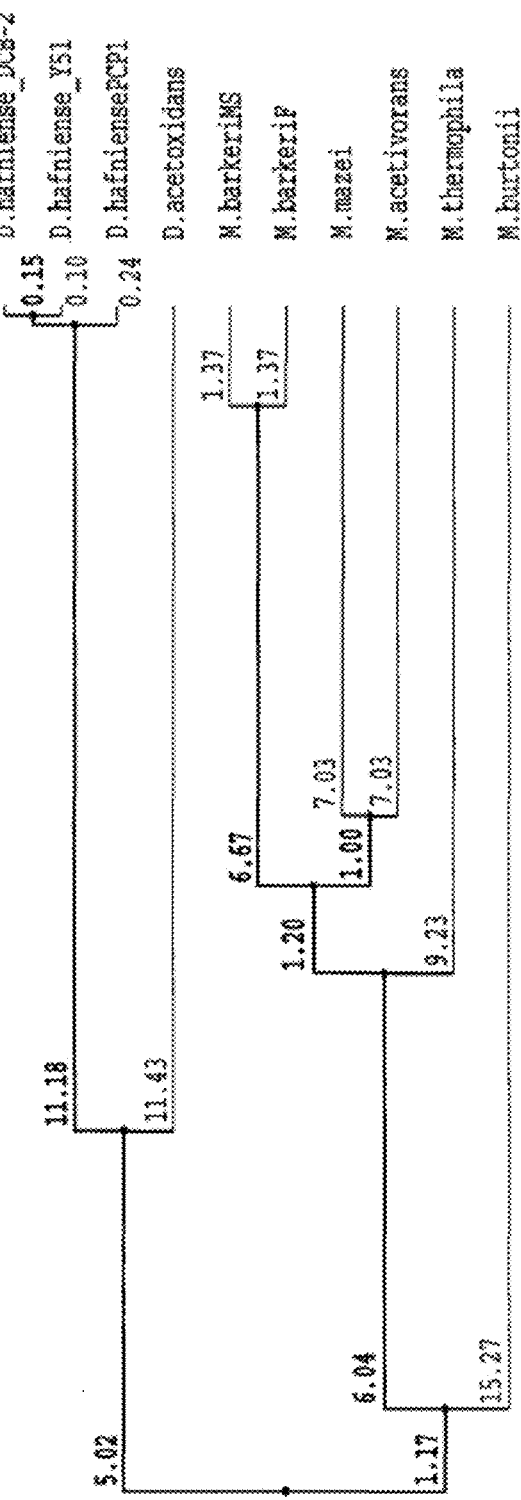
Figure 7 Sequence identity of PylS sequences Figure 8 Alignment of the catalytic domain of PylS sequences (from 350 to 480; numbering from alignment of figure 6)

Figure 9 Sequence identity of the catalytic domains of PylS sequences

Figure 10 Alignment of synthetases with transplanted mutations based on M.barkeri PylS or M.mazei PylS

Figure 10 (Continued)

| | 270 | 280 | 290 | 300 | 310 | 320 | |
|---|---|---|---|---|---|---|---|
| Mb_PylS/1-419 | EIKSPILIPA | EYVEYMGIDNDTELSKQIFRVDKNL | CLRPMLAPTLYNYLR | KLDRILPGPIKIFEV | 290 |
| Mb_AcKRS/1-419 | EIKSPILIPA | EYVEFMGIDNDTELSKQIFRVDKNL | CLRPMLAPTIFNYAR | KLDRILPGPIKIFEV | 290 |
| Mb_PCKRS/1-419 | EIKSPILIPA | EYVERFGIDNDTELSKQIFRVDKNL | CLRPMVAPNLCNYAR | KLDRILPGPIKIFEV | 290 |
| Mm_PylS/1-454 | EIKSPILIPL | EYIERMGIDKDTELSKQIFRVDKNF | CLRPMLAPNLYNYLR | KLDRALPDPIKIFEI | 325 |
| Mm_AcKRS/1-454 | EIKSPILIPL | EYIERMGIDKDTELSKQIFRVDKNF | CLRPMVAPNIFNYAR | KLDRALPDPIKIFEI | 325 |
| Mm_PCKRS/1-454 | EIKSPILIPL | EYIERFGIDKDTELSKQIFRVDKNF | CLRPMLLSNMLCNYMR | KLDRALPDPIKIFEI | 325 |

| | 330 | 340 | 350 | 360 | 370 | 380 | |
|---|---|---|---|---|---|---|---|
| Mb_PylS/1-419 | GPCYRKESDGKEHLEEFTMVN | FCQMGSGCTRENLEALIKEFLD | YLREDLEILKV | 355 |
| Mb_AcKRS/1-419 | GPCYRKESDGKEHLEEFTMVN | FCQMGSGCTRENLEALIKEFLD | YLREDLEILKV | 355 |
| Mb_PCKRS/1-419 | GPCYRKESDGKEHLEEFTMVN | FCQMGSGCTRENLEALIKEFLD | YLREDLEILKV | 355 |
| Mm_PylS/1-454 | GPCYRKESDGKEHLEEFTMLN | FCQMGSGCTRENLESIITDFLN | HLGIDFKIVGDSCMVYGDTLDV | 390 |
| Mm_AcKRS/1-454 | GPCYRKESDGKEHLEEFTMLN | FCQMGSGCTRENLESIITDFLN | HLGIDFKIVGDSCMVYGDTLDI | 390 |
| Mm_PCKRS/1-454 | GPCYRKESDGKEHLEEFTMLN | FCQMGSGCTRENLESIITDFLN | HLGIDFKIVGDSCMVYGDTLDI | 390 |

| | 400 | 410 | 420 | 430 | 440 | 450 | |
|---|---|---|---|---|---|---|---|
| Mb_PylS/1-419 | MHGDLELSSAVVGPIPLDREWGIDKPWIGAGFGLERLLKVMHGFKNIKRAS | RSESYYNGISTNL | 419 |
| Mb_AcKRS/1-419 | MHGDLELSSAVVGPIPLDREWGIDKPWIGAGFGLERLLKVMHGFKNIKRAA | RSESYYNGISTNL | 419 |
| Mb_PCKRS/1-419 | MHGDLELSSAVVGPIPLDREWGIDKPWIGAGFGLERLLKVMHGFKNIKRAA | RSESYYNGISTNL | 419 |
| Mm_PylS/1-454 | MHGDLELSSAVVGPIPLDREWGIDKPWIGAGFGLERLLKVKHDFKNIKRAA | RSESYYNGISTNL | 454 |
| Mm_AcKRS/1-454 | MHGDLELSSAVVGPIPLDREWGIDKPWIGAGFGLERLLKVKHDFKNIKRAA | RSESYYNGISTNL | 454 |
| Mm_PCKRS/1-454 | MHGDLELSSAVVGPIPLDREWGIDKPWIGAGFGLERLLKVKHDFKNIKRAA | RSESYYNGISTNL | 454 |

Figure 11
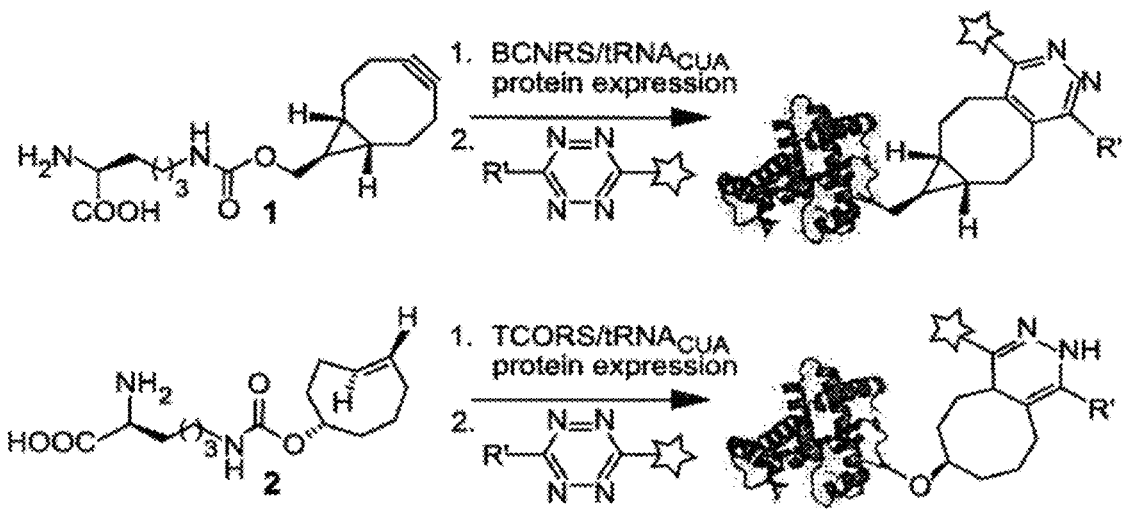
Figure 12 (Supplementary Figure S1)
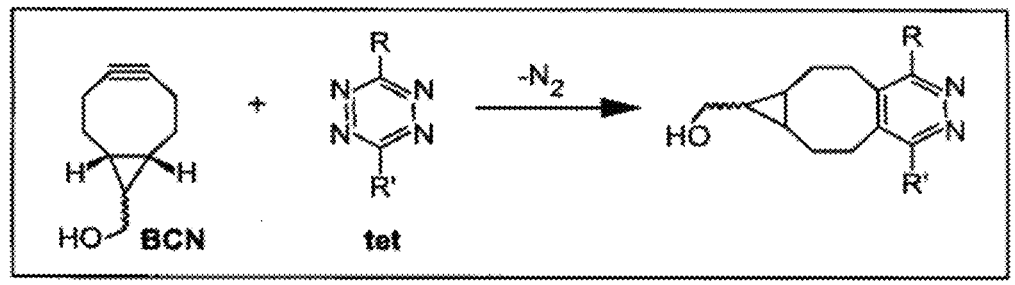
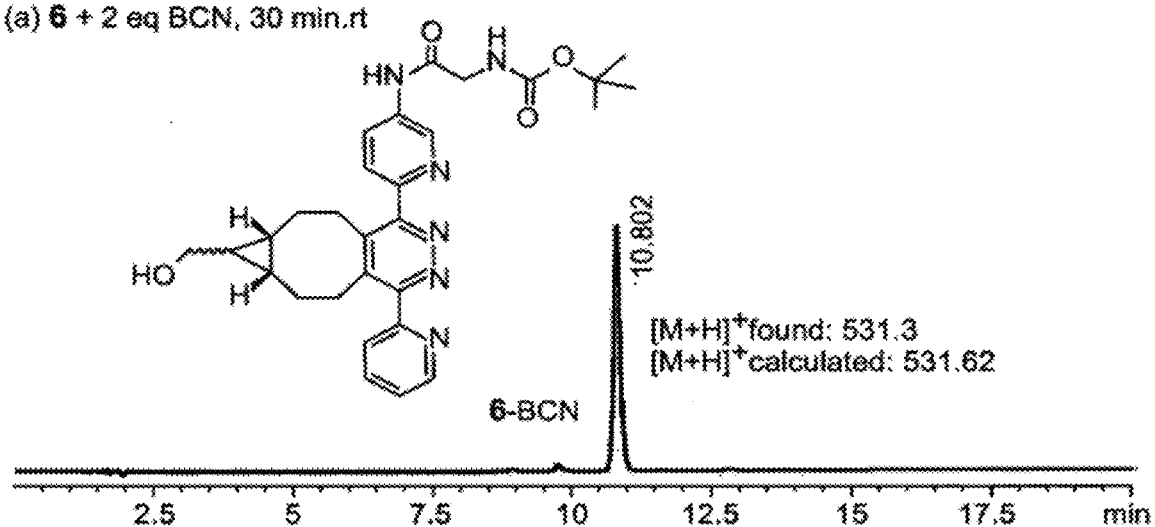

Figure 12 (Supplementary Figure S1) continued
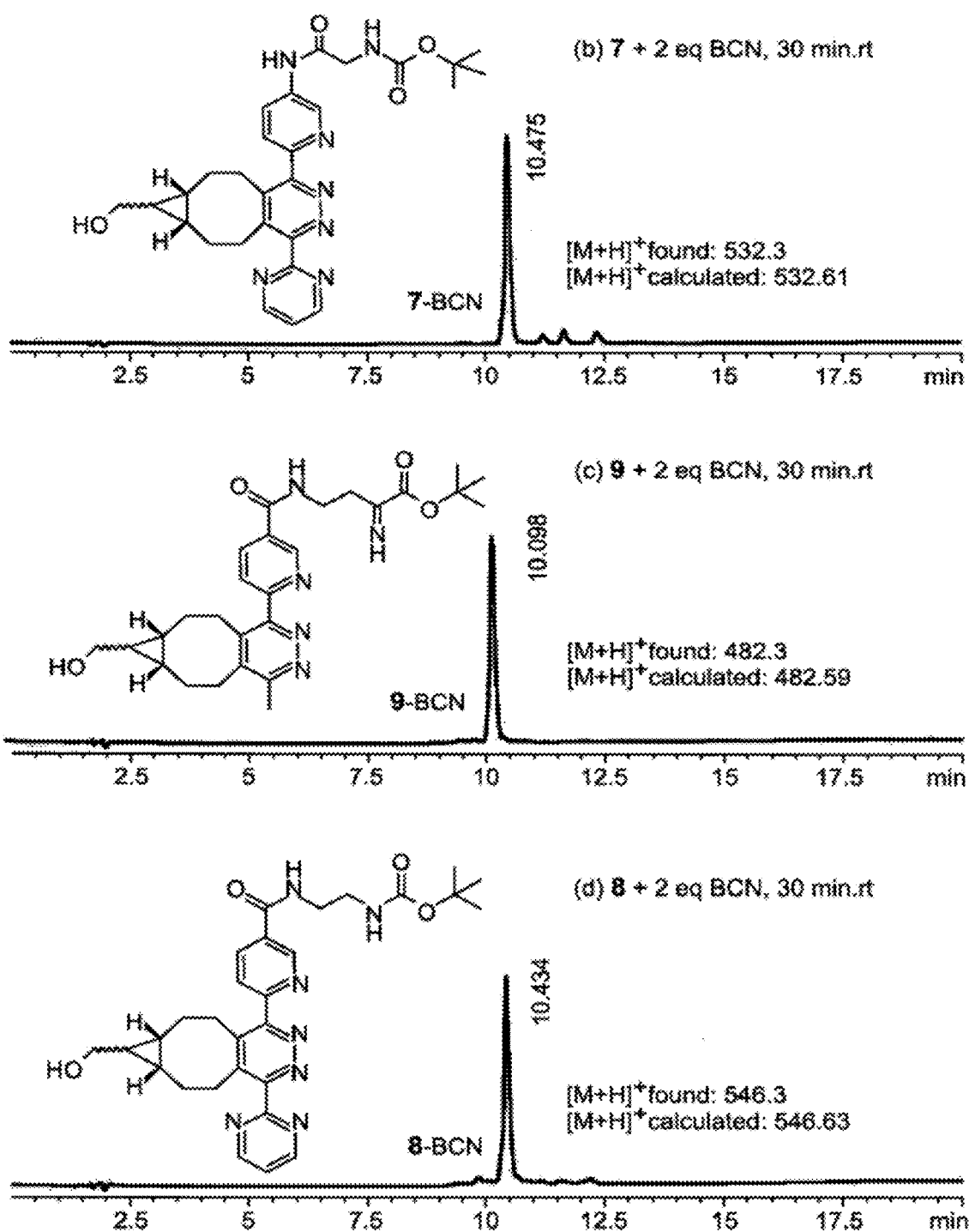

Figure 13 (Supplementary Figure S2)
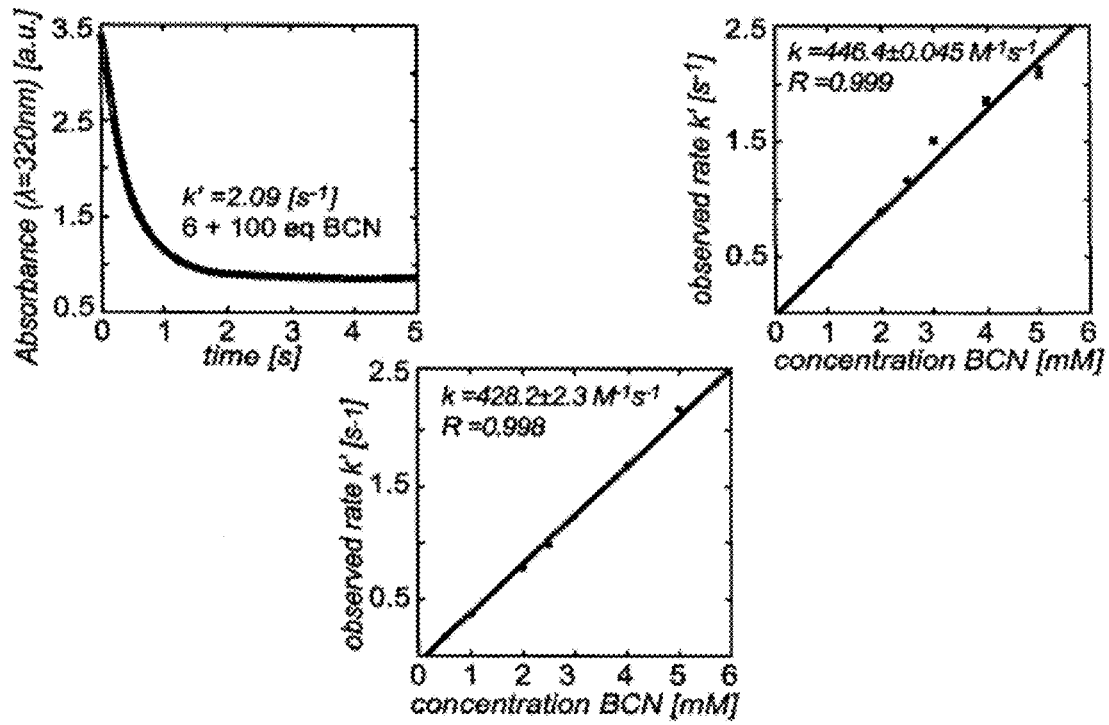
(a) 6 plus BCN in 55/45 MeOH/H$_2$O, 25°C
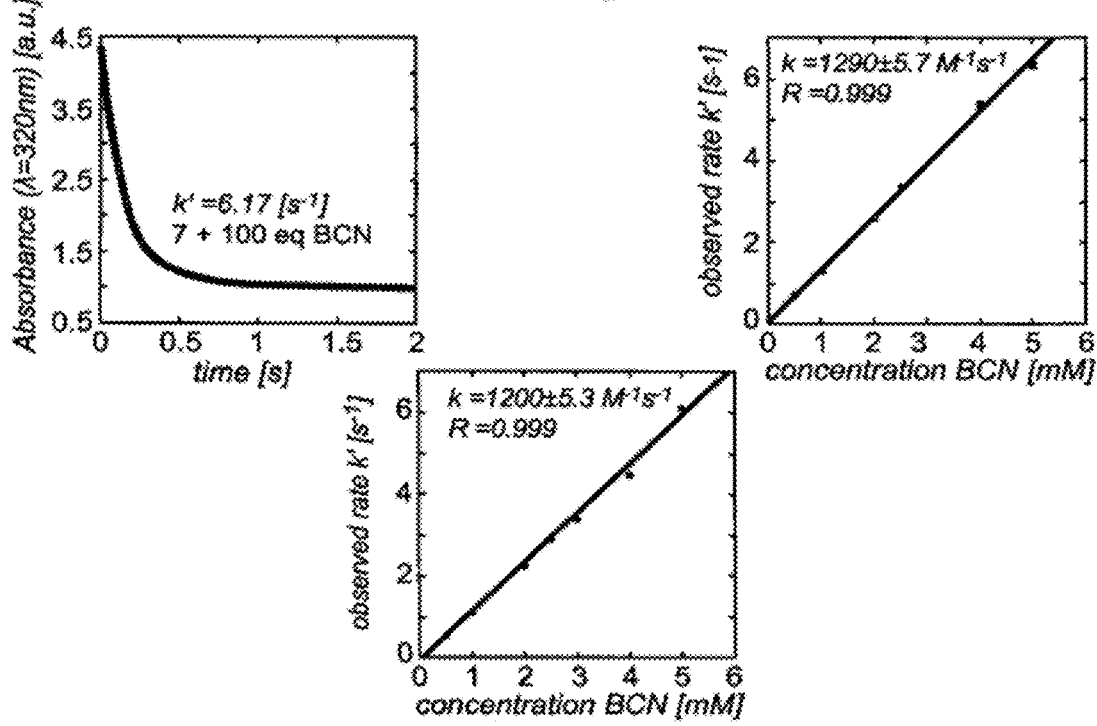
(b) 7 plus BCN in 55/45 MeOH/H$_2$O, 25°C Figure 13 (Supplementary Figure S2) continued
(c) 9 plus BCN in 55/45 MeOH/H$_2$O, 25°C
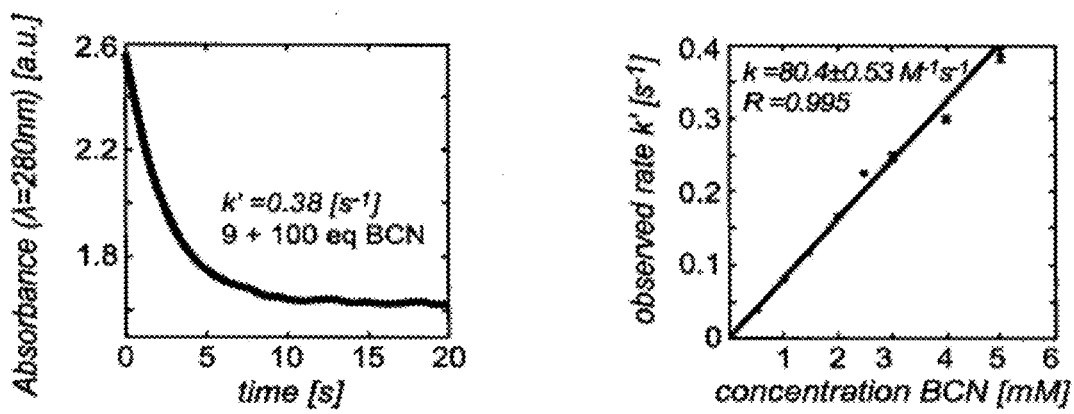
(d) 8 plus BCN in 55/45 MeOH/H$_2$O, 25°C
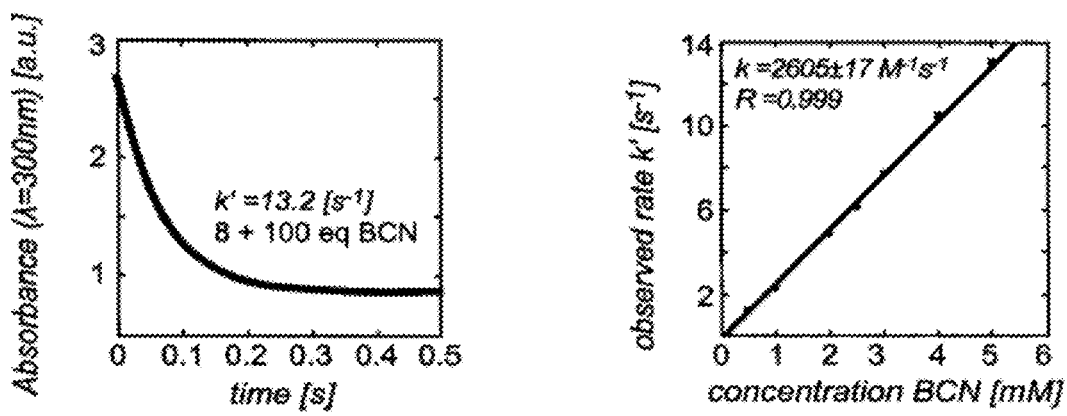
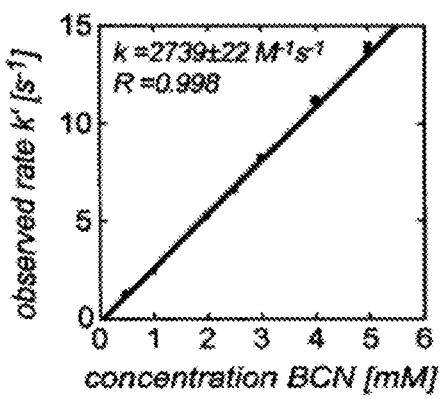

Figure 14
(Supplementary Figure S3)
(a) 6 plus TCO in 55/45 MeOH/H$_2$O, 25°C
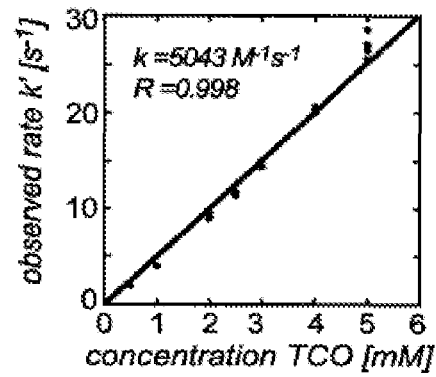
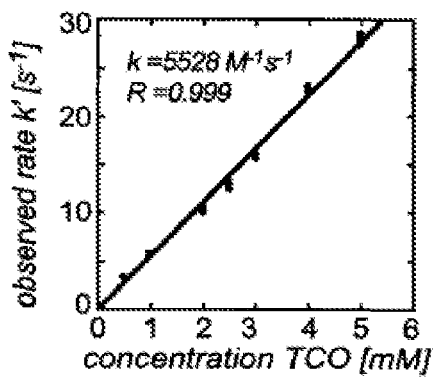
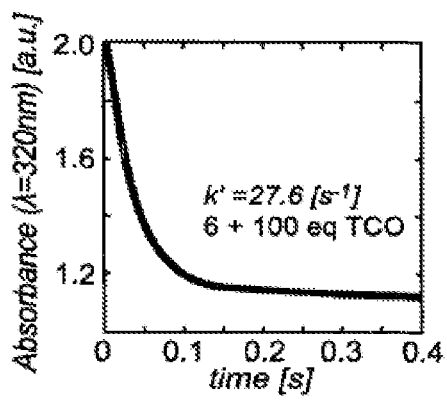
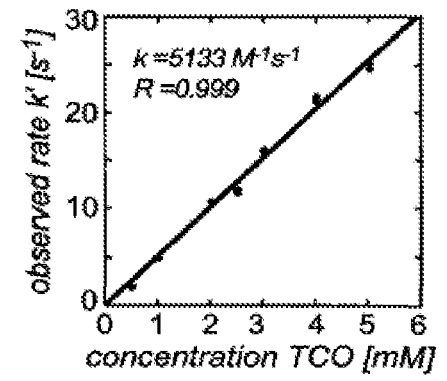
(b) 7 plus TCO in 55/45 MeOH/H$_2$O, 25°C
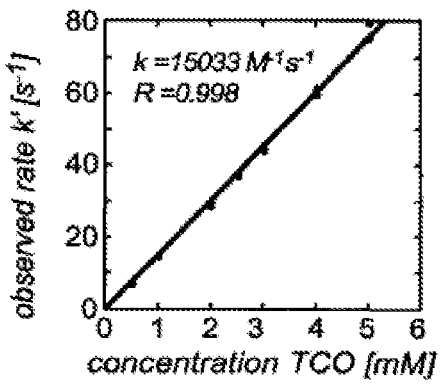
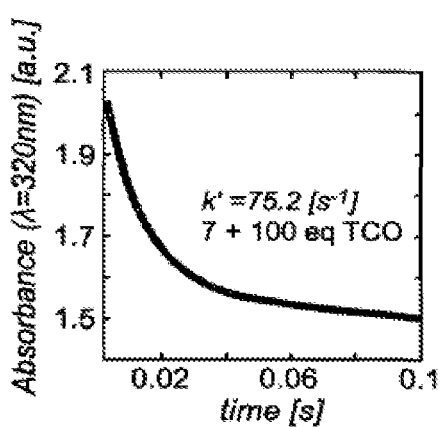
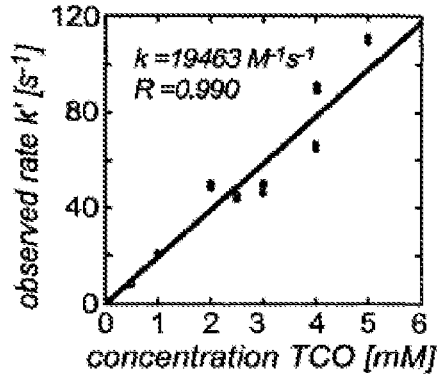

Figure 14 (Supplementary Figure S3) continued
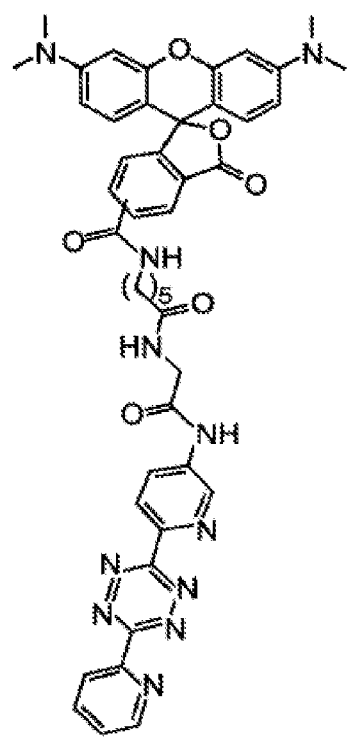
11 (6-TAMRA-X)
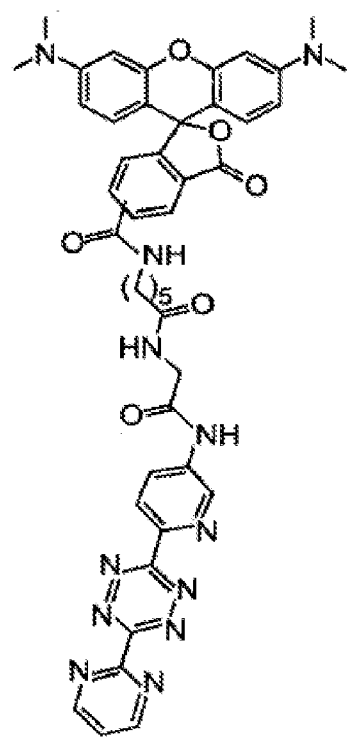
12 (7-TAMRA-X)
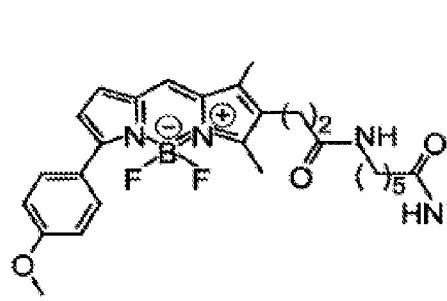
13 (6-BODIPY TMR-X)
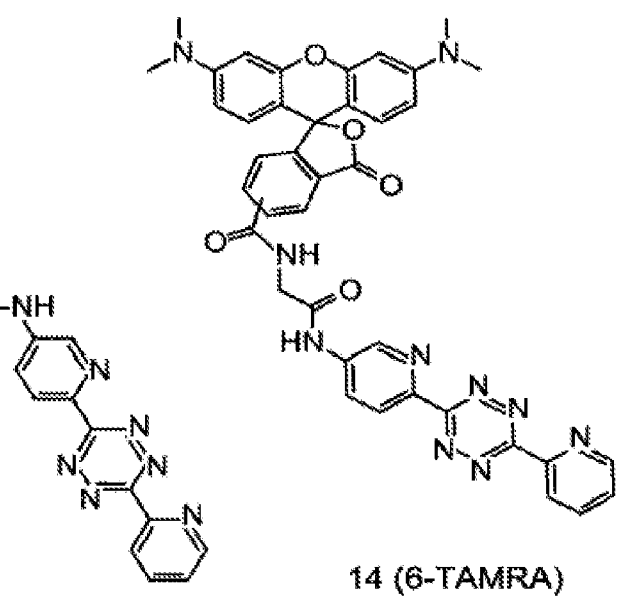
14 (6-TAMRA)

Figure 15 (Supplementary Figure S4)
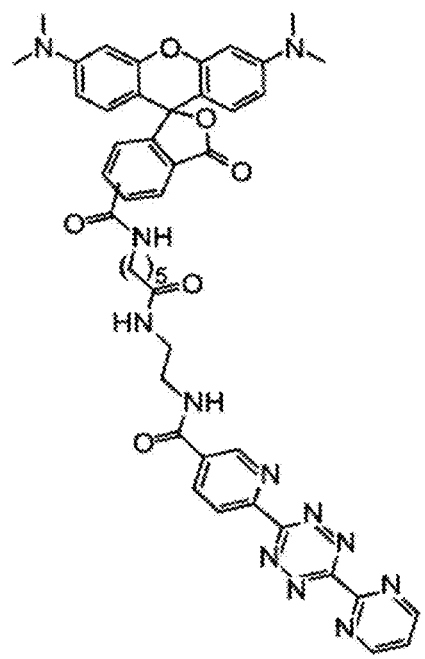
15 (8-TAMRA-X)
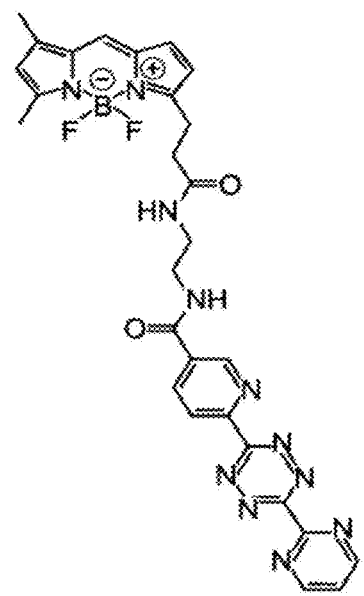
16 (8-Bodipy-FL)
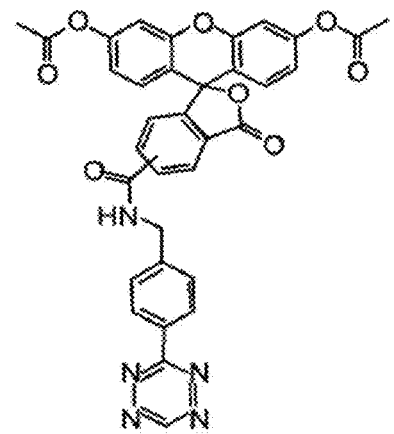
17 (10-CFDA)

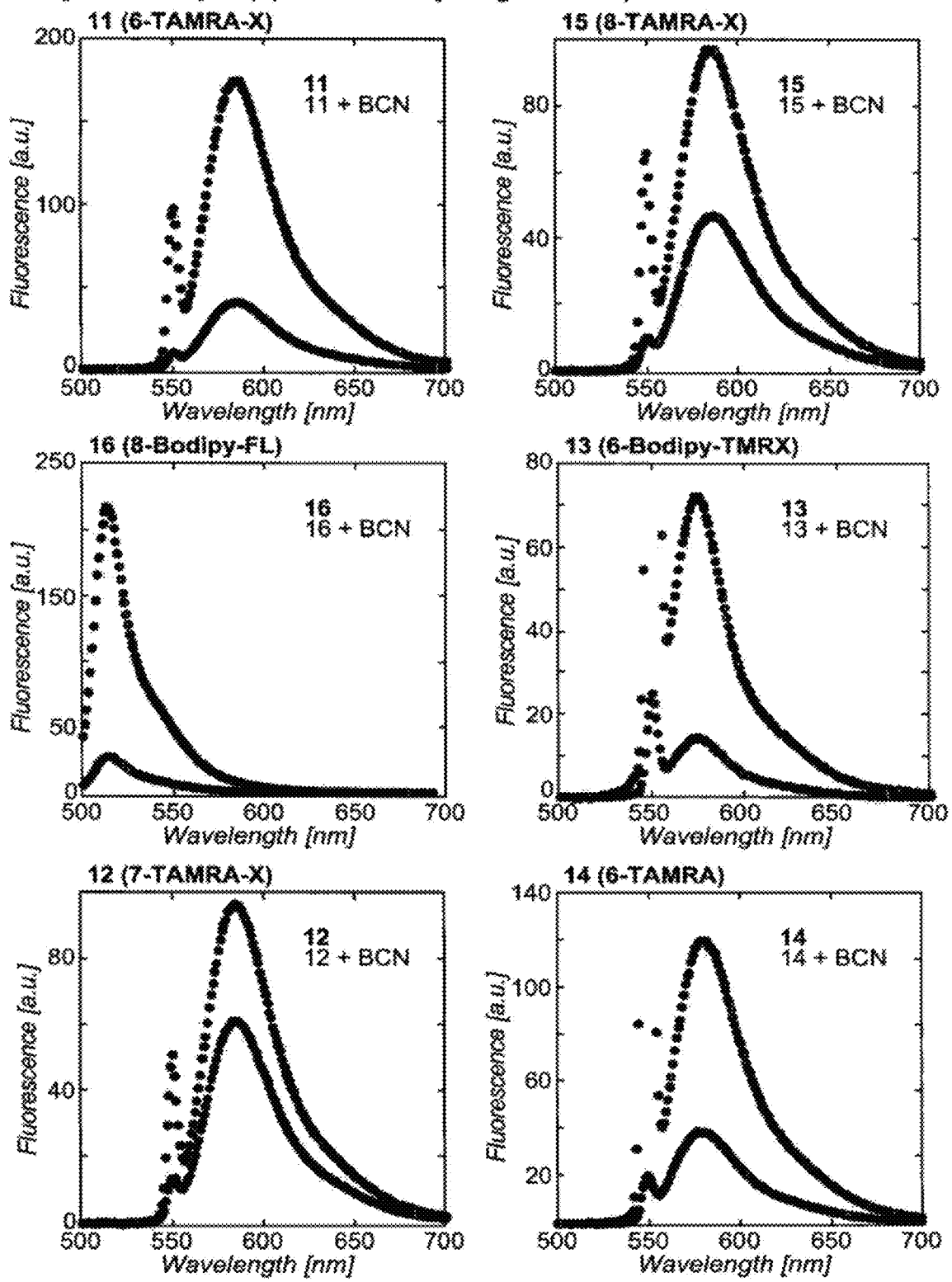
Figure 16 (Supplementary Figure S5)

Figure 17 (Supplementary Figure S6)
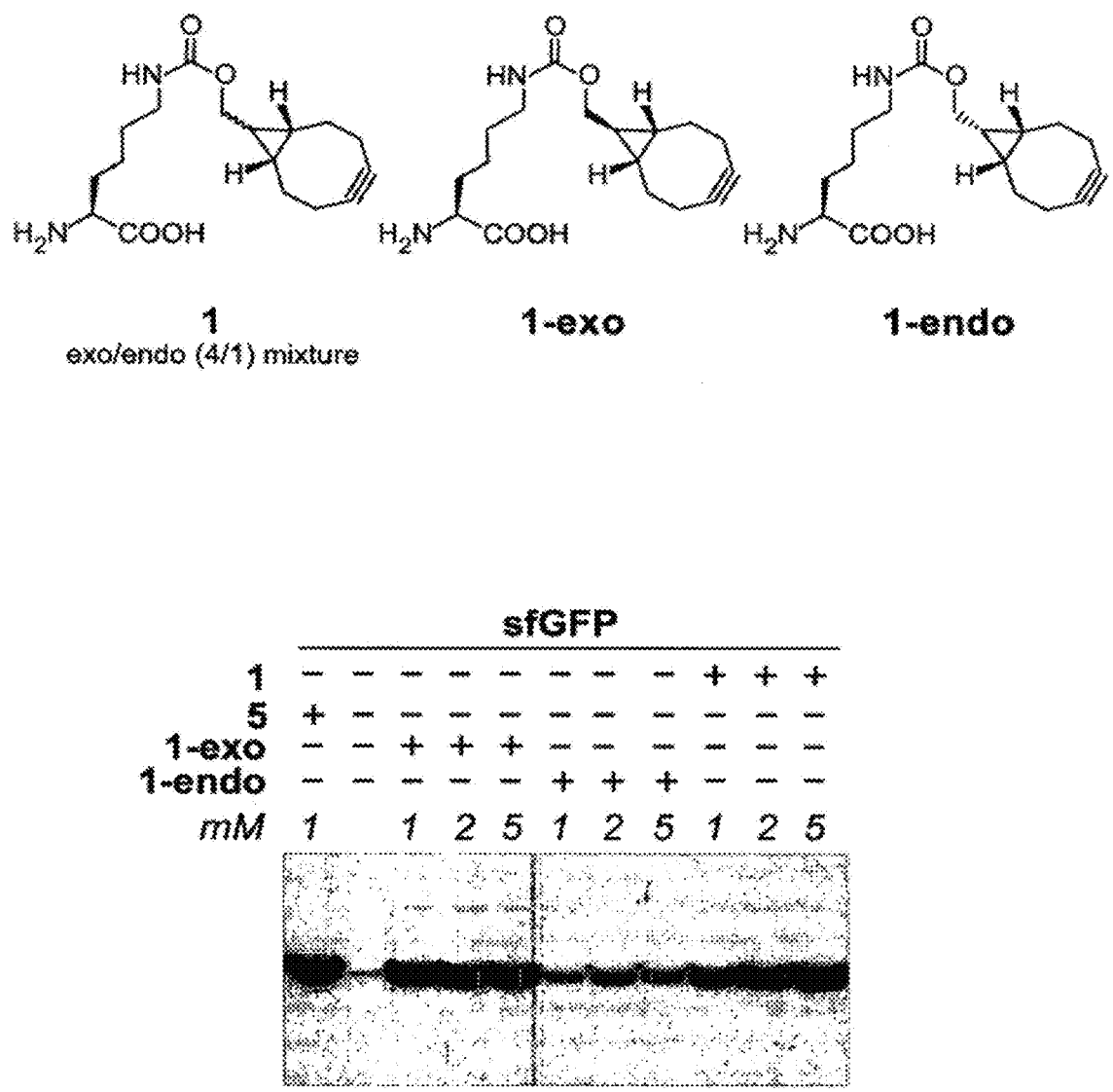

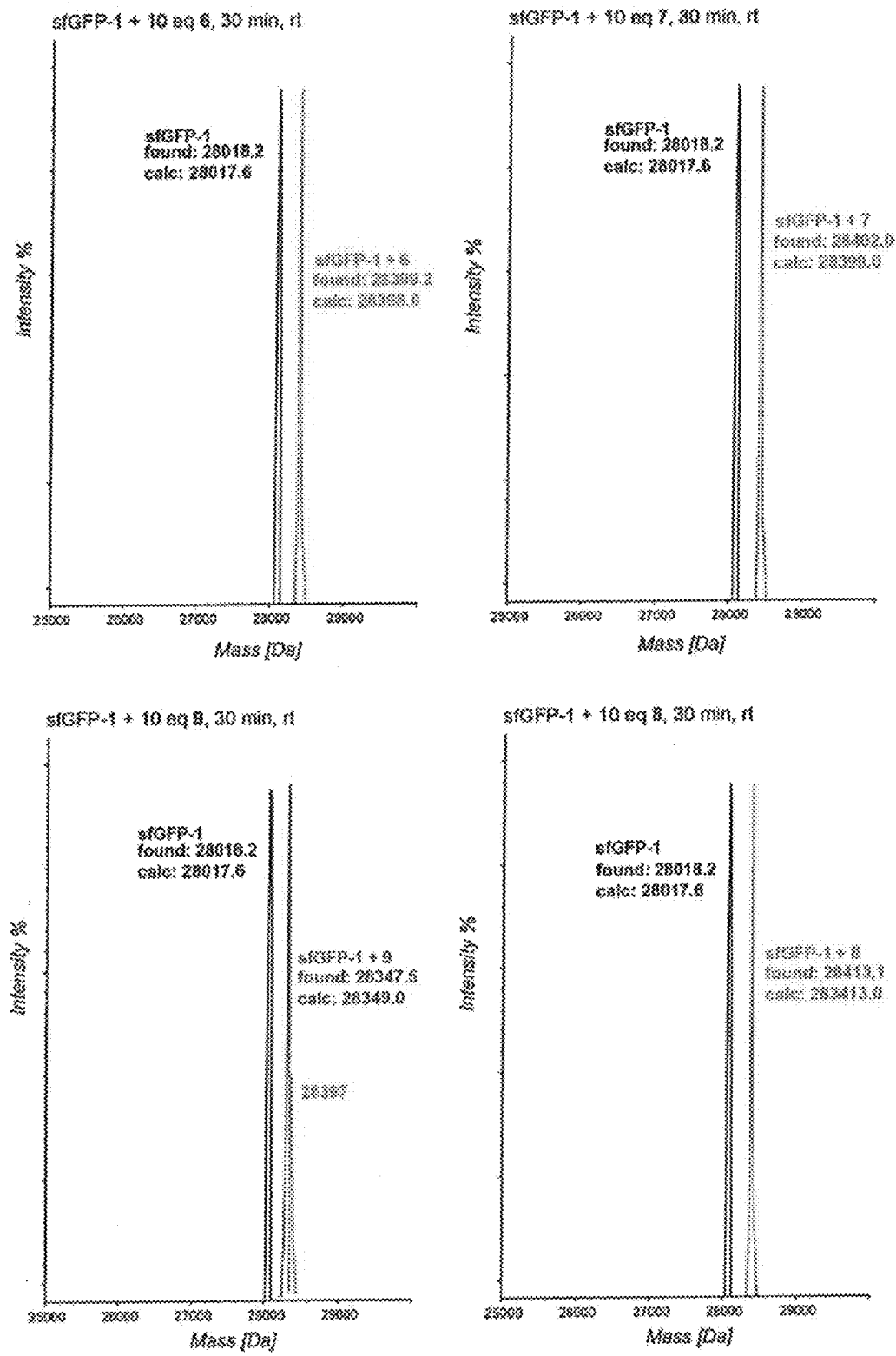
Figure 18 (Supplementary Figure S7)

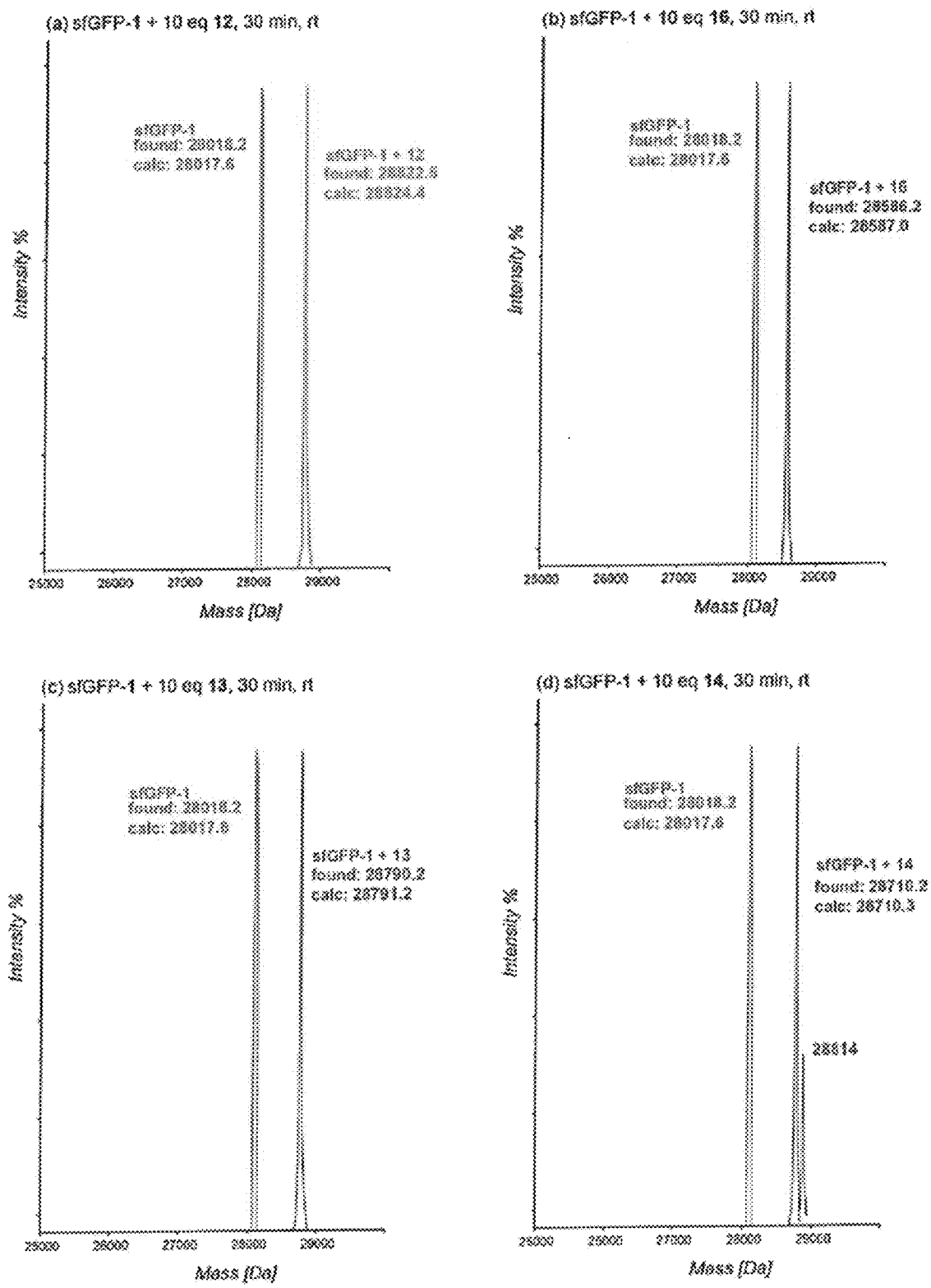
Figure 19 (Supplementary Figure S8)

Figure 20 (Supplementary Figure S9)
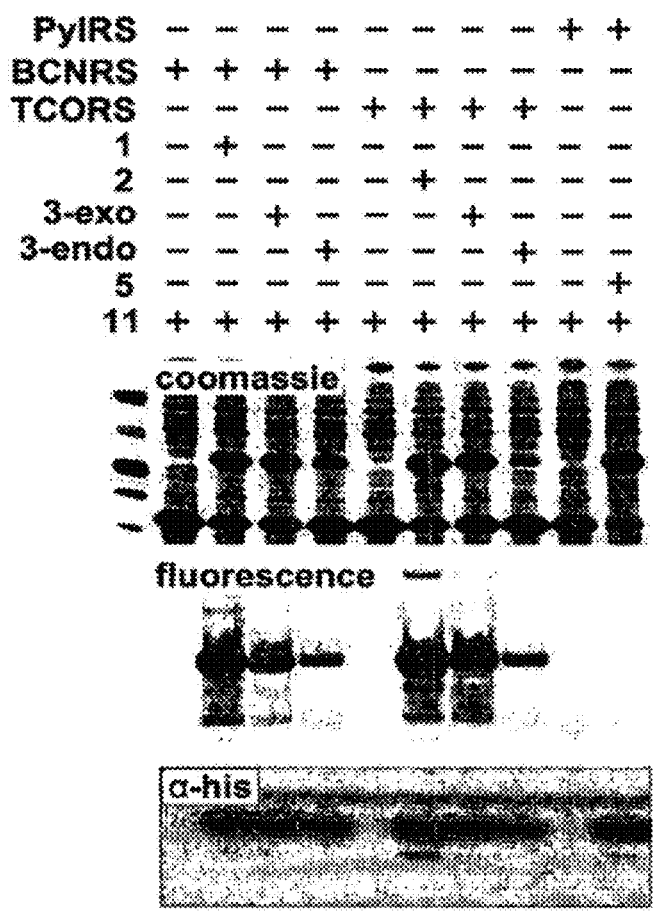
Figure 21 (Supplementary Figure S10)
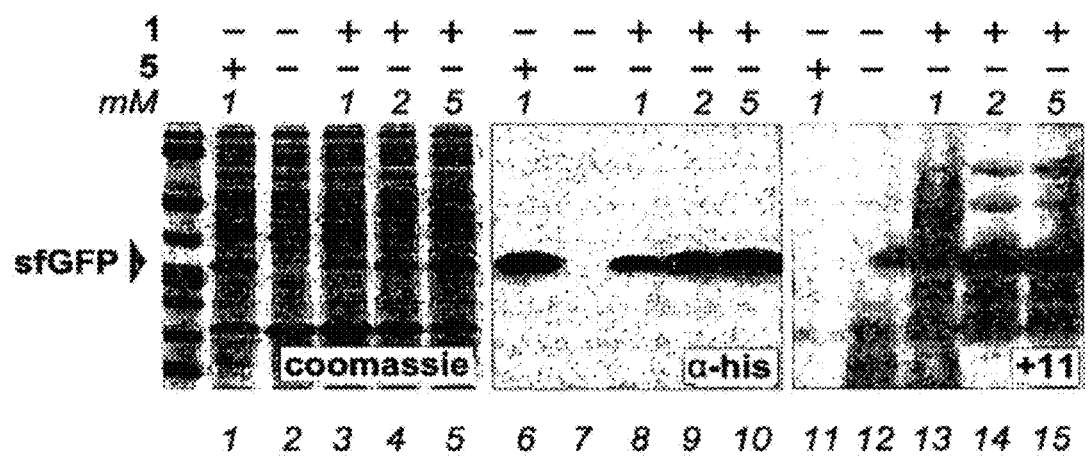

2 min labeling with tetrazine-dye conjugate 11
0.5 mM 1
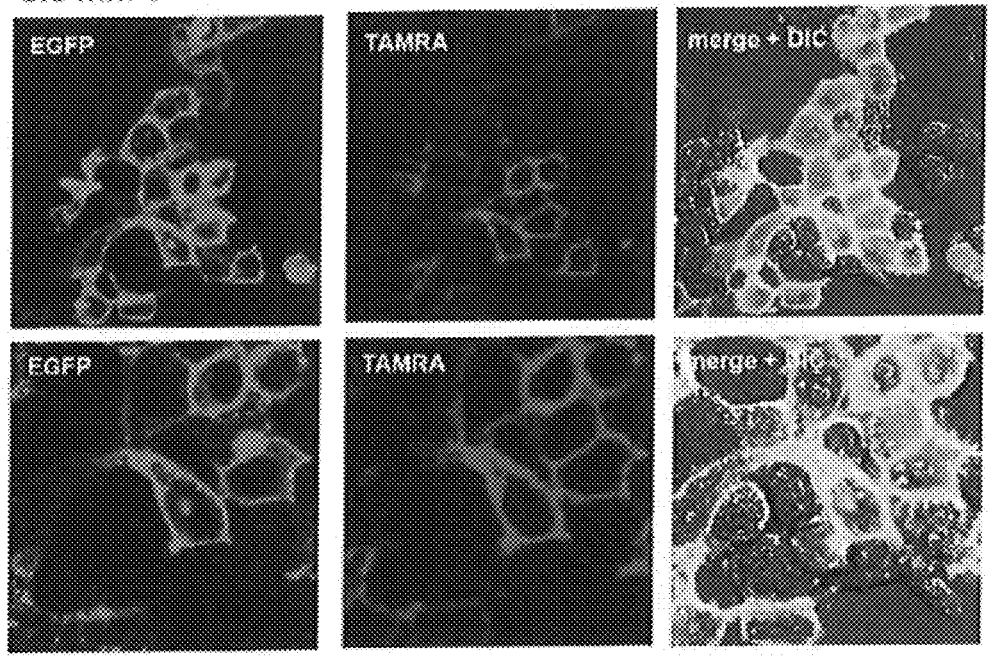
1 mM 5
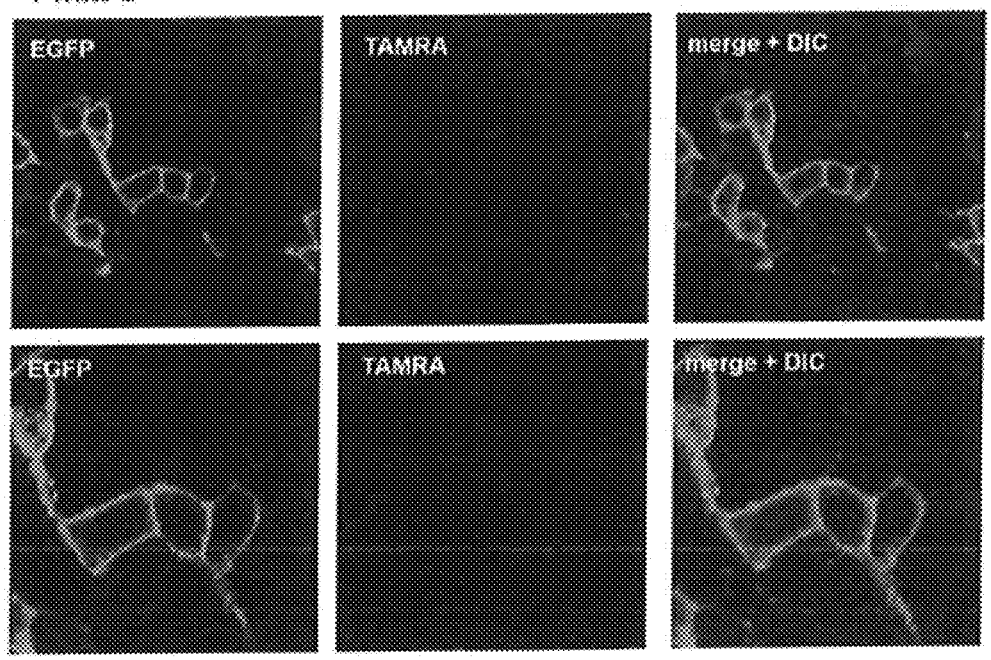
Figure 22 (Supplementary Figure S11)

5 min labeling with tetrazine-dye conjugate 11
0.5 mM 1
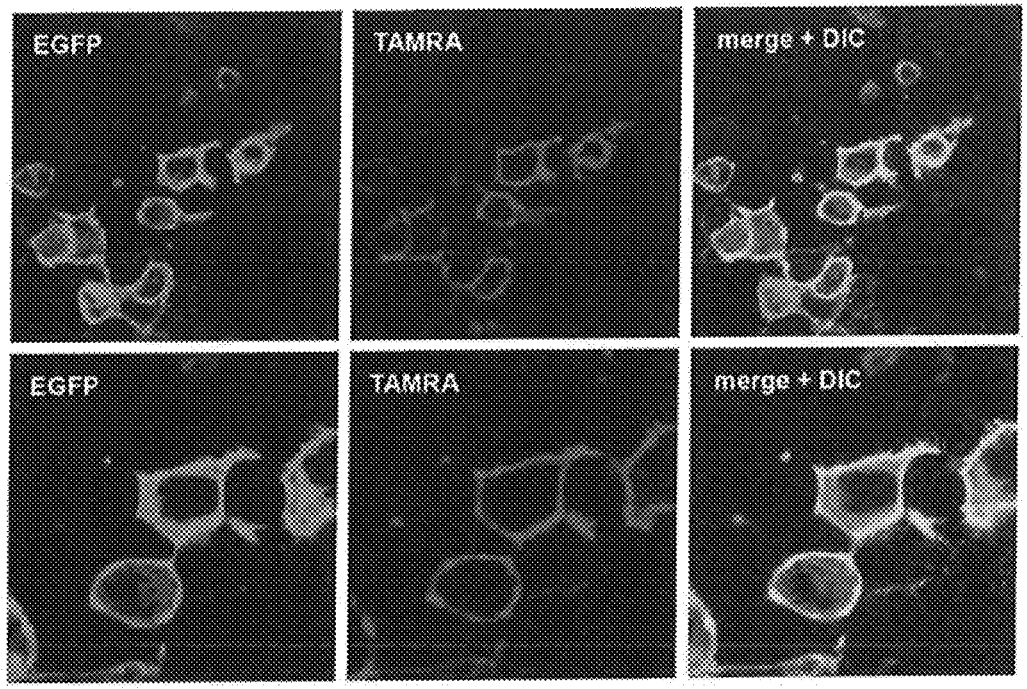
1 mM 5
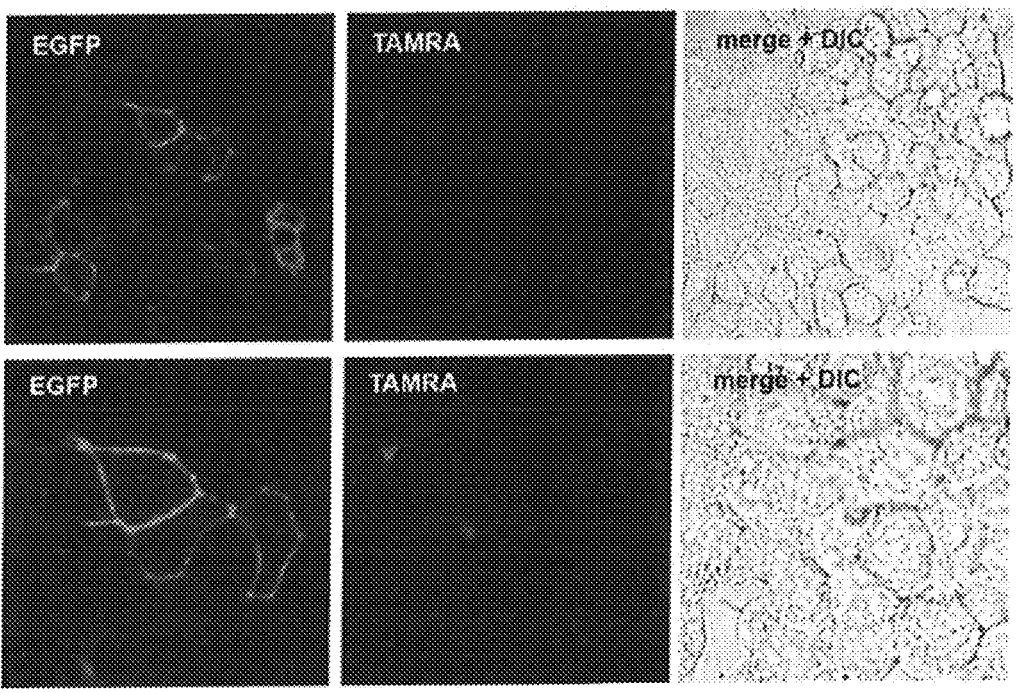
Figure 23 (Supplementary Figure S12)

10 min labeling with tetrazine-dye conjugate 11
0.5 mM 1
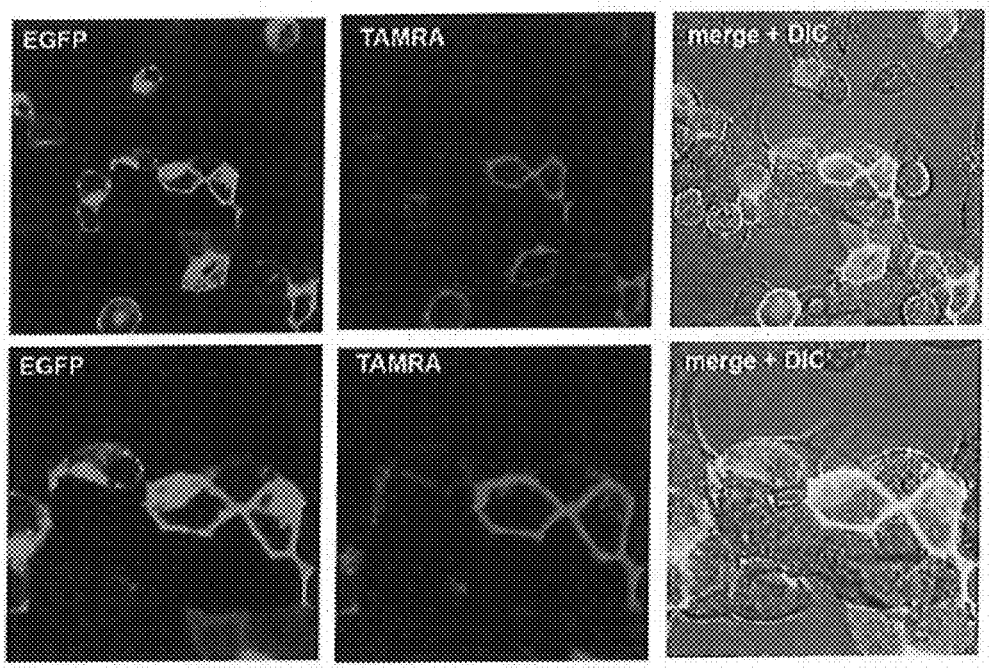
1 mM 5
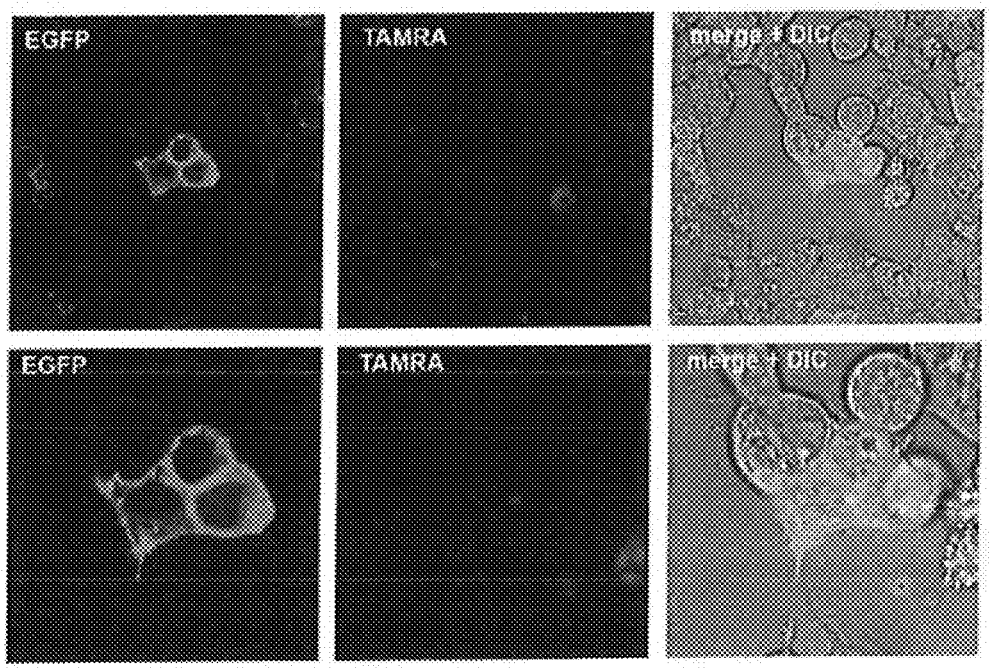
Figure 24 (Supplementary Figure S13)

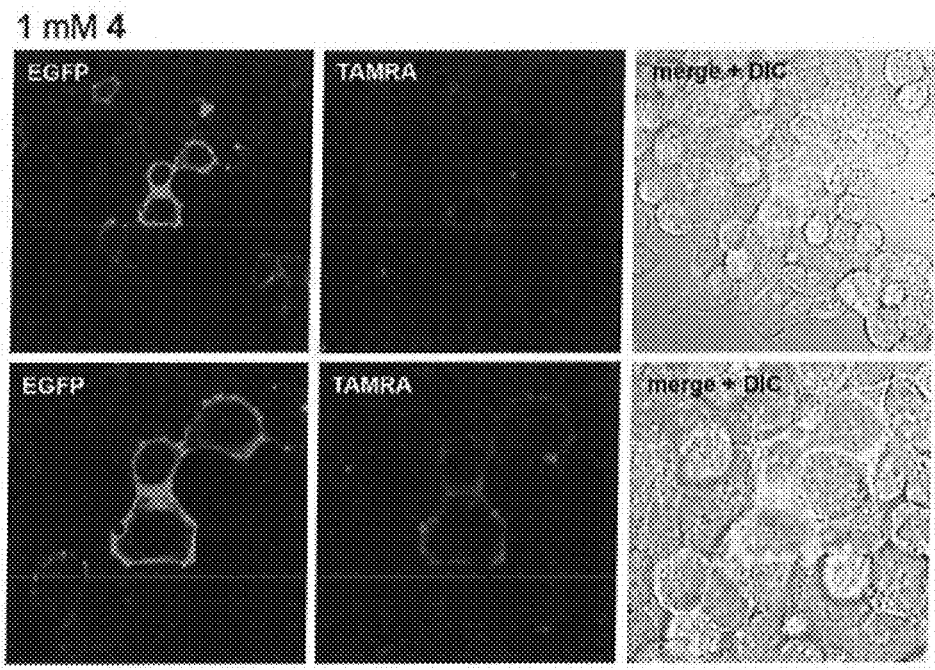
Figure 25 (Supplementary Figure S14)
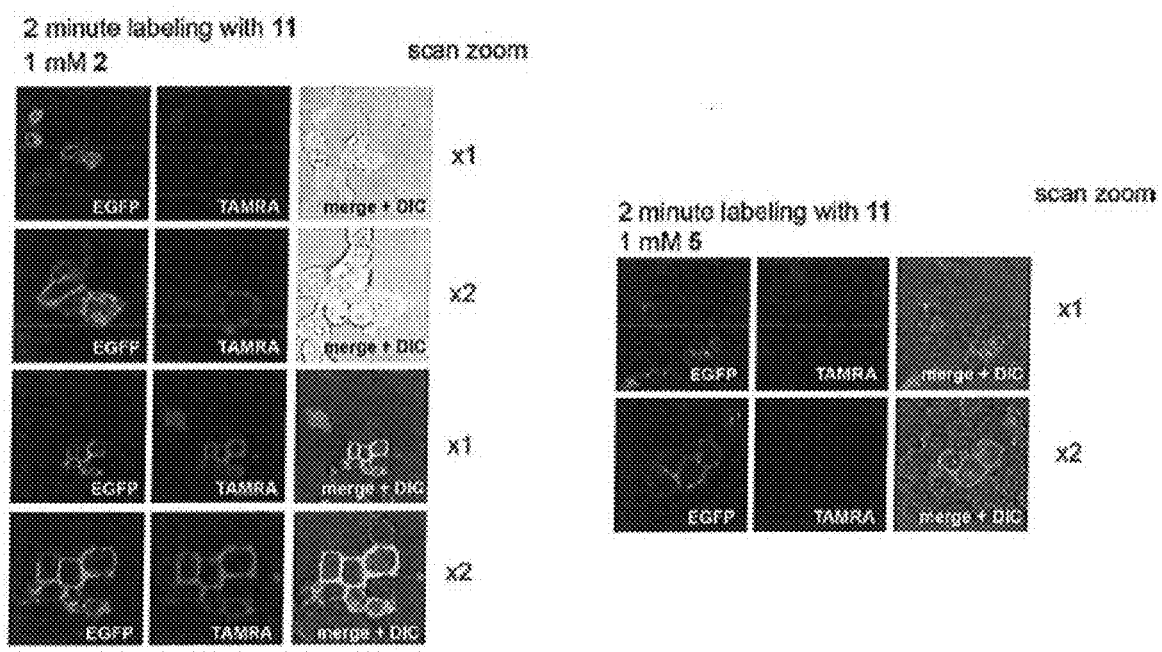
Figure 26 (Supplementary Figure S15)

Figure 27 (Supplementary Figure S16).
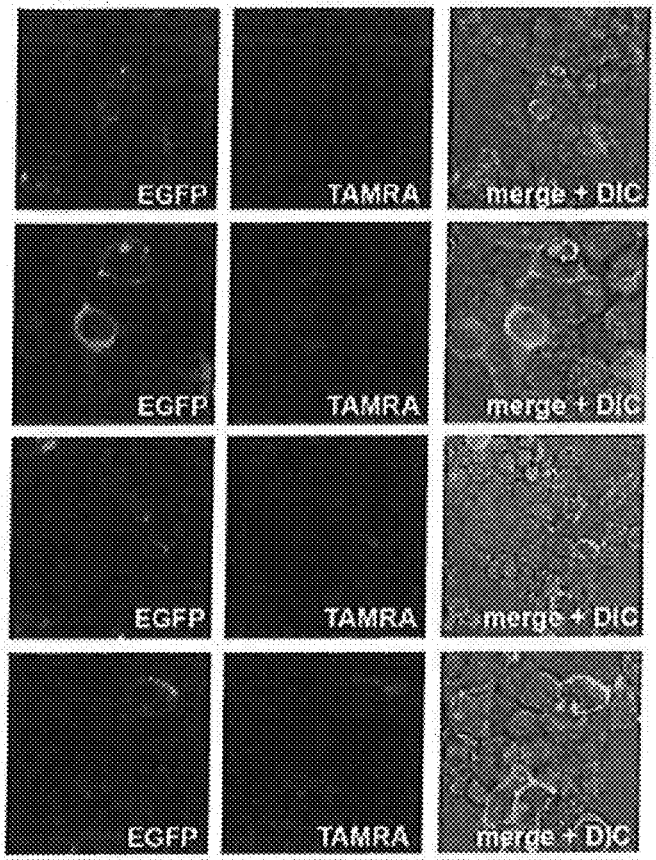
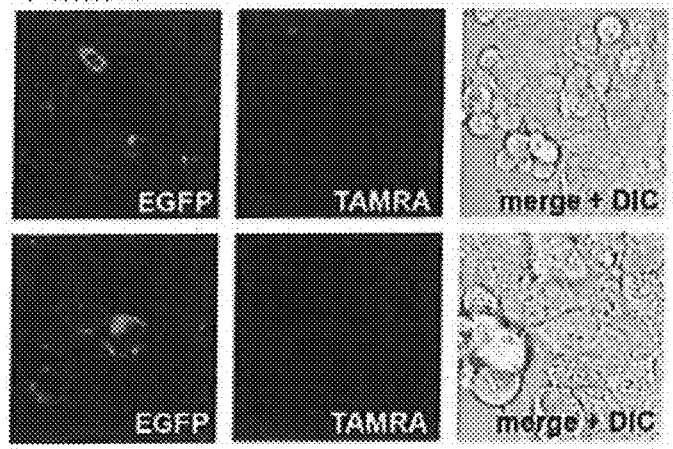

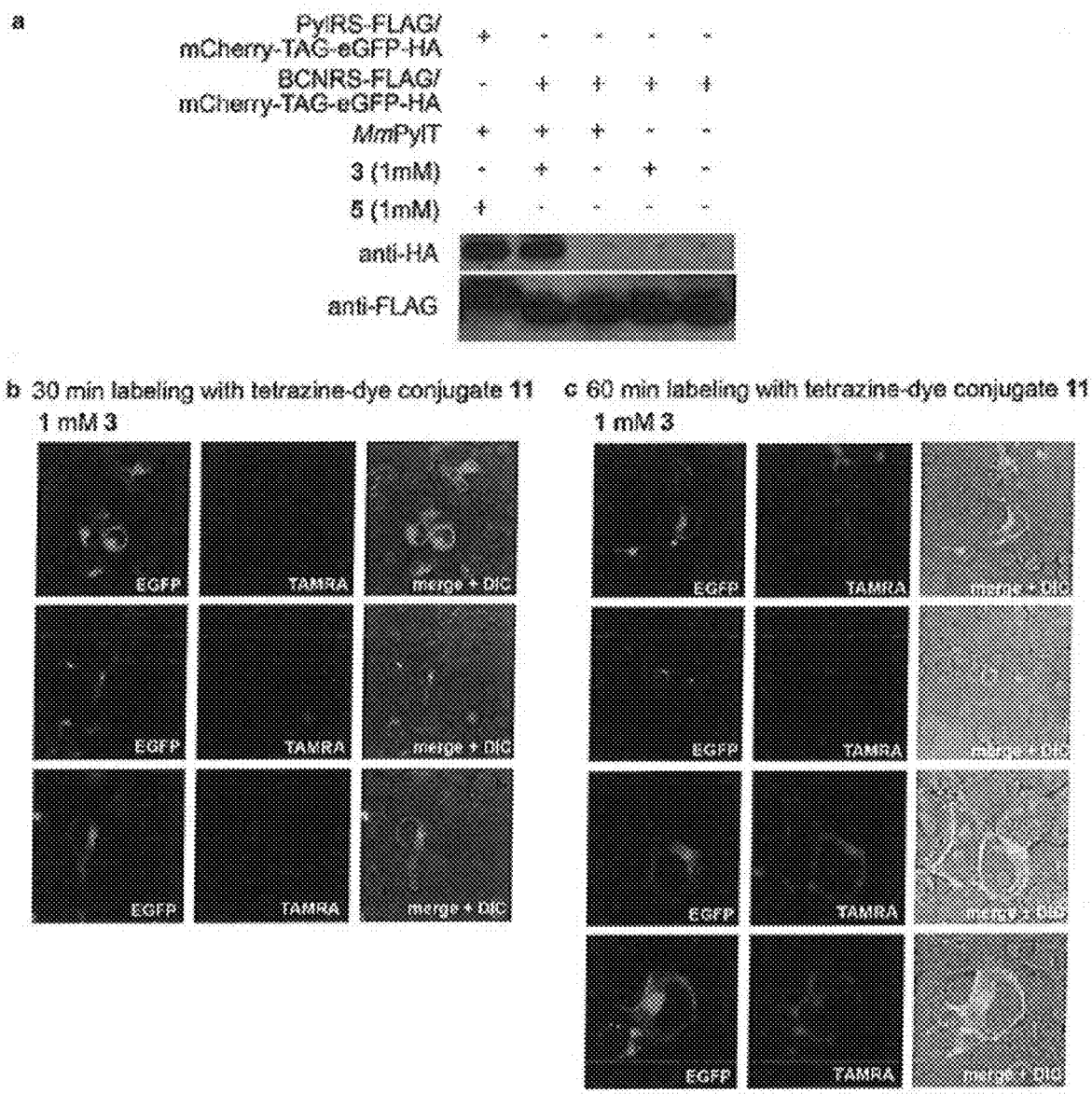
Figure 28 (Supplementary Figure S17)

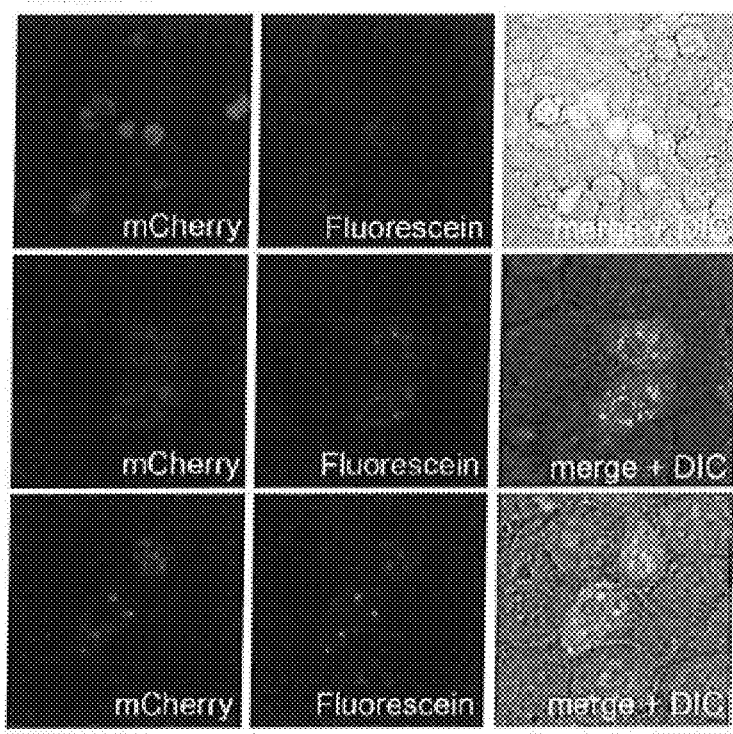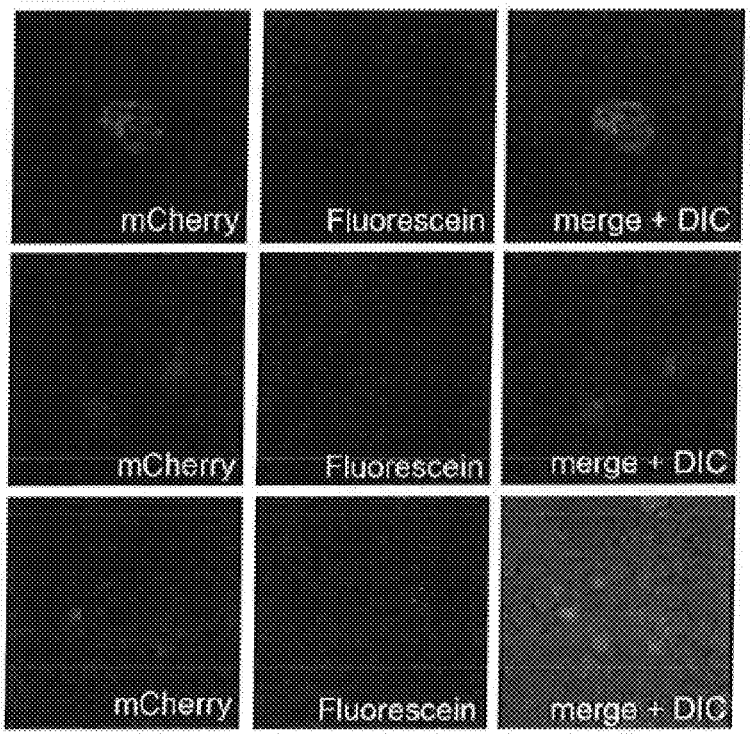
Figure 29 (Supplementary Figure S18

METHODS OF INCORPORATING AN AMINO ACID COMPRISING A BCN GROUP INTO A POLYPEPTIDE USING AN ORTHOGONAL CODON ENCODING IT AND AN ORTHOGONAL PYLRS SYNTHASE

CROSS-REFERENCE TO RELATED APPLICATIONS

This application is a divisional application of U.S. patent application Ser. No. 14/401,803, filed Nov. 17, 2014 which is a national phase filing under 35 U.S.C. § 371 of International Patent Application No. PCT/GB2013/051249, filed May 15, 2013, which claims the benefit of priority to United Kingdom Patent Application No. 1210303.2, filed Jun. 8, 2012, and United Kingdom Patent Application No. 1208875.3, filed May 18, 2012, the disclosures of all of which are incorporated herein in their entireties for all purposes.

INCORPORATION BY REFERENCE OF SEQUENCE LISTING

The Sequence Listing associated with this application is provided in text format in lieu of a paper copy, and is hereby incorporated by reference into the specification. The name of the text file containing the Sequence Listing is LARC_003_D01US_SeqList_ST25.txt. The text file is about 62 kilobytes, created on May 6, 2020, and is being submitted electronically via EFS-Web.

Field of the invention

The invention relates to site-specific incorporation of bio-orthogonal groups via the expanded) genetic code. In particular the invention relates to incorporation of chemical groups into polypeptides via accelerated inverse electron demand Diels-Alder reactions between genetically incorporated amino acid groups such as dienophiles, and chemical groups such as tetrazines.

Background to the Invention

The site-specific incorporation of bio-orthogonal groups via genetic code expansion provides a powerful general strategy for site specifically labelling proteins with any probe. However, the slow reactivity of the bio-orthogonal functional groups that can be geneticaliy encoded has limited this strategy's utility.

The rapid, site-specific labeling of proteins with diverse probes remains an outstanding challenge for chemical biologists; enzyme mediated labeling approaches may be rapid, but use protein or peptide fusions that introduce perturbations into the protein under study and may limit the sites that can be labeled, while many 'bio-orthogonal' reactions for which a component can be genetically encoded are too slow to effect the quantitative and site specific labeling of proteins on a time scale that is useful to study many biological processes.

There is a pressing need for general methods to site-specifically label proteins, in diverse contexts, with user-defined probes.

Inverse electron demand Diels-Alder reactions between strained alkenes including norbomenes and trans-cyclooctenes, and tetrazines have emerged as an important class of rapid bio-orthogonal reactions[1-4]. The rates reported for some of these reactions are incredibly fast[3,4].

Very recently, three approaches have been reported for specificaly labeling proteins using these reactions:

A lipoic acid ligase variant that accepts a trans-cyclooctene substrate has been used to label proteins bearing a 13 amino acid lipoic acid ligase tag in a two step procedures[5].

A tetrazine has been introduced at a specific site in a protein expressed in E. coli via genetic code expansion, and derivatized with a strained trans-cyclooctene-diacetyl fluorescein[6].

The incorporation of a strained alkene (a norbomene containing amino acid) has been demonstrated via genetic code expansion and site-specific fluorogenic labeling with tetrazine fuorophores in vitro, in E. coli and on mammalian cells[7]. The incororation of nor-bomene containing amino acids has also been recently reported[8,9].

The low-efficiency incorporation of a trans-cycclooctene containing amino acid (TCO)(2) has been reported, with detection of some fluorescent labelling in fixed cells[9].

Recent work with model reactions in organic solvents suggests that the reaction between BCN (first described in strain promoted reactions with azides)[10] and tetrazines may proceed very rapidly[11]. However, this reaction, unlike the much slower reaction of simple cyclooctynes with azides, nitrones[12-16] and tetrazines[9,17], has not been explored in aqueous media or as a chemoselective route to labeling macromolecules.

The present invention seeks to overcome problem(s) associated with the prior art.

SUMMARY OF THE INVENTION

Certain techniques for the attachment of tetrazine compounds to polypeptides exist in the art. However those techniques suffer from slow reaction rates. Moreover, those techniques allow for multiple chemical species to be produced as reaction products. This can lead to problems, for example in variable molecular distances between dye groups which can problematic for fluorescence resonance energy transfer (FRET) analysis. This can also be problematic for the production of therapeutic molecules since heterogeneity of product can be a drawback in this area.

The present inventors have provided a new amino acid bearing a bicyclo[6.1.0]non-4-yn-9-ylmethanol (BCN) group. This allows a dramatically increased reaction rate, which is advantageous. In addition, this allows a single-product addition reaction to be carried out. This leads to a homogeneous product, which is an advantage. This also elminates isomeric variation (spatial isomers) in the product, which provides technical benefits in a range of applications as demonstrated herein. In addition, the product of the BCN addition reaction does not epimerise, whereas the products from (for example) norbomene and/or TCO reactions do give rise to epimers. Thus it is an advantage of the invention that the problems of epimers are also avoided.

Thus in one aspect the invention provides a polypeptide comprising an amino acid having a bicyclo[6.1.0]non-4-yn-9-ylmethanol (BCN) group. This has the advantage of providing a single reaction product following addition of (for example) tetrazine compounds. Alternate techniques such as norbomene addition or TCO addition give a mixture of products comprising different isomers, such as regio or stereo isomers. One reason for this advantage is that the BCN part of the molecule has mirror symmetry so that the product is the same, whereas for TCO/norbomene that part of the molecule is chiral and so attachment can be to the 'top face' or 'bottom face' of the double bond, leading to different isomers in the products.

Thus the invention provides the advantage of homogeneity of product when used in the attachment of further groups to the polypeptide such as tetrazine compounds.

Suitably said BCN group is present as a residue of a lysine amino acid.

In another aspect, the invention relates to a method of producing a polypeptide comprising a BCN group, said method comprising genetically incorporating an amino acid comprsising a BCN group into a polypeptide.

Suitably producing the polypeptide comprises
(i) providing a nucleic acid encoding the polypeptide which nucleic acid comprises an orthogonal codon encoding the amino acid having a BCN group:
(ii) translating said nucleic acid in the presence of an orthogonal tRNA synthetase/tRNA pair capable of recognising said orthogonal codon and incorporating said amino acid having a BCN group into the polypeptide chain.

Suitably said amino acid comprising a BCN group is a BCN lysine.

Suitably said orthogonal condon comprises an amber codon (TAG), said tRNA comprises MbtRNA$_{CUA}$. Suitably said amino acid having a BCN group comprises a bicyclo [6.1.0]non-4-yn-9-ylmethanol (BCN) lysine. Suitably said tRNA synthetase comprises a PylRS synthetase having the mutations Y271M, L274G and C313A (BCNRS).

Suitably said amino acid having a BCN group is incorporated at a position corresponding to a lysine residue in the wild type polypeptide. This has the advantage of maintaining the closest possible structural relationship of the BCN containing polypeptide to the wild type polypeptide from which it is dervied.

In another aspect, the invention relates to a polypeptide as described above which comprises a single BCN group. Thus suitably the polypeptide comprises a single BCN group. This has the advantage of maintaining specificity for any further chemical modifications which might be directed at the BCN group. For example when there is only a single BCN group in the polypeptide of interest then possible issues of partial modification (e.g. where only a subset of BCN groups in the polypeptide are subsequently modified), or issues of reaction microenvironments varying between alternate BCN gorups in the same polypeptides (which could lead to unequal reactivity between different BCN group(s) at different locations in the polypeptide) are advantageously avoided.

A key advantage of incorporation of a BCN group is that ispermits a range of extremely useful further compounds such as labels to be easily and specifically attached to the BCN group.

In another aspect, the invention realtes to a polypeptide as described above wherein said BCN group is joined to a tetrazine group.

In another aspect, the invention relates to a polypeptide as described above wherein said tetrazine group is further joined to a fluorophore.

Suitably said fluorophore comprises fluorescein, tetramethyl rhodamine (TAMRA) or boron-dipyrromethene (BODIPY).

In another aspect, the invention relates to a novel unnatural amino acid comprising a BCN group.

In another aspect, the invention relates to an amino acid comprising bicyclo[6.1.0]non -4-yn-9-ylmethanol (BCN).

In another aspect, the invention relates to an amino acid which is bicyclo[6.1.0]non-4-yn-9-ylmethanol (BCN) lysine.

Suitably BCN lysine as described above has the structure:

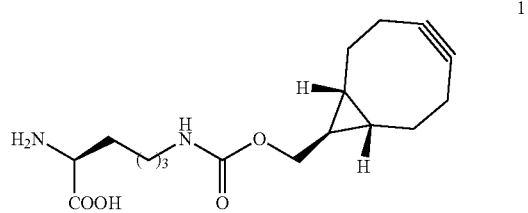

In another aspect, the invention relates to a method of producing a polypeptide comprising a tetrazine group, said method comprising providing a polypeptide as described above, contacting said polypeptide with a tetrazine compound, and incubating to allow joining of the tetrazine to the BCN group by an inverse electron demand Diels-Alder cycloaddition reaction.

Suitably the tetrazine is selected from 6 to 17 of FIG. 1.

Suitably the pseudo first order rate constant for the reaction is at least 80 $M^{-1}s^{-1}$.

Suitably the terazine is selected from 6, 7, 8 and 9 of FIG. 1 and the pseudo first order rate constant for the reaction is at least 80 $M^{-1}s^{-1}$.

This chemistry has teh advantage of speed of reaction.

Suitably said reaction is allowed to proceed for 10 minutes or less.

Suitably said reaction is allowed to proceed for 1 minute or less.

Suitably said reaction is allowed to proceed for 30 seconds or less.

It will be noted that certain reaction environments may affect reaction times. Most suitably the shortest times such as 30 seconds or less are applied to in vitro reactions.

Reactions in vivo, or in eukaryotic cultrue conditions such as tissue cultrure medium or other suitable media for eukaryotic cells, may need to be conducted for longer than 30 seconds to achieve maximal labelling. The skilled operator can determine optimum reaction times by trial and error based on the guidance provided herein.

Suitably said tetrazine compound is a tetrazine compound selected from the group consisting of 11 and 17 of FIG. 1.

In another aspect, the invention relates to a PylRS tRNA synthetase comprising the mutations Y271M, L274G and C313A.

Suitably said PylRS lRNA synthetase has a sequence corresponding to MbPylRS tRNA synthetase comprising the mutations Y271M, L274G and C313A.

In another aspect the invention relates to the use of the PylRS tRNA synthetase(s) of the invention for the incorporation of amino acid comprising bicyclo[6.1.0]non-4-yn-9-ylmethanol (BCN) into a polypeptide.

In another aspect the invention relates to a method for the incorporation of amino acid comprisng bicyclo[6.1.0]non-4-yn-9-ylmethanol (BCN) into a polypeptide comprising use of the PylRS tRNA synthetase(s) of the invention to incorporate same.

In another aspect, the invention relates to a homogenous recombiant polypeptide as described above. Suitably said polypeptide is made by a method as described above.

Also disclosed is a polypeptide produced according to the method(s) described herein. As well as being the product of those new methods, such a polypeptide has the technical feature of comprising BCN.

Mutating has it normal meaning in the art and may refer to the substitution or truncation or deletion of the residue, motif or domain referred to. Mutation may be effected at the polypeptide level e.g. by synthesis of a polypeptide having the mutated sequence, or may be effected at the nucleotide level e.g. by making a nucleic acid encoding the mutated sequence, which nucleic acid may be subsequently translated to produce the mutated polypeptide. Where no amino acid is specified as the replacement amino acid for a given mutation site, suitably a randomisation of said site is used. As a default mutation, alanine (A) may be used. Suitably the mutations used at particular site(s) are as set out herein.

A fragment is suitably at least 10 amino acids in length, suitably at least 25 amino acids, suitably at least 50 amino acids, suitably at least 100 amino acids, suitably at least 200 amino acids, suitably at least 250 amino acids, suitably at least 300 amino acids, suitably at least 313 amino acids, or suirably the majority of the polypeptide of interest.

DETAILED DESCRIPTION OF THE INVENTION

Here we demonstrate a fluorogenic reaction between bicyclo[6.1.0]non-4-yn-9-ylmethanol (BCN) and tetrazines. The rates for these reactions are 3-7 orders of magnitude faster than the rates for many 'bio-orthogonal' reactions. We describe aminoocyl-tRNA synthetase/tRNA pairs and their use for the efficient site-specific incorporation of a BCN-containing amino acid, 1, and a transcyclooctene-containing amino acid 2 (which also reacts extremely rapidly with tetrazines) into proteins expressed in *E. coli* and mammalian cells. We demonstrate the site-specific, fluorogenic labeling of proteins containing 1 and 2 in vitro. In *E. coli* and in live mammalian cells at the first measureable time point (after seconds or minutes). Moreover we demonstrate the specificity of tetrazine labeling with respect to a proteome as well as the advantages of the approach with respect to current 'bio-orthogonal' reactions for which a component can be encoded. The approaches developed may be applied to site-specific protein labeling in animals, and they find utility in labelling and imaging studies.

A polypeptide comprising an amino acid having a dienophile group, characterised in that said dienophile group comprises a bicyclo[6.1.0]non-4-yn-9-ylmethanol (BCN) group.

We describe genetic encoding of bicyclononynes and trans-cyclooctenes for site-specific protein labelling in vitro and in live mammalian cells via fluorogenic Diels-Alder reaction.

The methods of the invention may be practiced in vivo or in vitro.

In one embodiment, suitably the methods of the invention are not applied to the human or animal body. Suitably the methods of the invention are in vitro methods. Suitably the methods do not require the presence of the human or animal body. Suitably the methods are not methods of diagnosis or of surgery or of therapy of the human or animal body.

Dienophile/Trans-Cyclooctene (TCO) Aspects

In a broad aspect the invention relates to a polypeptide comprising an amino acid having a dienophile group capable of reacting with a tetrazine group. Suitably said dienophile group is present as a residue of a lysine amino acid.

In one embodiment, the invention relates to a method of producing a polypeptide comprising a dienophile group, said method comprising genetically incorporating an amino acid comprising a dienophile group into a polypeptide.

Suitably producing the polypeptide comprises
(i) providing a nucleic acid encoding teh polypeptide which nucleic acid comprises an orthogonal condon encoding the amino acid having a dienophile group:
(ii) translating said nucleic acid in the presence of an orthogonal tRNA synthetase/tRNA pair capable of recognising said orthogonal codon and incorporating said amino acid having a dienophile group into the polypeptide chain. Suitably said amino acid comprising a dienophile group is a dienophile lysine.

Suitably said orthogonal codon comprises an amber codon (TAG), said tRNA comprises $MbtRNA_{CUA}$, said amino acid having a dienophile group comprises a trans-cyclooctene-4-ol (TCO) containing amino acid and said tRNA sythetase comprises a pylRS synthetase having the mutations Y271A, L274M and C313A (TCORS).

Suitably said PylRS tRNA synthetase has a sequence corresponding to MbPylRS tRNA synthetase comprising the mutations Y271A, L274M and C313A (TCORS). In another aspect the invention relates to the use of the PylRS tRNA synthetase(s) of the invention for the incorporation of amino acid comprising trans-cyclooctene-4-ol (TCO) into a polypeptide.

In another aspect the invention relates to a method for the incorporation of amino acid comprising trans-cyclooctene-4-ol (TCO) into a polypeptide comprising use of the PylRS tRNA synthetase(s) of the invention to incorporate same.

Aspects of the invention regarding teh joining of tetrazine compounds to the unnatural amino acids discussed herein apply equally to TCO amino acids as they do to BCN amino acids unless otherwise indicated by the context.

We report the exceptionally rapid, fluorogenic, reaction of BCN with a range of tetrazines under aqueous conditions at room temperature. The rate constants for BCN-tetrazine reactions are 500 to 1000 times greater than fr the reaction of norbomene with the same tetrazines. The rate constants fro TCO-tetrazine reactions are 10-15 fold greater than those for BCN with the same tetrazine. The reaction between strained alkenes and tetrazines may lead to a mixture of diastereomers and regioisomers, as well as isomers from dihydropyridazine isomerization.[3,4]

In contrast the BCN tetrazine reaction leads to the formation of a single product. This may be an advantage in applications where homogeneity in the orientation of probe attachement may be important, including single molecule spectroscopy, and FRET approaches.

We have described aminoacyl-tRNA synthetase/tRNA pairs and their uses to direct the efficient, site-specific incorporation of 1 and 2 into proteins in *E. coli* and mammalian cells.

We have demonstrated that the specific, quantitative labeling of proteins—a process that takes tens of minutes to hours with an encoded norbornene[7] and tens of hours with an encoded azide using copper-catalysed click chemistry with alkyne probes[21]—may be complete within seconds using the encoded amino acids 1 and 2. While we do not observe labeling of an azide incorporated into EGFR on the mammalian cell surface with cyclooctynes[7] and labeling of an encoded norbomene in EGFR allows labeling only after 2 hours with tetrazines[7], strong and saturated labeling of EGFR incorporating 1 and 2 was observed at the first time point measured (2 min) using nanomolar concentrations of tetrazine-dye conjugates. These experiments confirm that the rapid BCN-tetrazine and TCO-tetrazine ligations characterized in small molecule experiments translate into substantial improvements in protein labeling in diverse contexts. While we have demonstrated the advantages of this approach in vitro, in *E. coli* and in live mammalian cells the ability to incorporate unnatural amino acids in *C. elegans* using the PylRS/tRNA$_{CUA}$ pair[29] suggests that it may be possible to extend the labeling approach described here to site-specific protein labeling in animals.

Genetic Incorporation and Polypeptide Production

In the method according to the invention, said genetic incorporation preferably uses an orthogonal or expanded genetic code, in iwhich one or more specific orthogonal condons have been allocated to encode the specifc amino acid residue with the BCN group so that it can be genetically incorporated by using an orthogonal tRNA synthetase/tRNA pair. The orthogonal tRNA synthetase/tRNA pair can in principle be any such pair capable of charging the tRNA with the amino acid comprising the BCN group and capable of incorporating that amino acid comprising the BCN group into the polypeptide chain in response to the orthogonal codon.

The orthogonal codon may be the orthogonal codon amber, ochre, opal or a quadruplet codon. The codon simply has to correspond to the orhtogonal tRNA which will be used to carry the amino acid comprising the BCN group. Preferably the orthogonal codon is amber.

It should be noted that the specific examples shown herein have used the amber codon and the corresponding tRNA/tRNA synthetase. As noted above, these may be varied. Alternatively, in order to use other codons without going to the trouble of using or selecting alternative tRNA/tRNA synthetase pairs capable of working with the amino acid comprising the BCM group, the anticodon region of the tRNA may simply be swapped for the desired anticodon region for the codon of choice. The anticodon region is not involved in the charging or incorporation functions of the tRNA nor recognition by the tRNA synthetase so such swaps ore entirety within the ambit of the skilled operator.

Thus alternative orthogonal tRNA synthetase/tRNA pairs may be used if desired.

Preferably the orthogonal synthetase/tRNA pair are *Methanosarcina bakeri* MS pyrrolysine tRNA synthetase (MbPylRS) and its cognate amber suppressor tRNA (MbtRNA$_{CUA}$).

The *Methanosarcina bakeri* PylT gene encodes the MbtRNA$_{CUA}$ tRNA.

The *Methanosarcina bakeri* PylS gene encodes the MbPylRS tRNA synthetase protein. When particular amino acid residues are referred to using numberic addresses, the numbering is taken using MbPylRS (*Methanosarcina barkeri* pyrrolysyl-tRNA synthetase) amino acid sequence as the reference sequence (i.e. as encoded by the publicly available wild type *Methanosarcina barkeri* PylS gene Accession number Q46E77).

```
SEQ ID. NO. 1:
MDKKPLDVLI SATGLWMSRT GTLHKIKHYE VSRSKIYIEM

ACGDHLVVNN SRSCRTARAF RHHKYRKTCK RCRVSDEDIN

NFLTRSTEGK TSVKVKVVSA PKVKKAMPKS VSRAPKPLEN

PVSAKASTDT SRSVPSPAKS TPNSPVPTSA PAPSLTRSQL

DRVEALLSPE DKISLNIAKP FRELESELVT RRKNDFQRLY
```

```
-continued
TNDREDYLGK LERDITKFFV DRDFLEIKSP ILIPAEYVER

MGINNDTELS KQIFRVDKNL CLRPMLAPTL YNYLRKLDRI

LPDPIKIFEV GPCYRKESDG KEHLEEFTMV NFCQMGSGCT

RENLESLIKE FLDYLEIDFE IVGDSCMVYG DTLDIMHGDL

ELSSAVVGPV PLDREWGIDK PWIGAGFGLE RLLKVMHGFK

NIKRASRSES YYNGISTNL.
```

If required, the person skilled in the art may adapt MbPylRS tRNA synthetase protein by mutating it so as to optimise for the BCN amino acid to be used. The need for mutation depends on the BCN amino acid used An example where the MbPylRS tRNA synthetase may need to be mutated is when the BCN amino acid is not proccessed by the MbPylRS tRNA synthetase protein.

Such mutation may be carried out by introducing mutations into the MbPylRS tRNA synthetase, for example at one or more of the following positions in the MbPylRS tRNA synthetase: M241, A267, Y271, L274 and C313.

An example is when said amino acid having a BCN group comprises a bicyclo [6.1.0]non -4-yn-9-ylmethanol (BCN) lysine. Suitably said tRNA synthetase comprises a PylRS synthetase such as MbPylRS having the mutations Y271M, L274G and C313A (BCNRS).

An example is when said amino acid having a dienophile group comprises a trans -cyclooctene-4-ol [TCO] containing amino acid. Suitably said tRNA synthetase comprises a PylRS synthetase such as MbPylRS having the mutations Y271A, L274M and C313A (TCORS).

tRNA Synthetases

The tRNA synthetase of the invention may be varied. Although specific tRNA synthetase sequences may have been used in the examples, the invention is not intended to be confined only to those examples.

In principle any tRNA synthetase which provides the same tRNA charging (aminoocylation) function can be employed in the invention.

For example the tRNA synthetase may be from any suitable species such as from archea, for example from *Methanosarcina barkeri* MS; *Methanosarcina barkeri* str. Fusaro: *Methanosarcina mazei* Go1: *Methanosarcina acetivorans* C2A: *Methanosarcina thermophila*; or *Methanococcoides burtanii*. Alternatively the tRNA synthetase may be from bacteria, for example from *Desulfitobacterium hafniense* DCB-2; *Desulfitobacterium hafniense* Y51: *Desulfitobacterium hafniense* PCP1; *Desultofomaculum acetoxidans* DSM 771.

Exemplary sequences from these organisms are the publically available sequences. The following examples are provided as exemplary sequences for pyrrolysine tRNA synthetases:

>M. barkeriMS/1-419/
*Methanosarcina barkeri* MS
VERSION Q6WRH6.1 GI: 74501411
SEQ ID NO. 2:
MDKKPLDVLISATGLWMSRTGTLHKIKHHEVSRSKIYIEMACGDHLVVNNSRSCRTARAFRHHKYRKTC

KRCRVSDEDINNFLTRSTESKNSVKVRVVSAPKVKKAMPKSVSRAPKPLENSVSAKASTNTSRSVPSPAK

STPNSSVPASAPAPSLTRSQLDRVEALLSPEDKISLNMAKPFRELEPELVTRRKNDFQRLYTNDREDYLGK

LERDITKFFVDRGFLEIKSPILIPAEYVERMGINNDTELSKQIFRVDKNLCLRPMLAPTLYNYLRKLDRILPGP

IKIFEVGPCYRKESDGKEHLEEFTMVNFCQMGSGCTRENLEALIKEFLDYLEIDFEIVGDSCMVYGDTL

DIMHGDLELSSAVVGPVSLDREWGIDKPWIGAGFGLERLLKVMHGFKNIKRASRSESYYNGISTNL

>M. barkeriF/1-419/
*Methanosarcina barkeri* str. Fusaro
VERSION YP_304395.1 GI: 73668380
SEQ ID NO. 3:
MDKKPLDVLISATGLWMSRTGTLHKIKHYEVSRSKIYIEMACGDHLVVNNSRSCRTARAFRHHKYRKTC

KRCRVSDEDINNFLTRSTEGKTSVKVKVVSAPKVKKAMPKSVSRAPKPLENPVSAKASTDTSRSVPSPAK

STPNSPVPTSAPAPSLTRSQLDRVEALLSPEDKISLNIAKPFRELESELVTRRKNDFQRLYTNDREDYLGKLE

RDITKFFVDRDFLEIKSPILIPAEYVERMGINNDTELSKQIFRVDKNLCLRPMLAPTLYNYLRKLDRILPDPIKI

FEVGPCYRKESDGKEHLEEFTMVNFCQMGSGCTRENLESLIKEFLDYLEIDFEIVGDSCMVYGDTLDI

MHGDLELSSAVVGPVPLDREWGIDKPWIGAGFGLERLLKVMHGFKNIKRASRSESYYNGISTNL

>M. mazei/1-454
*Methanosarcina mazei* Go1
VERSION NP_633469.1 GI: 21227547
SEQ ID NO. 4:
MDKKPLNTLISATGLWMSRTGTIHKIKHHEVSRSKIYIEMACGDHLVVNNSRSSRTARALRHHKYRKTCK

RCRVSDEDLNKFLTKANEDQTSVKVKVVSAPTRTKKAMPKSVARAPKPLENTEAAQAQPSGSKFSPAI

PVSTQESVSVPASVSTSISSISTGATASALVKGNTNPITSMSAPVQASAPALTKSQTDRLEVLLNPKDEISL

NSGKPFRELESELLSRRKKDLQQIYAEERENYLGKLEREITRFFVDRGFLEIKSPILIPLEYIERMGIDNDTELS

KQIFRVDKNFCLRPMLAPNLYNYLRKLDRALPDPIKIFEIGPCYRKESDGKEHLEEFTMLNFCQMGSGC

TRENLESIITDFLNHLGIDFKIVGDSCMVYGDTLDVMHGDLELSSAVVGPIPLDREWGIDKPWIGAGF

GLERLLKVKHDFKNIKRAARSESYYNGISTNL

>M. acetivorans/1-443
*Methanosarcina acetivorans* C2A
VERSION NP_615128.2 GI: 161484944
SEQ ID NO. 5:
MDKKPLDTLISATGLWMSRTGMIHKIKHHEVSRSKIYIEMACGERLVVNNSRSSRTARALRHHKYRKTCR

HCRVSDEDINNFLTKTSEEKTTVKVKVVSAPRVRKAMPKSVARAPKPLEATAQVPLSGSKPAPATPVSA

PAQAPAPSTGSASATSASAQRMANSAAAPAAPVPTSAPALTKGQLDRLEGLLSPKDEISLDSEKPFRE

LESELLSRRKKDLKRIYAEERENYLGKLEREITKFFVDRGFLEIKSPILIPAEYVERMGINSDTELSKQVFRIDK

NFCLRPMLAPNLYNYLRKLDRALPDPIKIFEIGPCYRKESDGKEHLEEFTMLNFCQMGSGCTRENLEAII

TEFLNHLGIDFEIIGDSCMVYGNTLDVMHDDLELSSAVVGPVPLDREWGIDKPWIGAGFGLERLLKV

MHGFKNIKRAARSESYYNGISTNL

>M. thermophila/1-478
*Methanosarcina thermophila*, VERSION DQ017250.1 GI: 67773308
SEQ ID NO. 6:
MDKKPLNTLISATGLWMSRTGKLHKIRHHEVSKRKIYIEMECGERLVVNNSRSCRAARALRHHKYRKIC

KHCRVSDEDLNKFLTRTNEDKSNAKVTVVSAPKIRKVMPKSVARTPKPLENTAPVQTLPSESQPAPTTPIS

ASTTAPASTSTTAPAPASTTAPAPASTTAPASASTTISTSAMPASTSAQGTTKFNYISGGFPRPIPVQASAP

ALTKSQIDRLQGLLSPKDEISLDSGTPFRKLESELLSRRKDLKQIYAEEREHYLGKLEREITKFFVDRGFLEIK

SPILIPMEYIERMGIDNDKELSKQIFRVDNNFCLRPMLAPNLYNYLRKLNRALPDPIKIFEIGPCYRKESDG

-continued

KEHLEEFTMLNFCQMGSGCTRENLEAIIKDFLDYLGIDFEIVGDSCMVYGDTLDVMHGDLELSSAVV

GPVPMDRDWGINKPWIGAGFGLERLLKVMHNFKNIKRASRSESYYNGISTNL

>M. burtonii/1-416
Methanococcoides burtonii DSM 6242, VERSION YP_566710.1 GI: 91774018
SEQ ID NO. 7:
MEKQLLDVLVELNGVWLSRSGLLHGIRNFEITTKHIHIETDCGARFTVRNSRSSRSARSLRHNKYRKPCKR

CRPADEQIDRFVKKTFKEKRQTVSVFSSPKKHVPKKPKVAVIKSFSISTPSPKEASVSNSIPTPSISVVKDEV

KVPEVKYTPSQIERLKTLMSPDDKIPIQDELPEFKVLEKELIQRRDDLKKMYEEDREDRLGKLERDITEFFV

DRGFLEIKSPIMIPFEYIERMGIDKDDHLNKQIFRVDESMCLRPMLAPCLYNYLRKLDKVLPDPIRIFEIGP

CYRKESDGSSHLEEFTMVNFCQMGSGCTRENMEALIDEFLEHLGIEYEIEADNCMVYGDTIDIMHGD

LELSSAVVGPIPLDREWGVNKPWMGAGFGLERLLKVRHNYTNIRRASRSELYYNGINTNL

>D. hafniense_DCB-2/1-279
Desulfitobacterium hafniense DCB-2
VERSION YP_002461289.1 GI: 219670854
SEQ ID NO. 8:
MSSFWTKVQYQRLKELNASGEQLEMGFSDALSRDRAFQGIEHQLMSQGKRHLEQLRTVKHRPALLEL

EEGLAKALHQQGFVQVVTPTIITKSALAKMTIGEDHPLFSQVFWLDGKKCLRPMLAPNLYTLWRELERL

WDKPIRIFEIGTCYRKESQGAQHLNEFTMLNLTELGTPLEERHQRLEDMARWVLEAAGIREFELVTESSV

VYGDTVDVMKGDLELASGAMGPHFLDEKWEIVDPWVGLGFGLERLLMIREGTQHVQSMARSLSYL

DGVRLNIN

>D. hafniense_Y51/1-312
Desulfitobacterium hafniense Y51
VERSION YP_521192.1 GI: 89897705
SEQ ID NO. 9:
MDRIDHTDSKFVQAGETPVLPATFMFLTRRDPPLSSFWTKVQYQRLKELNASGEQLEMGFSDALSRDR

AFQGIEHQLMSQGKRHLEQLRTVKHRPALLELEEGLAKALHQQGFVQVVTPTIITKSALAKMTIGEDH

PLFSQVFWLDGKKCLRPMLAPNLYTLWRELERLWDKPIRIFEIGTCYRKESQGAQHLNEFTMLNLTELGT

PLEERHQRLEDMARWVLEAAGIREFELVTESSVVYGDTVDVMKGDLELASGAMGPHFLDEKWEIVD

PWVGLGFGLERLLMIREGTQHVQSMARSLSYLDGVRLNIN

>D. hafniensePCP1/1-288
Desulfitobacterium hafniense
VERSION AY692340.1 GI: 53771772
SEQ ID NO. 10:
MFLTRRDPPLSSFWTKVQYQRLKELNASGEQLEMGFSDALSRDRAFQGIEHQLMSQGKRHLEQLRTV

KHRPALLELEEKLAKALHQQGFVQVVTPTIITKSALAKMTIGEDHPLFSQVFWLDGKKCLRPMLAPNLY

TLWRELERLWDKPIRIFEIGTCYRKESQGAQHLNEFTMLNLTELGTPLEERHQRLEDMARWVLEAAGIRE

FELVTESSVVYGDTVDVMKGDLELASGAMGPHFLDEKWEIFDPWVGLGFGLERLLMIREGTQHVQS

MARSLSYLDGVRLNIN

>D. acetoxidans/1-277
Desulfotomaculum acetoxidans DSM 771
VERSION YP_003189614.1 GI: 258513392
SEQ ID NO. 11:
MSFLWTVSQQKRLSELNASEEEKNMSFSSTSDREAAYKRVEMRLINESKQRLNKLRHETRPAICALENRL

AAALRGAGFVQVATPVILSKKLLGKMTITDEHALFSQVFWIEENKCLRPMLAPNLYYILKDLLRLWEKPV

RIFEIGSCFRKESQGSNHLNEFTMLNLVEWGLPEEQRQKRISELAKLVMDETGIDEYHLEHAESVVYGET

VDVMHRDIELGSGALGPHFLDGRWGVVGPWVGIGFGLERLLMVEQGGQNVRSMGKSLTYLDG

VRLNI

When the particular tRNA charging (aminoacylation) function has been provided by mutating the tRNA synthetase, then it may not be appropriate to simply use another wild-type tRNA sequence, for example one selected from the above. In this scenario, it will be important to preserve the same tRNA charging (aminoacylation) function. This is accomplished by transferring the mutation(s) in the exemplary tRNA synthetase into an alternate tRNA synthetase backbone, such as one selected from the above.

In this way it should be possible to transfer selected mutations to corresponding tRNA synthetase sequences such as corresponding pylS sequences from other organisms beyond exemplary *M. barkeri* and/or *M. mazei* sequences.

Target tRNA synthetase proteins/backbones, may be selected by alignment to known tRNA synthetases such as exemplary *M. barkeri* and/or *M. mazei* sequences.

This subject is now illustrated by reference to the pylS (pyrrolysine tRNA synthetase) sequences but the principles apply equally to the particular tRNA synthetase of interest.

For example, FIG. 6 provides an alignment of all PylS sequences. These can have a low overall % sequence identity. Thus it is important to study the sequence such as by aligning the sequence to known tRNA synthetases (rather than simply to use a low sequence identity score) to ensure that the sequence being used is indeed a tRNA synthetase.

Thus suitably when sequence identity is being considered, suitably it is considered across the tRNA synthetases as in FIG. 6. Suitably the % identity may be as defined from FIG. 6. FIG. 7 shows a diagram of sequence identities between the tRNA synthetases. Suitably the % identity may be as defined from FIG. 7.

It may be useful to focus on the catalytic region. FIG. 8 aligns just the catalytic regions. The aim of this is to provide a tRNA catalytic region from which a high % identity can be defined to capture/identify backbone scaffolds suitable for accepting mutations transplanted in order to produce the same tRNA charging (aminoacylation) function, for example new or unnatrual amino acid recognition.

Thus suitably when sequence identity is being considered, suitably it is considered across the catalytic region as in FIG. 8. Suitably the % identity may be as defined from FIG. 8. FIG. 9 shows a diagram of sequence identities between the catalytic regions. Suitably the % identity may be as defined from FIG. 9.

'Transferring' or 'transplanting' mutations onto an alternate tRNA synthetase backbone can be accomplished by site directed mutagenesis of a nucleotide sequence encoding the tRNA synthetase backbone. This technique is well known in the art. Essentially the backbone pylS sequence is selected (for example using the active site alignment discussed above) and the selected mutations are transferred to (i.e. made in) the corresponding/homologous positions.

When particular amino acid residues are referred to using numeric addresses, unless otherwise apparent, the numbering is taken using MbPylRS (*Methanosarcina barkeri* pyrrolysyl-tRNA synthetase) amino acid sequence as the reference sequence (i.e. as encoded by the publicly available wild type *Methanosarcina barkeri* PylS gene Accession number Q46E77).

SEQ ID NO. 12:
MDKKPLDVLI SATGLWMSRT GTLHKIKHYE VSRSKIYIEM

ACGDHLVVNN SRSCRTARAF RHHKYRKTCK RCRVSDEDIN

NFLTRSTEGK TSVKVKVVSA PKVKKAMPKS VSRAPKPLEN

PVSAKASTDT SRSVPSPAKS TPNSPVPTSA PAPSLTRSQL

DRVEALLSPE DKISLNIAKP FRELESELVT RRKNDFQRLY

TNDREDYLGK LERDITKFFV DRDFLEIKSP ILIPAEYVER

MGINNDTELS KQIFRVDKNL CLRPMLAPTL YNYLRKLDRI

LPDPIKIFEV GPCYRKESDG KEHLEEFTMV NFCQMGSGCT

RENLESLIKE FLDYLEIDFE IVGDSCMVYG DTLDIMHGDL

ELSSAVVGPV PLDREWGIDK PWIGAGFGLE RLLKVMHGFK

NIKRASRSES YYNGISTNL

This is to be used as is well understood in the art to locate the residue of interest. This is not always a strict counting exercise—attention must be paid to the context or alignment. For example, if the protein of interest is of a slightly different length, then location of the correct residue in that sequence corresponding to (for example) L266 may require the sequences to be aligned and the equivalent or corresponding residue picked, rather than simply taking the 266th residue of the sequence of interest. This is well within the ambit of the skilled reader.

Notation for mutations used herein is the standard in the art. For example L266M measns that the amino acid corresponding to L at position 266 of the wild type sequence is replaced with M.

The transplantation of mutations between alternate tRNA backbones is now illustrated with reference to exemplary *M. barkeri* and *M. mazei* sequences, but the same principles apply equally to transplantation onto or from other backbones.

For example Mb AcKRS is an engineered synthetase for the incorporation of AcK
Parental protein/backbone: *M. barkeri* PylS
Mutations: L266V, L270I, Y271F, L274A, C317F
Mb PCKRS: engineered synthetase for the incorporation of PCK
Parental protein/backbone: *M. barkeri* PylS
Mutations: M241F, A267S, Y271C, L274M Synthetases with the same substrate specificities can be obtained by transplanting these mutations into *M. mazei* PylS. The sequence homology of the two synthetases can be seen in FIG. 10. Thus the following synthetases may be generated by transplantation of the mutations from the Mb backbone onto the Mm tRNA backbone:
Mm AcKRS introducing mutations L301V, L305I, Y306F, L309A, C348F into *M. mazei* PylS, and
Mm PCKRS introducing mutations M276F, A302S, Y306C, L309M into *M. mazei* PylS.

Full length sequences of these exemplary transplanted mutation synthetases are given below.

>Mb_PyIS/1-419
SEQ ID NO. 13:
MDKKPLDVLISATGLWMSRTGTLHKIKHHEVSRSKIYIEMACGDHLVVNNSRSCRTARAFRHHKYRKTC

KRCRVSDEDINNFLTRSTESKNSVKVRVVSAPKVKKAMPKSVSRAPKPLENSVSAKASTNTSRSVPSPAK

STPNSSVPASAPAPSLTRSQLDRVEALLSPEDKISLNMAKPFRELEPELVTRRKNDFQRLYTNDREDYLGK

LERDITKFFVDRGFLEIKSPILIPAEYVERMGINNDTELSKQIFRVDKNLCLRPMLAPTLYNYLRKLDRILPGP

IKIFEVGPCYRKESDGKEHLEEFTMVNFCQMGSGCTRENLEALIKEFLDYLEIDFEIVGDSCMVYGDTL

DIMHGDLELSSAVVGPVSLDREWGIDKPWIGAGFGLERLLKVMHGFKNIKRASRSESYYNGISTNL

>Mb_AcKRS/1-419
SEQ ID NO. 14:
MDKKPLDVLISATGLWMSRIGTLHKIKHHEVSRSKIYIEMACGDHLVVNNSRSCRTARAFRHHKYRKTC

KRCRVSGEDINNFLTRSTESKNSVKVRVVSAPKVKKAMPKSVSRAPKPLENSVSAKASTNTSRSVPSPAK

STPNSSVPASAPAPSLTRSQLDRVEALLSPEDKISLNMAKPFRELEPELVTRRKNDFQRLYTNDREDYLGK

LERDITKFFVDRGFLEIKSPILIPAEYVERMGINNDTELSKQIFRVDKNLCLRPMVAPTIFNYARKLDRILPG

PIKIFEVGPCYRKESDGKEHLEEFTMVNFFQMGSGCTRENLEALIKEFLDYLEIDFEIVGDSCMVYGDTL

DIMHGDLELSSAVVGPVSLDREWGIDKPWIGAGFGLERLLKVMHGFKNIKRASRSESYYNGISTNL

>Mb_PCKRS/1-419
SEQ ID NO. 15:
MDKKPLDVLISATGLWMSRTGTLHKIKHHEVSRSKIYIEMACGDHLVVNNSRSCRTARAFRHHKYRKTC

KRCRVSDEDINNFLTRSTESKNSVKVRVVSAPKVKKAMPKSVSRAPKPLENSVSAKASTNTSRSVPSPAK

STPNSSVPASAPAPSLTRSQLDRVEALLSPEDKISLNMAKPFRELEPELVTRRKNDFQRLYTNDREDYLGK

LERDITKFFVDRGFLEIKSPILIPAEYVERFGINNDTELSKQIFRVDKNLCLRPMLSPTLCNYMRKLDRILPGP

IKIFEVGPCYRKESDGKEHLEEFTMVNFCQMGSGCTRENLEALIKEFLDYLEIDFEIVGDSCMVYGDTL

DIMHGDLELSSAVVGPVSLDREWGIDKPWIGAGFGLERLLKVMHGFKNIKRASRSESYYNGISTNL

>Mm_PylS/1-454
SEQ ID NO. 16:
MDKKPLNTLISATGLWMSRTGTIHKIKHHEVSRSKIYIEMACGDHLVVNNSRSSRTARALRHHKYRKTCK

RCRVSDEDLNKFLTKANEDQTSVKVKVVSAPTRTKKAMPKSVARAPKPLENTEAAQAQPSGSKFSPAI

PVSTQESVSVPASVSTSISSISTGATASALVKGNTNPITSMSAPVQASAPALTKSQTDRLEVLLNPKDEISL

NSGKPFRELESELLSRRKKDLQQIYAEERENYLGKLEREITRFFVDRGFLEIKSPILIPLEYIERMGIDNDTELS

KQIFRVDKNFCLRPMLAPNLYNYLRKLDRALPDPIKIFEIGPCYRKESDGKEHLEEFTMLNFCQMGSGC

TRENLESIITDFLNHLGIDFKIVGDSCMVYGDTLDVMHGDLELSSAVVGPIPLDREWGIDKPWIGAGF

GLERLLKVKHDFKNIKRAARSESYYNGISTNL

>Mm_AcKRS/1-454
SEQ ID NO. 17:
MDKKPLNTLISATGLWMSRTGTIHKIKHHEVSRSKIYIEMACGDHLVVNNSRSSRTARALRHHKYRKTCK

RCRVSDEDLNKFLTKANEDQTSVKVKVVSAPTRIKKAMPKSVARAPKPLENTEAAQAQPSGSKFSPAI

PVSTQESVSVPASVSTSISSISTGATASALVKGNTNPITSMSAPVQASAPALTKSQTDRLEVLLNPKDEISL

NSGKPFRELESELLSRRKKDLQQIYAEERENYLGKLEREITRFFVDRGFLEIKSPILIPLEYIERMGIDNDTELS

KQIFRVDKNFCLRPMVAPNIFNYARKLDRALPDPIKIFEIGPCYRKESDGKEHLEEFTMLNFFQMGSGC

TRENLESIITDFLNHLGIDFKIVGDSCMVYGDTLDVMHGDLELSSAVVGPIPLDREWGIDKPWIGAGF

GLERLLKVKHDFKNIKRAARSESYYNGISTNL

>Mm_PCKRS/1-454
SEQ ID NO. 18:
MDKKPLNTLISATGLWMSRTGTIHKIKHHEVSRSKIYIEMACGDHLVVNNSRSSRTARALRHHKYRKTCK

RCRVSDEDLNKFLTKANEDQTSVKVKVVSAPTRTKKAMPKSVARAPKPLENTEAAQAQPSGSKFSPAI

PVSTQESVSVPASVSTSISSISTGATASALVKGNTNPITSMSAPVQASAPALTKSQTDRLEVLLNPKDEISL

NSGKPFRELESELLSRRKKDLQQIYAEERENYLGKLEREITRFFVDRGFLEIKSPILIPLEYIERFGIDNDTELSK

QIFRVDKNFCLRPMLSPNLCNYMRKLDRALPDPIKIFEIGPCYRKESDGKEHLEEFTMLNFCQMGSGC

-continued

TRENLESIITDFLNHLGIDFKIVGDSCMVYGDTLDVMHGDLELSSAVVGPIPLDREWGIDKPWIGAGF

GLERLLKVKHDFKNIKRAARSESYYNGISTNL

The same principle applies equally to other mutations and/or to other backbones.

Transplanted polypeptides produced in this manner should advantageously be tested to ensure that the desired function/substrate specificities have been preserved.

Polynucleotides encoding the polypeptide of interest for the method described above can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the hotst cell. Suitable host cells include bacteria such as E. coli.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Vectors of the invention may be transformed or transfected into a suitable host cell as described to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicilin resistance gene in the case of a bacterial plasmid. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

Another aspect of the invention is a method, such as an in vitro method, of incorporating the BCN containing amino acid(s) genetically and site-specifically into the protein of choice, suitably in a eukaryotic cell. One advantage of incorporating genetically by said method is that it obviates the need to deliver the proteins comprising the BCN amino acid into a cell once formed, since in this embodiment they may be synthesised directly in the target cell. The method comprises the following steps:

i) introducing, or replacing a specific codon with, an orthogonal codon such as an amber codon at the desired site in the nucleotide sequence encoding the protein ii) introducing an expression system of orthogonal tRNA synthetase/tRNA pair in the cell, such as a pyrollysyl-tRNA synthetase/tRNA pair iii) growing the cells in a medium with the BCN containing amino acid acccording to the invention.

Step (i) entails or replacing a specific codon with an orthogonal codon such as an amber codon at the desired site in the genetic sequence of the protein. This can be achieved by simply introducing a construct, such as a plasmid, with the nucleotide sequence encoding the protein, wherein the site where the BCN containing amino acid is desired to be introduced/replaced is altered to comprise an orthogonal codon such as an amber codon. This is well within the person skilled in the art's ability and examples of such are given here below.

Step (iii) requires an orthogonal expression system to specifically incorporate the BCN containing amino acid at the desired location (e.g. the amber codon). Thus a specific orthogonal tRNA synthetase such as an orthogonal pyrollysyl-tRNA synthetase and a specific corresponding orthogonal tRNA pair which are together capable of charging said tRNA with the BCN containing amino acid are required. Examples of these are provided herein.

Protein Expression and Purification

Host cells comprising polynucleotides of the invention may be used to express proteins of the invention. Host cells may be cultrued under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the cultrue medium, for example dexamethasone or IPTG.

Proteins of the invention can be extracted from host cells by a variety of techniques known in the art, including enzymatic, chemical and/or osmotic lysis and physical disruption.

Proteins of the invention can be purified by standard techniques known in the art such as prepartative chromatography, affinity purification or any other suitable technique.

Definitions

The term 'comprises' (comprise, comprising) should be understood to ahve its normal meaning in the art, i.e. that the stated feature or group of features is included, but that the term does not exclude any other stated feature or group of featrues from also being present.

BRIEF DESCRIPTION OF THE FIGURES

The application contains at least one drawing executed in color. Copies of this patent or patent application publication with color drawings will be provided by the Office upon request and payment of the necessary fee.

FIG. 1 shows structural formulae of unnatural amino acids 1 to 5 and tetrazine derivatives (6-17) used in this study. TAMRA-X, Bodipy TMR-X, Bodipy-FL and CFDA are common names for fluorphores; their structural formulae are shown in FIG. 15).

FIG. 2 shows kinetic and spectrometric characterization of the BCN-tetrazine reaction. a) Stopped flow kinetics of the reaction; the inset shows the conjugation of tetrazine 7 to 5-narbornen-2-ol (Nor), note different timescales; conditions: $c_7$=0.05 mM, $c_{BCN}$=$c_{Nor}$=5 mM in MeOH/H$_2$O (55/45), 25° C. b) The second order rate constant k for the reaction of 7 and BCN. c) The fluorogenic reaction of 11 with BCN.

FIG. 3 shows efficient, genetically encoded incorporation of unnatural amino acids using the BCNRS/tRNA$_{CUA}$ or TCORS/tRNA$_{CUA}$ pair in E. coli. a) Amino acid dependent overexpression of sfGFP-His$_6$ bearing an amber codon at position 150. The expressed protein was detected in lysates using an anti-His$_6$ antibody, b) Coomassie stained gel showing purified proteins, c-e) Mass spectrometry of amino acid incorporation: sfGFP-1 -His$_6$, found: 28017.54 Da, calculated: 28017.62 Da; sfGFP-2-His$_6$, found: 27993.36 Da, calculated: 27992.82 Da; sfGFP-His$_6$ produced in the presence of 3, as described in the text, found: 28019.34 Da, calculated: 28019.63 Da. Smaller grey peaks in all mass spectra denote a loss of 131 Da, which corresponds to the proteolytic cleavage of the N-terminal Methionine.

FIG. 4 shows rapid and specific labeling of recombinant proteins with tetrazine -fluorophores. a) Specific labeling of sfGFP bearing 1, 2 and 4 with tetrazine-dye conjugate 11 (10 eq) demonstrated by SDS-PAGE and in-gel fluorescence. For sfGFP-His$_6$ produced in the presence of 3 only very faint, sub-stoichiometric labeling is visible, b) Quantitative labeling of sfGFP-1 with 11 demonstrated by ESI-MS (before bioconjugation (blue spectrum, found: 28018.1±2 Da, calculated: 28017.6 Da) and after bioconjugation (red spectrum, found 28824.2±2 Da, calculated: 28823.2 Da)), c) Quantitative labeling of sfGFP-2 with 11 demonstrated by ESI-MS (before bioconjugation (blue spectrum, found: 27993.2±2 Da, calculated: 27992.8 Da) and after bioconjugation (red spectrum, found 28799.4±2 Da, calculated: 28799.1 Da). d) No labeling of sfGFP-His4 (expressed in the presence of 3) with 11 could be detected by MS. e) Very rapid labeling of proteins containing site-specifically incorporated amino acid 1 and 2. sfGFP-1 (left) and sfGFP-2 (middle) are quantitatively labeled with 11 in the few seconds it takes to load the gel while it takes 1 h to completely label sfGFP-4 under the same conditions (right).

FIG. 5 shows site specific incorporation of 1 and 2 into proteins in mammalian cells and the rapid and specific labeling of cell surface and intracellular mammalian proteins with 11. a) Western blots demonstrate that the expression of full length mCherry(TAG)eGFP -HA is dependent on the presence of 1 or 2 and tRNA$_{CUA}$. BCNRS, TCORS are FLAG tagged, b) Specific and ultra-rapid labeling of a cell surface protein in live mammalian cells. EGFR-GFP bearing 1, 2 or 5 at position 128 is visible as green fluorescence at the membrane of transfected cells (left panels). Treatment of cells with 11 (400 nM) leads to selective labeling of EGFR that contains 1 or 2 (middle panels). Right panels show merged green and red fluorescence images, DIC=differential interference contrast. Cells were imaged 2 minutes after the addition of 11. c) Specific and rapid labeling of a nuclear protein in live mammalian cells. Jun-l-mCherry is visible as red fluorescence in the nuclei of transfected cells (left panels). Treatment of cells with the cell permeable tetrazine dye 17 (200 nM) leads to selective labeling of jun-l-mCherry (middle panel). Right panels show merged red and green fluorescence. No labeling was observed for cells bearing jun-5-mCherry.

FIG. 11 shows scheme 1. We demonstrate the synthesis, genetic encoding and fluorogenic labeling of unnatural amino acids 1 and 2 in vitro, in E. coli and in mammalian cells.

FIG. 12 shows LC/MS traces (254 nm) showing the formation of pyridazine products (6-BCN, 7-BCN, 9-BCN, 8-BCN) from reaction of the corresponding tetrazines (6, 7, 9 and 8) with 2 equivalents of BCN (exo/endo mixture~4/1) in MeOH. All masses are given in Daltons. The HPLC traces were taken after incubating the reactions for 10 to 30 minutes at room temperature. The overall yield for conversion to pyridazine products was >98%.

FIG. 13 shows determination of rate constants k for the reaction of various tetrazines with BCN by UV-spectroscopy using a stopped-flow device. (a) Response of the UV absorbance at 320 nm of compound 6 upon BCN addition (100 eq=5 mM); by fitting the data to a single exponential equation, k' values were determined (left panel); each measurement was carried out three to five times and the mean of the observed rates k' was plotted against the concentration of BCN to obtain the rate constant k from the slope of the plot. For all four tetrazines complete measurement sets were done in duplicate (middle and right panel) and the mean of values is reported in Supplementary Table 1. (b-d) same as (a) for tetrazines 7, 9 and 8. Conditions: $c_{tetrazine}$=0.05 mM in 9/1 H$_2$O/MeOH, $c_{BCN}$=0.5 to 5 mM in MeOH, resulting in a final 55/45 MeOH/H$_2$O mixture. All experiments were recorded at 25° C.

FIG. 14 shows determination of rate constants k for the reaction of tetrazines 6 and 7 with TCO by UV-spectroscopy using a stopped-flow device. (a) Response of the UV absorbance at 320 nm of compound 6 upon TCO addition (100eq=5 mM); by fitting the data to the sum of two single exponential equations, k' values for the fast single exponential equations were determined (left panel); each measurement was carried out three to five times and observed rates k' were plotted against the concentration of TCO to obtain the rate constant k from the slope of the plot. For both tetrazines complete measurement sets were done at least in duplicate (middle and right panel) and the mean of values is reported in Supplementary Table 1. (b) same as (a) for tetrazine 7. Conditions: $c_{tetrazine}$=0.05 mM in 9/1 H$_2$O/MeOH, $c_{TCO}$=0.5 to 5 mM in MeOH, resulting in a final 55/45 MeOH/H$_2$O mixture. All experiments were recorded at 25° C.

FIG. 15 shows structural formulae of various tetrazine-fluorophores used in this study. Details on synthesis and characterization of these tetrazine-fluorophores can be found in reference 2.

FIG. 16 shows "Turn on" fluorescence of tetrazine-fluorophores upon reaction with 9-hydroxymethylbicyclo[6.1.0]nonyne (BCN). A 2 microM solution of the corresponding tetrazine-fluorophore in water (2 mM in DMSO) was reacted with 300 equivalents of BCN. Emission spectra were recorded before and 30 min after the addition of BCN. Excitation wavelengths: TAMRA-dyes and Bodipy-TMR-X: 550 nm; Bodipy-FL: 490 nm.

FIG. 17 shows amino acid dependent expression of sfGFP-His$_6$ bearing an amber codon at position 150. The expressed protein was detected in lysates using an anti-His$_6$ antibody. Using purified exo or endo diastereomers of amino acid 1 demonstrated that the exo form is preferentially incorporated into sfGFP by BCNRS/tRNA$_{CUA}$.

FIG. 18 shows LC-MS characterization of the labelling reaction of sfGFP-1 with various tetrazines. Black peaks denote the found mass of sfGFP-1 before labelling, colored peaks the found masses after reaction of sfGFP-1 with 6, 7, 9 and 8. All masses are given in Daltons. Labelling with all tetrazines is specific and quantitative. Reaction conditions: to a ~10 M solution of sfGFP-1 (in 20 mM Tris-HCl, 100 mM NaCl, 2 mM EDTA, pH 7.4) 10 equivalents of the corresponding tetrazine (1 mM stock solution in methanol) were added and the reaction mixture incubated for 10 to 30 minutes at room temperature.

FIG. 19 shows LC-MS shows specific and quantitative labelling of sfGFP-1 with tetrazine fluorophore conjugates 12, 16, 13 and 14. Red peaks denote the found mass of sfGFP-1 before labelling, colored peaks the found masses after reaction of sfGFP-1 with 12 (a), 16 (b), 13 (c) and 14 (d). Expected and found mass values are given in Daltons. Labelling with all tetrazine-fluorophores is specific and quantitative. Reaction conditions: to a ~10 M solution of sfGFP-1 (in 20 mM Tris-HCl, 100 mM NaCl, 2mM EDTA, pH 7.4) 10 equivalents of the corresponding tetrazine dye (2 mM stock solution in DMSO) were added and the reaction mixture incubated for 10 to 30 minutes at room temperature.

FIG. 20 shows specificity of labeling 1 and 2 in sfGFP versus the E. coli proteome. The coomassie stained gel shows proteins from E. coli producing sfGFP in the presence of the indicated concentration of unnatural amino acids 1, 2, 3 (both exo and endo diastereomers) and 5. In gel fluorescence gels show specific labeling with tetrazine-dye conjugate 11. Though amino acids 1, 2 and 3-exo are incorporated at a similar level (as judged from coomassie stained gels and western blots), we observe only very faint, sub-stoichiometric labeling of sfGFP produced in the presence of 3-exo and 3-endo. These observations are consistent with the in vivo conversion of a fraction of the trans-alkene in 3 to its cis-isomer.

FIG. 21 shows specificity of labeling 1 in sfGFP versus the E. coli proteome. Lanes 1-5: Coomassie stained gel showing proteins from E. coli producing sfGFP in the presence of the indicated concentration of unnatural amino acids 1 and 5. Lanes 6-10: The expressed protein was detected in lysates using an anti-His6 antibody. Lanes 11-15: fluorescence images of protein labeled with the indicated fluorophore 11.

FIG. 22 shows specific and ultra-rapid labelling of EGFR-GFP with tetrazine-fluorophore conjugate 11 for 2 minutes. EGFR-GFP bearing 1 at position 128 is visible as green fluorescence at the membrane of transfected cells (left panels). Treatments of cells with 11 (400 nM) leads to selective labelling of EGFR-GFP containing 1 (middle panels). Right panels show merged green and red fluorescence images, DIC=differential interference contrast. Cells were imaged 2 minutes after addition of 11. No labelling was observed for cells in the same sample that did not express EGFR-GFP, and cells bearing EGFR-5-GFP were not labeled with 11.

FIG. 23 shows specific and ultra-rapid labelling of EGFR-GFP with tetrazine-fluorophore conjugate 11 for 5 minutes. EGFR-GFP bearing 1 at position 128 is visible as green fluorescence at the membrane of transfected cells (left panels). Treatments of cells with 11 (400 nM) leads to selective labelling of EGFR-GFP containing 1 (middle panels). Right panels show merged green and red fluorescence images, DIC=differential interference contrast. Cells were imaged 5 minutes after addition of 11. No labelling was observed for cells in the same sample that did not express EGFR-GFP, and cells bearing EGFR-5-GFP were not labeled with 11.

FIG. 24 shows specific and ultra-rapid labelling of EGFR-GFP with tetrazine-fluorophore conjugate 11 for 10 minutes. EGFR-GFP bearing 1 at position 128 is visible as green fluorescence at the membrane of transfected cells (left panels). Treatments of cells with 11 (400 nM) leads to selective labelling of EGFR-GFP containing 1 (middle panels). Right panels show merged green and red fluorescence images, DIC=differential interference contrast. Cells were imaged 10 minutes after addition of 11. No labelling was observed for cells in the same sample that did not express EGFR-GFP, and cells bearing EGFR-5-GFP were not labeled with 11.

FIG. 25 shows that in contrast to the ultra-rapid labelling of EGFR-GFP containing amino acid 1, it took 2 hours to specifically label cells bearing EGFR-4-GFP with tetrazine-fluorophore conjugate 11.[2]

Figure 6:
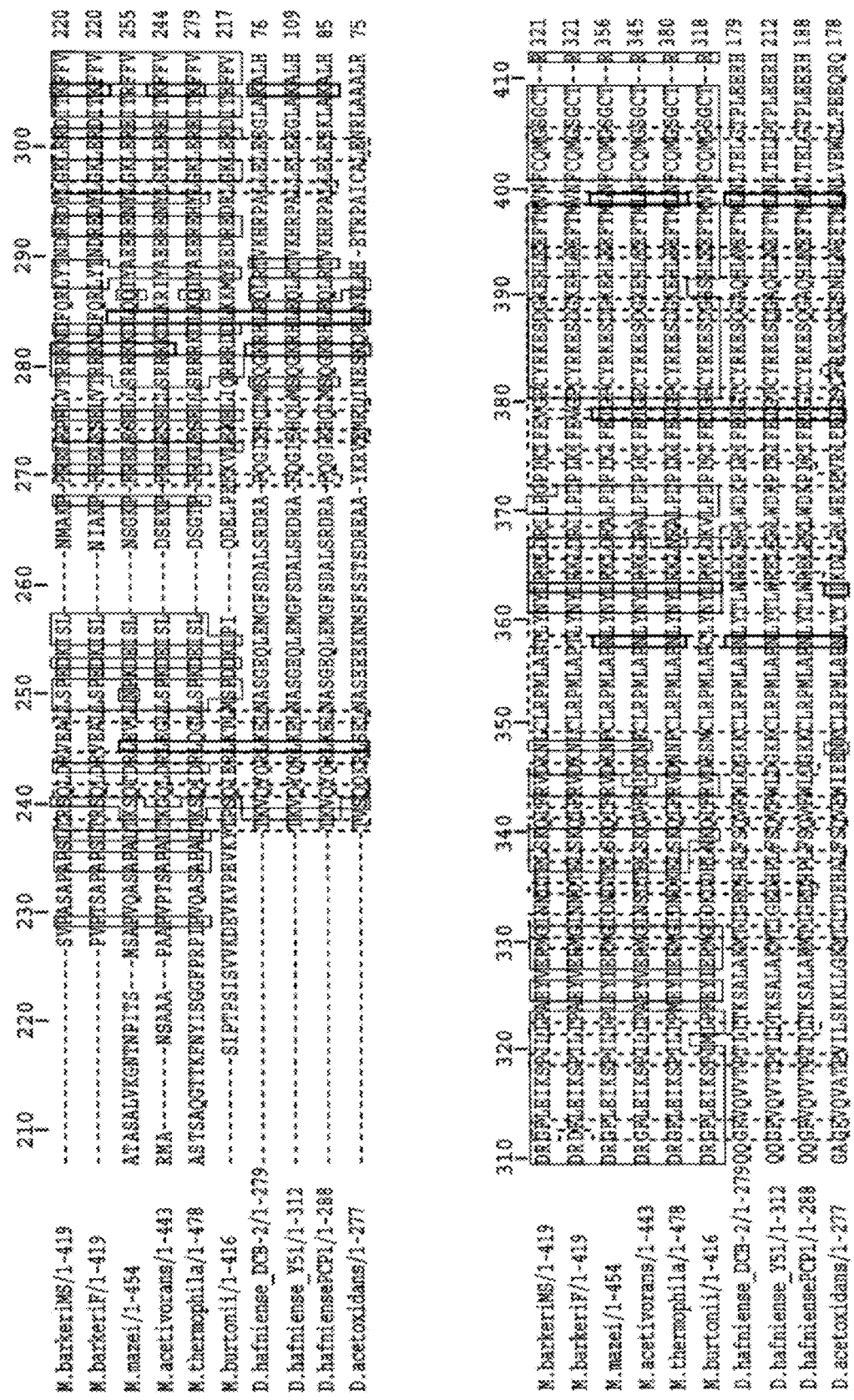
FIG. 6 shows alignment of PylS sequences.
Figure 7:
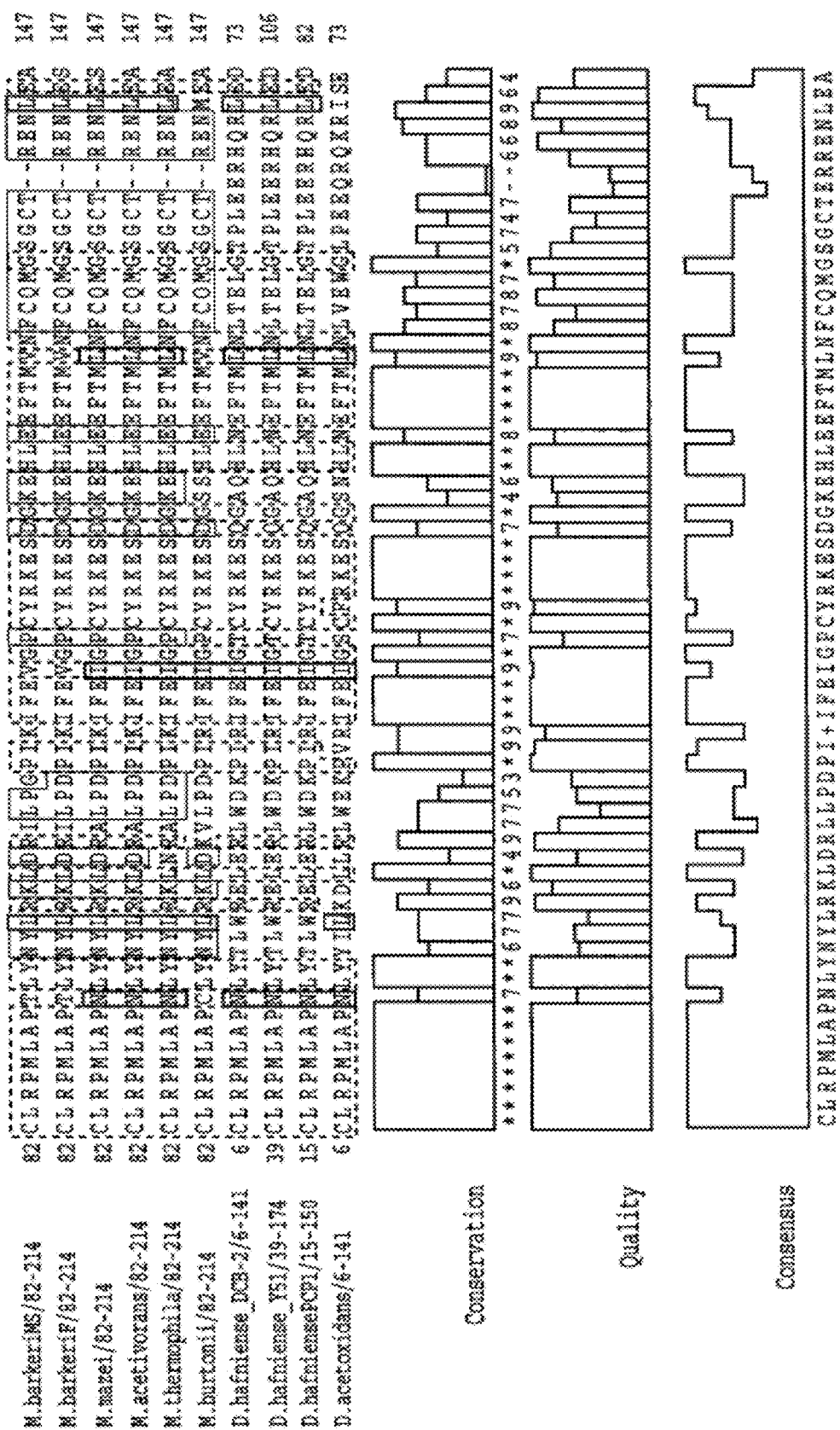
FIG. 7 shows sequence identity of PylS sequences.
Figure 8:
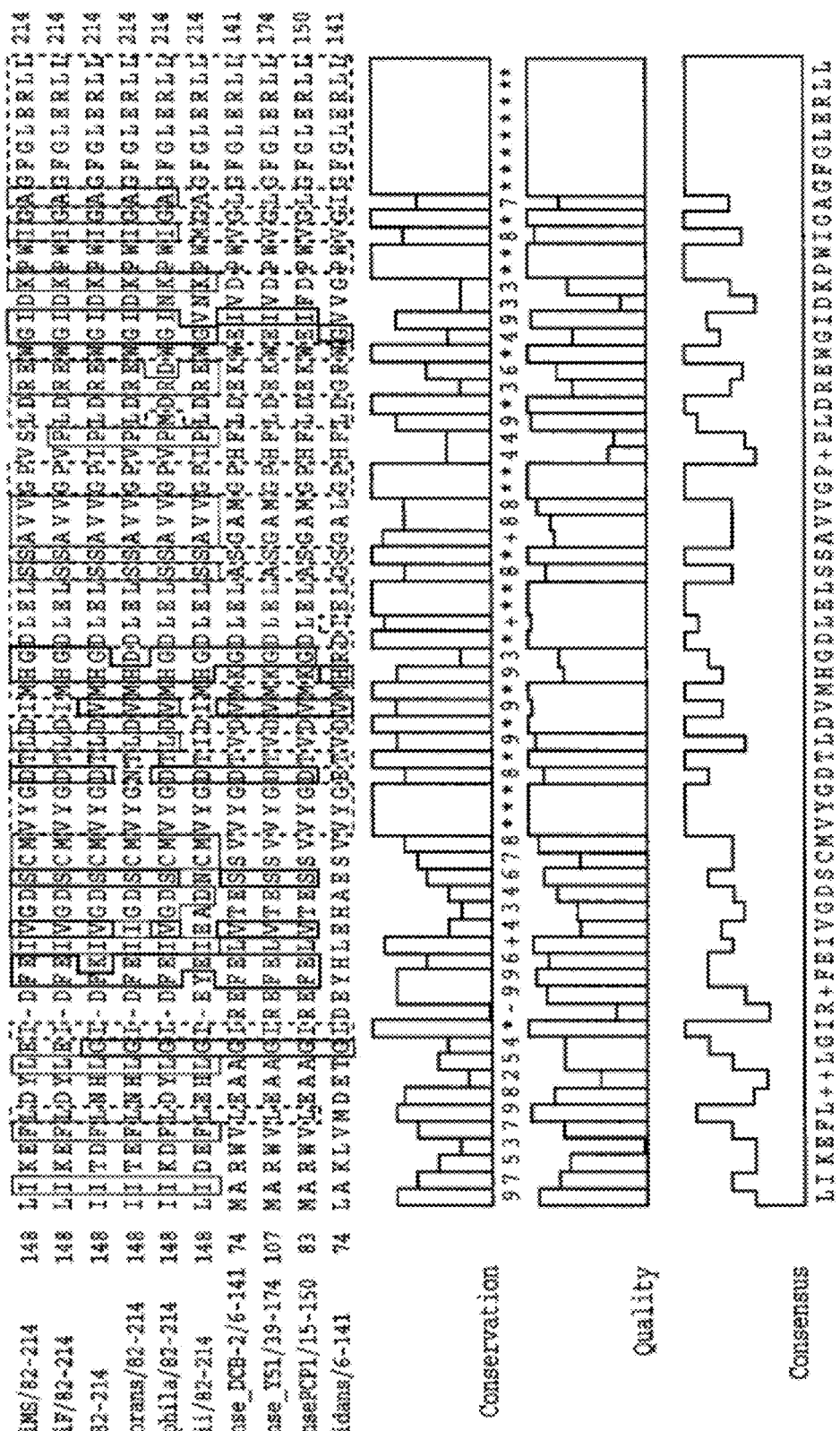
FIG. 8 shows alignment of the catalytic domain of PylS sequences (from 350 to 480; numbering from alignment of FIG. 6).
Figure 9:
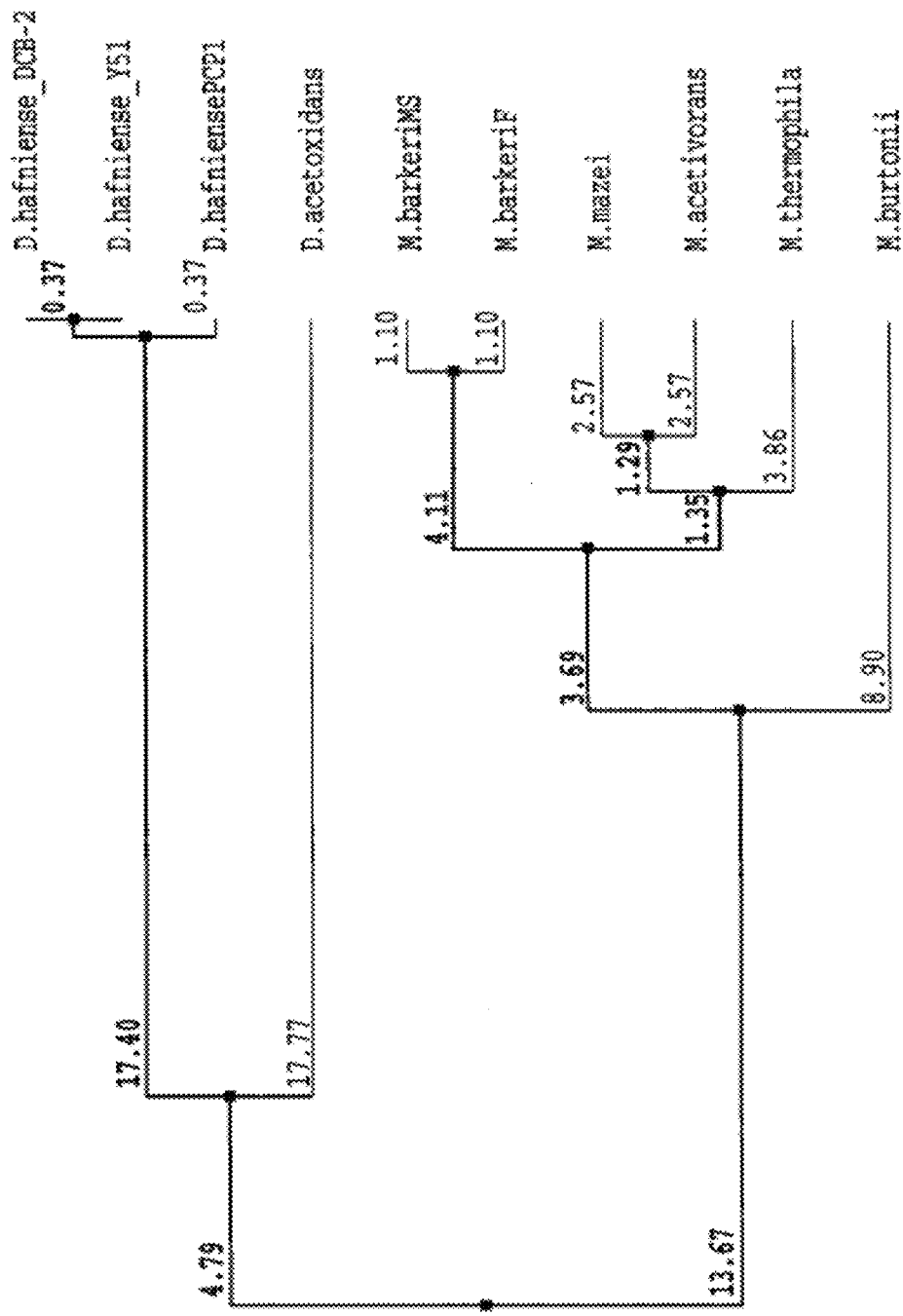
FIG. 9 shows sequence identity of the catalytic domains of PylS sequences.
Figure 10:
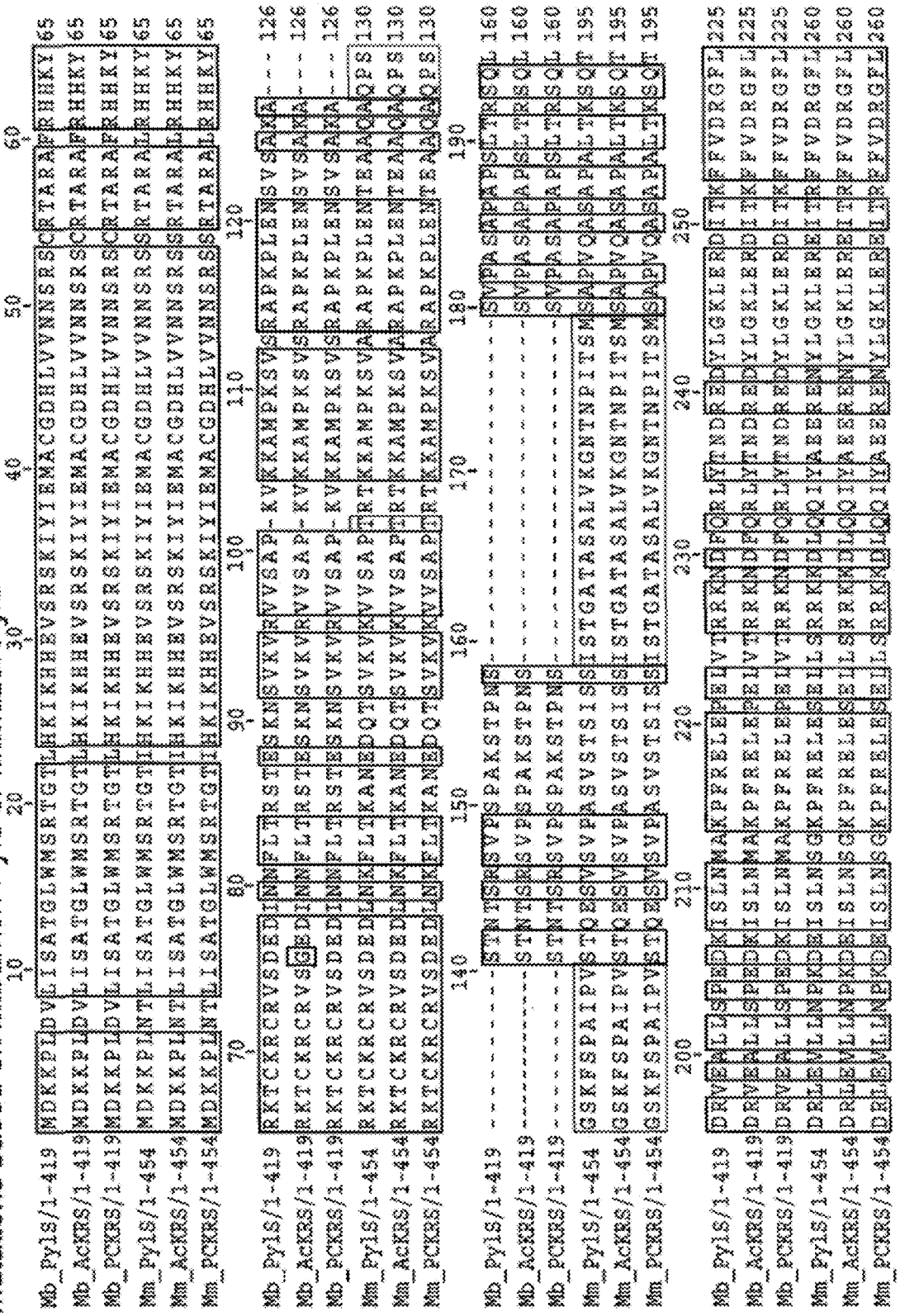
FIG. 10 shows alignment of synthetases with transplanted mutations based on M. barkeri PylS or M. mazei PylS. The red asterisks indicate the mutated positions.

EGFR-GFP bearing 4 at position 128 is visible as green fluorescence at the membrane of transfected cells (left panels). Treatments of cells with 11 (200 nM) leads to labelling of EGFR-GFP containing 4 (middle panels). Right panels show merged green and red fluorescence images, DIC=differential interference contrast. Cells were imaged 2 hours after addition of 11.

FIG. 26 shows specific and ultra-rapid labelling of EGFR-GFP with tetrazine-fluorophore conjugate 11 for 2 minutes. EGFR-GFP bearing 2 at position 128 is visible as green fluorescence at the membrane of transfected cells (left panels). Treatments of cells with 11 (400 nM) leads to selective labelling of EGFR-GFP containing 2 (middle panels). Right panels show merged green and red fluorescence images, DIC=differential interference contrast. Cells were imaged 2 minutes after addition of 11. No labelling was observed for cells in the same sample that did not express EGFR-GFP, and cells bearing EGFR-5-GFP were not labeled with 11.

FIG. 27 shows specific and ultra-rapid labelling of EGFR-GFP with tetrazine-fluorophore conjugate 11 for 5 minutes. EGFR-GFP bearing 2 at position 128 is visible as green fluorescence at the membrane of transfected cells (left panels). Treatments of cells with 11 (400 nM) leads to selective labelling of EGFR-GFP containing 2 (middle panels). Right panels show merged green and red fluorescence images, DIC=differential interference contrast. Cells were imaged 5 minutes after addition of 11. No labelling was observed for cells in the same sample that did not express EGFR-GFP, and cells bearing EGFR-5-GFP were not labeled with 11.

FIG. 28 shows site specific incorporation of 3 in mammalian cells and the labeling of EGFR-GFP wilh tetrazine-fluorophore conjugate 11 for 30 and 60 minutes, a) Western blots demonstrate that the expression of full length mCherry (TAG)eGFP-HA is dependent on the presence of 3 or 5 and tRNA$_{CUA}$. BCNRS and PylRS are FLAG tagged. b and c) EGFR-GFP in the presence 3 at position 128 is visible as green fluorescence at the membrane of transfected cells (left panels). Treatments of cells with 11 (400 nM) leads to faint, but measurable labelling of EGFR-GFP containing 3 (middle panels) This observation is consistent with the isomerization of the trans-alkene bond to its cis form of a fraction of 3 in mammalian cells. Right panels show merged green and red fluorescence images, DIC=differential interference contrast. Cells were imaged 30 or 60 minutes after addition of 11. No labelling was observed for cells in the same sample that did not express EGFR-GFP.

FIG. 29 shows specific and ultra-rapid labelling of a nuclear protein in live mammalian cells. Jun-1-mCherry is visible as red fluorescence in the nuclei of transfected cells (left panels). Treatment of cells with the cell permeable tetrazine dye 17 (200 nM) leads to selective labeling of jun-1-mCherry (middle panel). Right panels show merged red and green fluorescence. DIC=differential interference contrast. Cells were imaged 15 minutes after addition of 11. No labelling was observed for cells in the same sample that did not express jun-mCherry, and cells bearing jun-5-mCherry were not labeled with 11

The invention is now described by way of example. These examples are intended to be illustrative, and are not intended to limit the appended claims.

EXAMPLES

Here we develop a rapid and fluorogenic reaction between tetrazines and BCN and demonstrate the genetic encoding of both BCN and transcyclooctene containing amino acids 1 and 2 in *E. coli* and mammalian cells. We show the specific and rapid labeling of proteins in *E. coli* and in live mammalian cells with tetrazine probes, and explicitly demonstrate the advantages of the approach with respect to previously reported bioorthogonal labeling strategies (FIG. 11—Scheme 1).

Example 1

Chemistry and Addition Reactions

The rate constants for the reactions of various dienophiles (BCN, TCO (trans-cyclooctene -4-ol) and sTCO (bicyclo [6.1.0]non-4-ene-9-ylmethanol)) with tetrazines have been determined[3-5,9,11]. However, in many cases, researchers have used different tetrazines, solvent systems or measurement methods making it challenging to quantitatively compare the reactivity of each dienophile with tetrazines of interest. Our initial experiments confirmed that the rates for the reactions of each dienophile with tetrazine 6 (FIG. 1) were too fast to study by manual mixing under pseudo first order conditions. We therefore turned to stopped-flow techniques to directly determine the pseudo first order rate constants for these reactions. By following the exponential decay in absorbance at 320 nm upon reaction with a 10- to 100-fold excess of BCN in a methanol/water (55/45) mixture we determined the rate constants for the reaction of BCN with 6 and 7 as 437 $M^{-1}s^{-1}$ (+/−13) and 1245 $M^{-1}s^{-1}$ (+/−45), respectively. LC-MS and NMR confirm the formation of the expected products (Supplementary Information and FIG. 12). Under the same conditions we determined the rate constant of TCO with 6 and 7 as 5235 $M^1s^1$ (+/−258) and 17248 $M^1s^1$ (+/−3132) repectively. These data demonstrate that the reaction between BCN and 6 is approximately 1000 times faster than the reaction between 5-norbomene-2-ol and 6[7], while the TCO rate is approximately 10-15 times faster than the BCN rate. The sTCO rate was too fast to be measured accurately by stopped flow techniques and we estimate that it is at least 50 times faster than the TCO rate. Similar rate accelerations were observed for the reaction of BCN with tetrazines 8 and 9 (FIG. 1, FIG. 2a and 2b, Supplementary Table 1 and FIG. 13 and 14).

SUPPLEMENTARY TABLE 1

Rate constants k for the reaction of various tetrazines (6, 7, 9 and 8) with BCN and TCO at 25° C. measured under pseudo first order conditions using a stopped-flow device in comparison to rate constants for the reaction of the same tetrazines with 5-norbornene-2-ol at 21° C.[2] Values were determined from at least two independent measurements. Solvent system: 55/45 methanol/water. The cycloaddition reaction of BCN to tetrazines is 500 to 1000 times faster than the one of 5-norbornene-2-ol, the reaction between TCO and tetrazines is 10 to 15 times faster than the one between BCN and tetrazines.

| Tetrazine | BCN $k_2$ $[M^{-1}s^{-2}]^a$ | Nor $k_2$ $[M^{-1}s^{-2}]^a$ | TCO $k_2$ $[M^{-1}s^{-2}]^a$ |
|---|---|---|---|
| 6 | 437 ± 13 | 0.47 ± 0.0069 | 5235 ± 258 |
| 7 | 1245 ± 45 | 1.70 ± 0.048 | 17248 ± 3132 |
| 9 | 80 | 0.15 | n.d. |
| 8 | 2672 ± 95 | 5.00 ± 0.096 | n.d. |

Several tetrazine fluorophore conjugates, including 11, 13, 14 and 16 (FIG. 1, FIG. 15) are substantially quenched with respect to the free fluorophore, an observation that results from energy transfer of the fluorophore's emission to a proximal tetrazine chromophore with an absorption maximum between 510 and 530 nm[7,18]. We find that the reaction of BCN with tetrazine fluorophore conjugates 11, 13, 14 and 16 leads to a 5-10 fold increase in fluorescence, suggesting that the formation of the pyridazine product efficiently relieves fluorophore quenching (FIG. 2c and FIG. 16). The fluorogenic reaction between BCN and these tetrazines, like the reaction between strained alkenes and these tetrazines[7,18], is advantageous for imaging experiments since it maximizes the labeling signal while minimizing fluorescence arising from the free tetrazine fluorophore.

Example 2

Amino Acid Design

Next, we aimed to design, synthesize and genetically encode amino acids bearing BCN, TCO and sTCO for site-specific protein labeling with a diverse range of probes both in vitro and in cells. The Pyrrolysyl-tRNA synthetase (PylRS)/tRNA$_{CUA}$ pairs from *Methanosarcina* species, including *M. barkeri* (Mb) and *M. mazei* (Mm), and their evolved derivatives have been used to direct the site-specific incorporation of a growing list of structurally diverse unnatural amino acids in response to the amber codon[19-26]. The PylRS/tRNA$_{CUA}$ pair is emerging as perhaps the most versatile system for incorporating unnatural amino acids into proteins since it is orthogonal in a range of hosts, allowing synthetases evolved in *E. coli* to be used for genetic code expansion in a growing list of cells and organisms, including: *E. coli*, *Salmonella typhimurium*, yeast, human cells and *C. elegans*[7,27-31]. We designed the unnatural amino adds 1, 2 and 3 (FIG. 1) with the goal of incorporating them into proteins using the PylRS/tRNA$_{CUA}$ pair or an evolved derivative. The amino acids were synthesized as described in the Supplementary Information.

Example 3

Genetic Incorporation into Polypeptides and tRNA Synthetases

We screened the MbPylRS/tRNA$_{CUA}$ pair along with a panel of mutants of MbPylRS, previously generated in our laboratory for the site-specific incorporation of diverse unnatural amino acids into proteins, for their ability to direct the incorporation of 1, 2 and 3 in response to an amber codon introduced at position 150 in a C-terminally hexahistidine—(His$_6$) tagged superfolder green fluorescent protein (sfGFP). The MbPylRS/tRNA$_{CUA}$ pair did not direct the incorporation of any of the unnatural amino acids tested, as judged by western blot against the C-terminal His$_6$ tag. However, cells containing a mutant of MbPylRS, containing three amino acid substitutions Y271M, L274G, C313A[32] in the enzyme active site (which we named BCN-tRNA synthetase, BCNRS), and a plasmid that encodes MbtRNA$_{CUA}$ and sfGFP-His$_6$ with an amber codon at position 150 (psfGFP150TAGPylT-His$_6$) led to amino acid dependent synthesis of full length sfGFP-His$_6$, as judged by anti-His$_6$ western blot and coomassie staining (FIG. 3a). Additional protein expression experiments using 1, and its endo isomer demonstrated that the exo form is preferentially incorporated into proteins by BCNRS/tRNA$_{CUA}$ (FIG. 17). We found an additional synthetase mutant, bearing the mutations Y271A, L274M and C313A[32], which we named TCO-tRNA synthetase, TCORS. The TCORS/tRNA$_{CUA}$ pair led to amino acid dependent synthesis of sfGFP from psfGFP150TAGPylT-His$_6$ in the presence of 2. Finally we found that both the BCNRS/tRNA$_{CUA}$ pair as well as the TCORS/tRNA$_{CUA}$ pair led to amino acid dependent synthesis of sfGFP from psfGFP150TAGPylT-His$_6$ in the presence of 3. For each amino acid sfGFP was isolated in good yield after His-tag and gel filtration purification (6-12 mg per L of culture, FIG. 3b). This is comparable to the yields obtained for other well -incorporated unnatural amino acids, including 5. Electrospray ionization mass spectrometry (ESI-MS) of sfGFP produced from psfGFP150TAGPylT-His$_6$ in the presence of each unnatural amino acid is consistent with their site-specific incorporation (FIG. 3c-3e).

Example 4

Site-Specific Incorporation

To demonstrate that the tetrazine-dye-probes react efficiently and specifically with recombinant proteins that bear site-specifically incorporated 1 we labeled purified sfGFP-1-His$_6$ with 10 equivalents of tetrazine fluorophore conjugate 11 for 1 hour at room temperature. SDS-page and ESI-MS analysis confirmed quantitative labeling of sfGFP containing 1 (FIG. 4a and 4b). Control experiments demonstrated that sfGFP-4 is labeled under the same conditions used to label sfGFP-1, and that no non-specific labeling is detected with sfGFP-5. ESI-MS demonstrates that sfGFP-1 can be efficiently and specifically derivatized with a range of tetrazines 6, 7, 8 and 9 (FIG. 18), and with tetrazine fluorophore conjugates 12, 13, 14 and 16 (FIG. 19). We also demonstrated that purified sfGFP-2-His$_6$ can be quantitatively labeled with tetrazine fluorophore 11 (FIG. 4a and 4c). Interestingly we observe only very faint labeling of sfGFP-His$_6$ purified from cells expressing the TCORS/tRNA$_{CUA}$ and psfGFP150TAGPylT-His$_6$ and grown in the presence of 3 (FIG. 4a and 4d) and sub-stoichiometric labeling of this protein prior to purification (FIG. 20). Since the sfGFP expressed in the presence of 3 has a mass corresponding to the incorporation of 3, these observations are consistent with the in vivo conversion of a fraction of the trans-alkene in 3 to its unreactive cis isomer. This isomerization is known to occur in the presence of thiols[4].

Example 5

Specificity and Selectivity of Reactions

To further demonstrate that the reaction between BCN and various tetrazine-based dyes is not only highly efficient and specific, but also highly selective within a cellular context, we performed the reaction on E. coli expressing sfGFP-1-His$_6$ (FIG. 21). Cells expressing sfGFP-1 at a range of levels (controlled by adjusting the concentration of 1 added to cells) were harvested 4 hours after induction of protein expression, washed with PBS and incubated with tetrazine dye 11 for 30 min at room temperature. After adding an excess of BCN in order to quench non-reacted tetrazine-dye, the cells were lysed and the reaction mixtures were analyzed. In-gel fluorescence demonstrated specific labeling of recombinant sfGFP bearing 1 with tetrazine-conjugated TAMRA dye 11. While many proteins in the lysates were present at a comparable abundance to sfGFP-1 we observe very little background labeling, suggesting that the reaction is specific with respect to the E. coli proteome.

Example 6

Speed of Labelling

To investigate whether the rate of reaction for the BCN- and TCO-tetrazine cycloadditions observed on small molecules translates into exceptionally rapid protein labeling we compared the labeling of purified sfGFP bearing 1, 2 or 4 with 10 equivalents of tetrazine-fluorophore conjugate 11. In-gel fluorescence imaging of the labeling reaction as a function of time (FIG. 4e) indicates that the reaction of sfGFP-4 reaches completion in approximately 1 h. In contrast the labeling of sfGFP-1 and sfGFP-2 was complete within the few seconds it took to measure the first time point, demonstrating that the rate acceleration of the BCN- and TCO-tetrazine reaction translates into much more rapid protein labeling.

Example 7

Application to Mammalian Cells

To demonstrate the incorporation of amino acids 1 and 2 in mammalian cells we created mammalian optimized versions of BCNRS and TCORS by transplanting the mutations that allow the incorporation of 1 or 2 into a mammalian optimized MbPylRS. By western blot we demonstrated that both 1 and 2 can be genetically encoded with high efficiency into proteins in mammalian cells using the BCNRS/tRNA$_{CUA}$ pair or TCORS/tRNA$_{CUA}$ (FIG. 5a).

To investigate whether the rapid BCN-tetrazine ligation provides advantages for site -specifically labeling proteins on mammalian cells we expressed an epidermal growth factor receptor (EGFR)—green fluorescent protein (GFP) fusion bearing an amber codon at position 128 (EGFR (128TAG)GFP) in HEK-293 cells containing the BCNRS/tRNA$_{CUA}$ pair, cultured in the presence of 1 (0.5 mM). Full-length EGFR-1-GFP was produced in the presence of 1 resulting in bright green fluorescence at the cell membrane. To label 1 at position 128 of EGFR, which is on the extracellular domain of the receptor, with tetrazine -fluorophore conjugates we incubated cells with 11 (400 nM), changed the media and imaged the red fluorescence arising from TAMRA labeling as well as the green fluorescence arising from expression of full-length EGFR-GFP. TAMRA fluorescence co-localized nicely with cell-surface EGFR-GFP fluorescence. Clear labeling of cells that bear EGFR-1-GFP was observed within 2 minutes, the first time point we could measure; additional time points demonstrated that labeling was saturated within 2 minutes (FIG. 5b and FIGS. 22-25); similar results were obtained with tetrazine fluorophore 12. Incorporation of 2 into the EGFR-GFP fusion led to similarly rapid and efficient labeling with tetrazine fluorophore 11 (FIG. 5b and FIGS. 26-27). In contrast it took 2 hours before we observed any specific labeling of cells bearing EGFR-4-GFP under identical conditions (FIG. 25)[7]. In control experiments we observed no labeling for cells bearing EGFR-5-GFP and no non-specific labeling was detected for cells that did not express EGFR-GFP. We observe weak but measureable labeling of EGFR-GFP expressed in HEK 293 cells from (EGFR(128TAG)GFP) in the presence of the BCNRS/tRNA$_{CUA}$ pair and 3 (FIG. 28). These observations are consistent with the isomerization of a fraction of 3 in mammalian cells, and with our observations in E. coli.

To demonstrate the rapid labeling of an intracellular protein in mammalian cells we expressed a transcription factor, jun, with a C-terminal mCherry fusion from a gene bearing an amber codon in the linker between JunB (jun) and mCherry. In the presence of amino acid 1 and the BCNKRS/tRNA$_{CUA}$ pair the jun-1-mCherry protein was produced in HEK cells and, as expected, localized to the nuclei of cells (FIG. 5c and FIG. 29). Labeling with a cell permeable diacetyl fluorescein tetrazine conjugate (200 nM) resulted in green fluorescence that co-localizes nicely with the mCherry signal at the first time point analyzed (15 min labeling followed by 90 min washing). No specific labeling was observed in non-transfected cells in the same sample or in control cells expressing jun-5-mCherry, further confirming the specificity of intracellular labeling.

Supplementary Examples

Protein Expression and Purification

To express sfGFP with incorporated unnatural amino acid 1, we transformed E. coli DH10B cells with pBKBCNRS (which encodes MbBCNRS) and psfGFP150TAGPylT-His$_6$ (which encodes MbtRNA$_{CUA}$ and a C-terminally hexahistidine tagged sfGFP gene with an amber codon at position 150). Cells were recovered in 1 ml of S.O.B media (supplemented with 0.2% glucose) for 1 h at 37° C., before incubation (16 h, 37° C., 230r.p.m) in 100 ml of LB containing ampicillin (100 μg/mL) and tetracycline (25 μg/mL). 20 ml of this overnight culture was used to inoculate 1 L of LB supplemented with ampicillin (50 μg/mL) and tetracycline (12 μg/mL) and incubated at 37° C. At OD$_{600}$=0.4 to 0.5, a solution of 1 in H$_2$O was added to a final concentration of 2 mM. After 30min, protein expression was induced by the addition of arabinose to a final concentration of 0.2 %. After 3 h of induction, cells were harvested by centrifugation and and frozen at −80° C. until required. Cells were thawed on ice and suspended in 30 ml of lysis buffer (10mM Tris-HCl, 20 mM imidazole, 200 mM NaCl, pH 8, 1 mM phenylmethanesulfonylfluoride, 1 mg/mL lysozyme, 100 μg/mL DNaseA, Roche protease inhibitor). Proteins were extracted by sonication at 4° C. The extract was clarified by centrifugation (20 min, 21.000 g, 4° C.), 600 μL of Ni$^{2+}$—NTA beads (Qiagen) were added to the extract and the mixture was incubated with agitation for 1 h at 4° C. Beads were collected by centrifugation (10 min, 1000 g). The beads were three times resuspended in 30 mL wash buffer (20 mM Tris-HCl, 30 mM imidazole, 300 mM NaCl, pH 8) and spun down at 1000 g. Subsequently, the beads were resuspended in 10 mL of wash buffer and transferred to a column. The protein was eluted with 3 ml of wash buffer supplemented with 200 mM imidazole and further purified by size-exclusion chromatography employing a HiLoad 16/60 Superdex 75 Prep Grade column (GE Life Sciences) at a flow rate of 1 mL/min (buffer: 20 mM Tris-HCl, 100 mM NaCl, 2 mM EDTA, pH 7.4). Fractions containing the protein were pooled and concentrated with an Amicon Ultra-15 3 kDa MWCO centrifugal filter device (Millipore). Purified proteins were analyzed by 4-12% SDS-PAGE and their mass confirmed by mass spectrometry (sec Supplementary Information). SfGFP with incorporated 2 and 3, sfGFP-2, sfGFP-3 were prepared in the same way, expect that cells were transformed with pBKTCORS (which encodes MbTCORS) and and psfGFP150TAGPylT-His$_6$ (which encodes MbRNA$_{CUA}$ and a C-terminally hexahistidine tagged sfGFP gene with an amber codon at position 150). SfGFP with incorporated 4 and 5, sfGFP-4, sfGFP-5 were prepared in the same way, expect that cells were transformed with pBKPylRS (which encodes MbPylRS) and and psfGFP150TAGPylT-His$_6$ (which encodes MbtRNA$_{CUA}$ and a C-terminally hexahistidine tagged sfGFP gene with an amber codon at position 150). Yields of purified proteins were up to 6-12 mg/L.

Protein Mass Spectrometry

Using an Agilent 1200 LC-MS system, ESI-MS was carried out with a 6130 Quadrupole spectrometer. The solvent system consisted of 0.2% formic acid in H$_2$O as buffer A, and 0.2% formic acid in acetonitrile (MeCN) as buffer B. LC-ESI-MS on proteins was carried out using a Phenomenex Jupiter C4 column (150×2 mm, 5 μm) and samples were analyzed in the positive mode, following protein UV absorbance at 214 and 280 nm. Total protein masses were calculated by deconvolution within the MS Chemstation software (Agilent Technologies).

Additionally, protein total mass was determined on an LCT time-of-flight mass spectrometer with electrospray ionization (ESI, Micromass). Proteins were rebuffered in 20 mM of ammonium bicarbonate and mixed 1:1 acetonitrile, containing 1% formic acid. Alternatively samples were prepared with a C4 Ziptip (Millipore) and infused directly in 50% aqueous acetonitrile containing 1% formic acid. Samples were injected at 10 μL min$^{-1}$ and calibration was performed in positive ion mode using horse heart myoglobin. 30 scans were averaged and molecular masses obtained by maximum entropy deconvolution with MassLynx version 4.1 (Micromass). Theoretical masses of wild-type proteins were calculated using Protparam (http://us.expasy.org/tools/protparam.html), and theoretical masses for unnatural amino acid containing proteins were adjusted manually.

Protein Labelling via Tetrazine-BCN or Tetrazine-TCO Cycloaddition

In vitro Labelling of Purified Proteins with Different Tetrazines

To 40 μL of purified recombinant protein (~10 μM in 20 mM Tris-HCl, 100 mM NaCl, 2 mM EDTA, pH 7.4) 4 μL of a 1 mM solution of tetrazine compounds 6, 7, 8, or 9 in MeOH were added (~10 or 20 equivalents). After 30 minutes of incubation at room temperature, the solutions were analyzed by LC-ESI-MS. (FIG. 20)

In vitro Labelling of Purified Proteins with Tetrazines and Tetrazine-Dye Conjugates:

Purified recombinant sfGFP with site-specifically incorporated 1 or 2, sfGFP-1 or sfGFP-2 (~10 μM in 20 mM Tris-HCl, 100 mM NaCl, 2 mM EDTA, pH 7.4), was incubated with 10 equivalents of the tetrazine-dye conjugates 11, 12, 13, 14, 15 or 16, respectively (2 mM in DMSO). The solution was incubated at room temperature and aliquots were taken after 30 min to 3 hours and analyzed by SDS PAGE and—after desalting with a C4-ZIPTIP—by ESI-MS. The SDS PAGE gels were either stained with coomassie or scanned with a Typhoon imager to visualize in-gel fluorescence (FIG. 4 and FIG. 19).

In vitro Labelling of Purified Proteins with Tetrazines-Dye Conjugates as a Function of Time:

2 nmol of purified sfGFP-1, sfGFP-2 or sfGFP-4 (10 μM in 20 mM Tris-HCl, 100 mM NaCl, 2 mM EDTA, pH 7.4) were incubated with 20 nmol of tetrazine-dye conjugate 11 (10 μl of a 2 mM solution in DMSO). At different time points (0, 30 s, 1 min, 2 min, 5min, 10 min, 30 min, 1 h, 2 h, 3 h) 8 μL aliquots were taken from the solution and quenched with a 700-fold excess of BCN or TCO and plunged into liquid nitrogen. Samples were mixed with NuPAGE LDS sample buffer supplemented with 5% β-mercaptoethanol, heated for 10 min to 90° C. and analyzed by 4-12% SDS page. The amounts of labelled proteins were quantified by scanning the fluorescent bands with a Typhoon Trio phosphoimager (GE Life Sciences). Bands were quantified with the ImageQuant™ TL software (GE Life Sciences) using rubber band background subtraction. In gel fluorescence shows that labelling is complete within 1 h for sfGFP-4 using 10 equivalents tetrazine-fluorophore 11 (FIG. 4*e*), whereas the labelling of sfGFP-1 and sfGFP-2 was complete within the few seconds it took to measure the first time point.

Labelling of the Whole *E. Coli* Proteome with Tetrazine-Dye Conjugates:

*E. coli* DH10B cells containing either psfGFP150TAGPylT-His$_6$ and pBKBCNRS or psfGFP150TAGPylT-His$_6$ and pBKPylRS were inoculated into LB containing ampicillin (for pBKBCNRS, 100 μg/mL) or kanamycin (for pBKPylRS 50 μg/mL) and tetracycline (25 μg/mL). The cells were incubated with shaking overnight at 37° C., 250 rpm. 2 mL of overnight culture was used to inoculate into 100 mL of LB supplemented with ampicillin (50 μg/mL) and tetracycline (12 μg/mL) or kanamycin (25 μg/mL) and tetracycline (12 μg/mL) and incubated at 37° C. At OD$_{600}$ 0.5, 3 ml culture aliquots were removed and supplemented with different concentrations (1 mM, 2 mM and 5 mM) of 1 and 1 mM of 5. After 30 min of incubation with shaking at 37° C., protein expression was induced by the addition of 30 μL, of 20% arabinose. After 3.5 h of expression, cells were collected by centrifugation (16000 g, 5 min) of 1 mL of cell suspension. The cells were resuspended in PBS buffer, spun down again and the supernatant was discarded. This process was repeated twice more. Finally, the washed cell pellet was suspended in 100 μl, PBS and incubated with 3 μl, of tetrazine-dye conjugate 11 (2 mM in DMSO) at rt for 30 minutes. After adding a 200-fold excess of BCN in order to quench non-reacted tetrazine-dye, the cells were resuspended in 100 μL of NuPAGE LDS sample buffer supplemented with 5% β-mercaptoethanol, heated at 90° C. for 10 min and centrifuged at 16000 g for 10 min. The crude cell lysate was analyzed by 4-12% SDS-PAGE to assess protein levels. Gels were either Coomassie stained or scanned with a Typhoon imager to make fluorescent bands visible (FIG. 20 and 21). Western blots were performed with antibodies against the hexahistidine tag (Cell Signaling Technology, His tag 27E8 mouse mAb #2366).

Stopped-Flow Determination of Kinetic Rate Constants for Small Molecule Cycloadditions Rate constants k for different tetrazines were measured under pseudo first order conditions with a 10- to 100-fold excess of BCN or TCO in methanol/water mixtures by following the exponential decay in UV absorbance of the tetrazine at 320, 300 or 280 nm over time with a stopped-flow device (Applied Photophysics, FIG. 13 and 14 and Supplementary Table 1). Stock solutions were prepared for each tetrazine (0.1 mM in 9/1 water/methanol) and for BCN and TCO (1 to 10 mM in methanol). Both tetrazine and BCN and TCO solutions were thermostalted in the syringes of the stopped flow device before measuring. Mixing equal volumes of the prepared stock solutions via the stopped-flow apparatus resulted in a final concentration of 0.05 mM tetrazine and of 0.5 to 5 mM BCN or TCO, corresponding to 10 to 100 equivalents of BCN or TCO. Spectra were recorded using the following instrumental parameters: wavelength, 320 nm for 6 and 7; 300 nm for 8, 280 nm for 9; 500 to 5000 datapoints per second). All measurements were conducted at 25° C. Data were fit to a single-exponential equation for BCN-tetrazine reactions and to a sum of two single exponential equations for TCO-tetrazine reactions. Each measurement was carried out three to five times and the mean of the observed rates k' (the first exponential equation in case of the TCO-tetrazine reaction) was plotted against the concentration of BCN or TCO to obtain the rate constant k from the slope of the plot. For all four tetrazines complete measurement sets were done in duplicate and the mean of values is reported in Supplementary Table 1. All data processing was performed using Kaleidagraph software (Synergy Software, Reading, UK).

Cloning for Mammalian Cell Applications

The plasmids pMmPylS-mCherry-TAG-EGFP-HA[1,2] and pMmPylRS-EGFR-(128TAG) -GFP-HA[2] were both digested with the enzymes AflII and EcoRV (NEB) to remove the wild-type MmPylRS. A synthetic gene of the mutant synthetase MbBCNRS and MbTCORS was made by GeneArt with the same flanking sites. The synthetic MbBCNRS and MbTCORS were also digested with AflII and EcoRV and cloned in place ofthe wild -type synthetase (MmPylS). Using a rapid ligation kit (Roche) vectors pMbBCNRS -mCherry-TAG-EGFP-HA, pbBCNRS-EGFR (128TAG)-GFP-HA and pMbTCORS -EGFR(128TAG)-GFP-HA were created. The pCMV-cJun-TAG-mCherry-MbBCNRS plasmid was created from a pCMV-cJun-TAG-mCherry-MmPylRS plasmid (created by Fiona Townsley) by exchanging MmPylRS for MbBCNRS. This was carried out as for the pMbBCNRS-mCherry-TAG-EGFP-HA plasmid.

Incorporation of amino acid 1, 2 and 3 in HEK293 cells

HEK293 cells were plated on poly-lysine coated μ-dishes (Ibidi). After growing to near confluence in 10% fetal bovine serum (FBS) Dulbecco's modified eagle medium (DMEM) cells were transfected with 2 μg ofpMbBCNRS-EGFR (128TAG)-GFP-HA and 2 μg of p4CMVE-U6-PylT (which contains four copies of the wild-type pyrrolysyl tRNA)[1,2] using lipofectamin 2000 (Life Technologies). After transfection cells were left to grow overnight in 10% FBS DMEM at 37° C. and 5% $CO_2$. For a western blot, cells were plated on 24 well plates and grown to near confluence. Cells were transfected using lipofectamine 2000 with the pMbBCNRS-mCherry-TAG-EGFP-HA or pMmPylRS-mCherry-TAG-EGFP-HA or pTCORS-mCherry-TAG-EGFP-HA construct and the p4CMVE-U6-PylT plasmid. After 16 hours growth with or without 0.5 mM 1, 1 mM 2 or 1 mM 5 cells were lysed on ice using RIPA buffer (Sigma). The lysates were spun down and the supernatant was added to 4× LDS sample buffer (Life technologies). The samples were run out by SDS-PAGE, transferred to a nitrocellulose membrane and blotted using primary rat anti-HA (Roche) and mouse anti-FLAG (Ab frontier), secondary antibodies were anti-rat (Santa Cruz Biotech) and anti-mouse (Cell Signaling) respectively.

Labelling of Mammalian Cell Surface Protein

Cells were plated onto a poly-lysine coated μ-dish and after growing to near confluence were transfected with 2 μg each of pMbBCNRS-EGFR(128TAG)-GFP-HA or pMbTCORS-EGFR(128TAG)-GFP-HA and p4CMVE-U6-PylT. After 8-16 hours growth at 37° C. and at 5% $CO_2$ in DMEM with 0.1% FBS in the presence of 0.5 mM 1 (0.5% DMSO), 1 mM 2 or 1 mM 3 cells were washed in DMEM with 0.1% FBS and then incubated in DMEM with 0.1% FBS overnight. The following day cells were washed once more before 400 nM terazine-dye conjuagate 11 was added for 2-60 minutes. The media was exchanged twice and cells were then imaged. Imaging was carried out on a Zeiss 780 laser scanning microscope with a Plan apochromat 63X oil immersion objective, scan zoom: 1× or 2×; scan resolution: 512×512; scan speed: 9; averaging: 16×. EGFP was excited at 488 nm and imaged at 493 to 554 nm; TAMRA was excited and detected at 561 nm and 566-685 nm respectively.

Controls were performed similarly but transfected with pMmPylRS-EGFR(128TAG)-GFP-HA instead ofPMbBCNRS-EGFR(128TAG)-GFP-HA. Cells were grown overnight in the presence of 1 mM 5 and in the absence or presence of 0.5% DMSO (as would be the case for amino acid 1).

Labeling of Mammalian Nuclear Protein

Cells were plated onto a poly-lysine coated p-dish and after growing to near confluence were transfected with 2 μg each of pCMV-cJun-TAG-mCherry and p4CMVE-U6-PylT. After approximately 16 hrs growth at 37° C. and at 5% $CO_2$ in DMEM with 0.1% FBS in the presence of 0.5 mM 1 (0.5% DMSO) cells were washed in DMEM 0.1% FBS and then incubated in DMEM 0.1% FBS overnight. The following day cells were washed repeatedly, using two media exchanges followed by 30 minutes incubation over 2 hours. 200 nM tetrazine-dye conjugate 11 was added for 15 minutes, the cells were then repeatedly washed again for 90 mins. Imaging was carried out as for the cell surface labeling Chemical Syntheses General Methods NMR spectra were recorded on a Bruker Ultrashield™ 400 Plus spectrometer ($^1$H: 400 MHz, $^{13}$C: 101 MHz, $^{31}$P: 162 MHz). Chemical shifts (δ) are reported in ppm and are referenced to the residual non-deuterated solvent peak: $CDCl_3$ (7.26 ppm), $d_6$-DMSO (2.50 ppm) for $^1$H-NMR spectra, $CDCl_3$ (77.0 ppm), $d_6$-DMSO (39.5 ppm) for $^{13}$C-NMR spectra. $^{13}$C- and $^{31}$P-NMR resonances are proton decoupled. Coupling constants (J) are measured to the nearest 0.1 Hz and are presented as observed. Splitting patterns are designated as follows: s, singlet; d, doublet; t, triplet; q, quartet; quin, quintet; sext, sextet; m, multiplet. Analytical thin-layer chromatography (TLC) was carried out on silica 60F-254 plates. The spots were visualized by UV light (254 nm) and/or by potassium permanganate staining. Flash column chromatography was carried out on silica gel 60 (230-400 mesh or 70-230 mesh). ESI-MS was carried out using an Agilent 1200 LC-MS system with a 6130 Quadrupole spectrometer. The solvent system consisted of 0.2% formic acid in $H_2O$ as buffer A, and 0.2% formic acid in acetonitrile (MeCN) as buffer B. Small molecule LC-MS was carried out using a Phenomencx Jupiter C18 column (150×2 mm, 5 μm). Variable wavelengths were used and MS acquisitions were carried out in positive and negative ion modes. Preparative HPLC purification was carried out using a Varian PrepStar/ProStar HPLC system, with automated fraction collection from a Phenomenex C18 column (250× 30 mm, 5 μm). Compounds were identified by UV absorbance at 191 nm. All solvents and chemical reagents were purchased from commercial suppliers and used without further purification. Bicyclo[6.1.0]non-4-yn-9-ylmethanol (BCN, exo/endo mixture ~4/1) was purchased from Syn-Affix, Netherlands. Non-aqueous reactions were carried out in oven-dried glassware under an inert atmosphere of argon unless stated otherwise. All water used experimentally was distilled. Brine refers to a saturated solution of sodium chloride in water.

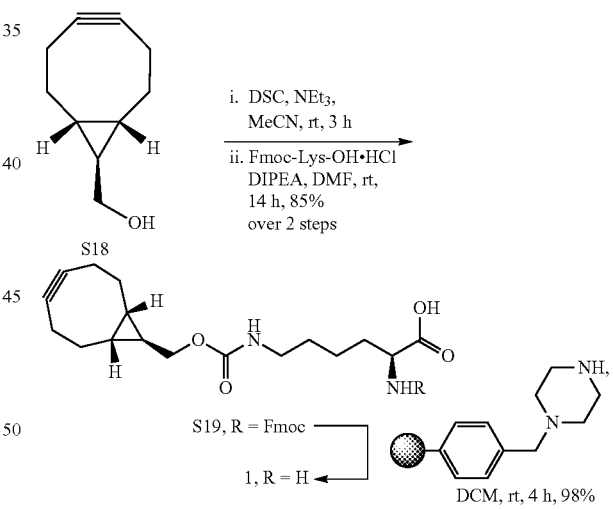

exo-Bicyclo[6.1.0]non-4-yn-9-ylmethanol (exo-BCN, S18) was synthesised according to a literature procedure.[3]

N,N'-disuccinimidyl carbonate (1.38 g, 5.37 mmol) was added to a stirring solution of exo-BCN-OH S18 (538 mg, 3.58 mmol) and triethylamine (2.0 mL, 14.3 mmol) in MeCN (10 mL) at 0° C. The solution was warmed to room temperature and stirred for 3 h and concentrated under reduced pressure. The crude oil was purified through a short pad of silica gel chromatography (eluting with 60% EtOAc in hexane) to yield the exo-BCN -succinimidyl carbonate, which was used without further purification. exo-BCN-OSu (1.25 g, 4.29 mmol) in DMF (4 mL) was added via cannula to a stirring solution of Fmoc -Lys-OH.HCl (2.61 g, 6.45 mmol) and DIPEA (1.49 mL, 8.58 mmol) in DMF (10 mL). The solution was stirred at room temperature for 14 h, diluted with Et$_2$O (100 mL) and washed with H$_2$O (3×100 mL). The organic phase was dried over sodium sulfate, filtered and concentrated under reduced pressure. The crude oil was purified by silica gel chromatography (0-5% MeOH in DCM (0.1% AcOH)) to yield exo-Fmoc-BCNK-OH S19 as a white solid (1.65 g, 85% over 2 steps). $\delta_H$ (400 MHz, d$_6$-DMSO) 12.67-12.31 (1H, br s), 7.90 (2H, d, J 7.5), 7.73 (2H, d, J 7.4), 7.63 (1H, d, J 7.8), 7.42 (2H, t, J 7.4), 7.34 (2H, t, J 7.4), 7.10 (1H, t, J 5.7), 4.31-4.19 (3H, m), 3.95-3.87 (1H, m), 3.84 (1H, d, J 6.4), 3.45-3.25 (br s, 1H), 3.01-2.91 (2H, m), 2.52-2.50 (1H, m), 2.33-2.15 (4H, m), 2.11-2.02 (2H, m), 1.75-1.54 (2H, m), 1.46-1.23 (6H, m), 0.70-0.58 (2H, m); $\delta_C$ (101 MHz, d$_6$-DMSO) 174.4, 156.9, 156.6, 144.30, 144.27, 141.2, 128.1, 127.5, 125.7, 120.6, 99.4, 68.1, 66.1, 54.3, 47.1, 33.3, 30.9, 29.5, 23.9, 23.4, 22.7, 21.3; LRMS (ESI$^+$): m/z 543 (100% [M−H]$^−$).

Polymer-bound piperazine (1.28 g, 1.28 mmol, 200-400 mesh, extent of labeling: 1.0-2.0 mmol/g loading, 2% crosslinked with divinylbenzene) was added to a stirring solution of exo-Fmoc-BCNK-OH S19 (174 mg, 0.32 mmol) in DCM (10 mL). The resulting mixture was stirred for 4 h at room temperature, filtered and the reagent washed with CHCl$_3$/MeOH (3:1, 3×50 mL). The filtrate was evaporated under reduced pressure, dissolved in H$_2$O (100 mL) and washed with EtOAc (3×100 mL). The aqueous phase was evaporated under reduced pressure and freeze-dried to yield exo-H-BCNK-OH 1 as a white solid (101 mg, 98%). For all subsequent labeling experiments using mammalian cells exo-H-BCNK-OH 1 was further purified by reverse-phase HPLC (0:1 H$_2$O:MeCN to 9:1 H$_2$O:MeCN gradient). $\delta_H$ (400 MHz, d$_6$-DMSO/D$_2$O (1:1)) 4.14-3.76 (m, 3H), 3.56-3.29 (m, 2H), 3.18-2.81 (m, 3H), 2.31-1.98 (m, 5H), 1.71-1.52 (m, 4H), 1.51-1.29 (m, 4H), 1.29-1.08 (m, 3H), 0.95-0.66 (m, 2H); $\delta_C$ (101 MHz, d$_6$-DMSO/D$_2$O (1:1)) 169.4, 165.9, 101.3, 76.0, 55.8, 31.8, 30.1, 29.9, 25.2, 23.2, 22.1, 21.0, 18.7; LRMS (ESI$^+$): m/z 323 (100% [M+H]$^+$). endo-Bicyclo[6.1.0]non-4-yn-9-ylmethanol (endo -BCN) was synthesised according to a literature procedure[3] and elaborated to the corresponding amino acid in an analogous fashion to 1.

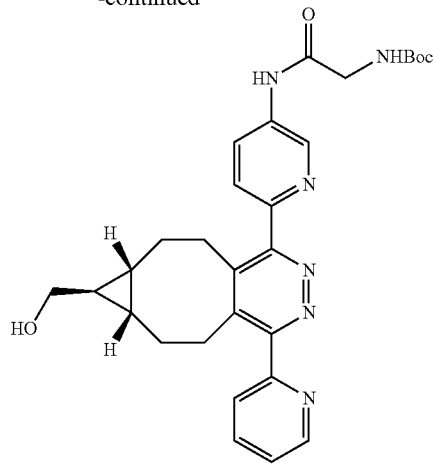

S20

A glass vial (Biotage® Ltd.) equipped with a magnetic stirring bar was charged with compound 6 (39.2 mg, 0.096 mmol) and was sealed with an air-tight aluminium/rubber septum. The contents in the vial were dried in vacuo and purged with argon gas (×3). MeOH (1 ml) was added to the vial, followed by addition of a solution of exo -Bicyclo [6.1.0]non-4-yn-9-ylmethanol (exo-BCN, S18) (20.2 mg in 1 ml of MeOH, 0.1344 mmol). The mixture was stirred at room temperature. Within 2 min, the reaction mixture decolorised and the contents were left stirring for additional 1 min. The mixture was then evaporated under reduced pressure and purified by silica gel chromatography (5% MeOH in DCM) to afford pyridazine S20 as a faint yellow semi-solid (49 mg, 96%). $\delta_H$ (400 MHz, CDCl$_3$) 9.16 (1H, br s), 8.77-8.71 (1H, m), 8.67 (1H, app. d, J 2.1), 8.01 (1H, br s), 7.97 (1H, d, J 7.8), 7.89 (1H, ddd, J 7.8, 7.6, 1.7), 7.75 (1H, app. d, J 8.4), 7.40 (1H, ddd, J 7.4, 4.9, 1.1), 5.93 (1H, br s), 4.02 (2H, d, J 5.0), 3.49-3.31 (2H, m), 3.12-2.88 (4H, m), 2.68-2.49 (2H, m), 1.88-1.60 (1H, br s), 1.60-1.50 (1H, m), 1.48 (9H, s), 0.92-0.72 (4H, m); $\delta_C$ (101 MHz, CDCl$_3$) 169.0, 159.2, 159.0, 156.9, 156.8, 155.7, 152.1, 148.9, 143.0, 140.9, 137.0, 134.4, 128.0, 125.1, 124.9, 123.5, 80.7, 66.4, 45.7, 30.7, 29.9, 29.6, 29.5, 28.5 (3×CH$_3$ ($^t$Bu)), 28.0, 27.8, 21.7; LRMS (ESI$^+$): m/z 531 (100% [M+H]$^+$).

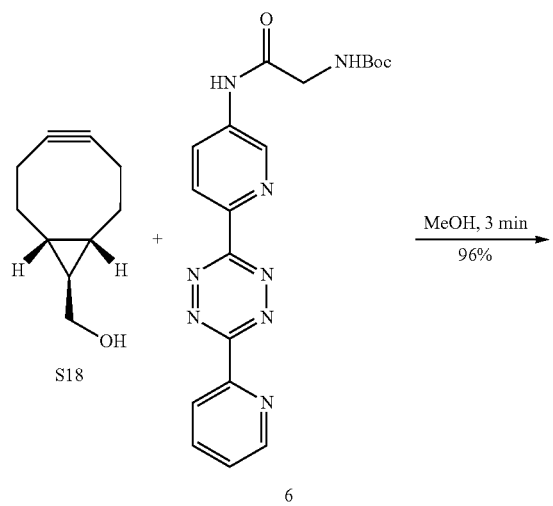

6

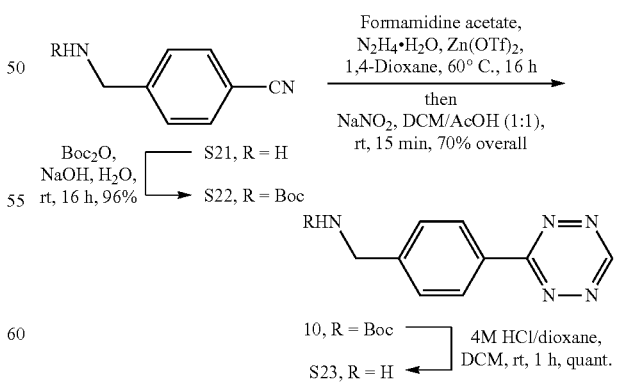

Commercially available 4-(Aminomethyl)benzonitrile hydrochloride S21 (2.11 g, 12.50 mmol) in H$_2$O (10 mL) was added to a stirring solution of NaOH (1.50 g, 37.50 mmol) and di-tert-butyl dicarbonate (3.00 g, 13.75 mmol) in H₂O (10 mL) at room temperature. The mixture was stirred for 16 h, after which time a white precipitate had formed. The mixture was filtered, washed with H₂O (50 mL), and the resulting solid dried under vacuum to yield tert-butylcarbamate S22 as a white solid (2.78 g, 96%). $\delta_H$ (400 MHz, CDCl₃) 7.62 (2H, d, J 8.2), 7.39 (2H, d, J 8.2), 5.00 (1H, br s), 4.37 (2H, d, J 5.8), 1.46 (9H, s); $\delta_C$ (101 MHz, CDCl₃) 155.9, 144.7, 132.4, 127.8, 118.9, 111.1, 80.1, 44.2, 28.4; LRMS (ESI⁺): m/z 233 (100% [M+H]⁺).

Tetrazine 10 was synthesised by modification of a literature procedure.[4] Hydrazine monohydrate (1.024 mL, 21.10 mmol) was added to a stirring suspension of tert-butylcarbamate S22 (98 mg, 0.44 mmol), formamidine acetate (439 mg, 4.22 mmol), and Zn(OTf)₂ (77 mg, 0.22 mmol) in 1,4-dioxane (0.5 mL) at room temperature. The reaction was heated to 60° C. and stirred for 16 h. The reaction was cooled to room temperature and diluted with EtOAc (10 mL). The reaction was washed with 1M HCl (10 mL) and the aqueous phase extracted with EtOAc (2×5 mL). The organic phase was dried over sodium sulfate, filtered and evaporated under reduced pressure. The resulting crude residue was dissolved in a mixture of DCM and acetic acid (1:1, 5 mL), and NaNO₂ (584 mg, 8.44 mmol) was added slowly over a period of 15 minutes, during which time the reaction turned bright red. The nitrous fumes were chased with an active air purge and the reaction then diluted with DCM (25 mL). The reaction mixture was washed with sodium bicarbonate (sat., aq., 25 mL) and the aqueous phase extracted with DCM (2×10 mL). The organic phase was dried over sodium sulfate, filtered and evaporated under reduced pressure. The resulting residue was purified by silica gel chromatography (20% EtOAc in hexane) to yield tetrazine 10 as a pink solid (85 mg, 70%). $\delta_H$ (400 MHz, CDCl₃) 10.21 (1H, s), 8.60 (2H, d, J 8.2), 7.53 (2H, d, J 8.2), 4.97 (1H, br s), 4.45 (2H, d, J 6.0), 1.49 (9H, s); $\delta_C$ (101 MHz, CDCl₃) 149.4, 142.6, 141.1, 120.8, 119.2, 118.8, 51.8, 39.0; LRMS (ESI⁺): m/z 188 (100% [M+H]⁺).

4M HCl in dioxane (2 mL, 8.0 mmol) was added to a stirring solution of tetrazine 10 (75 mg, 0.26 mmol) in DCM (4 mL). After 1 h the reaction was complete and the solvent was removed under reduced pressure to yield primary amine hydrochloride S23 as a pink solid (61 mg, 100%). $\delta_H$ (400 MHz, d₆-DMSO) 10.64 (1H, s), 8.54 (2H, d, J 8.4), 7.79 (2H, d, J 8.4), 4.18 (2H, d, J 5.5); $\delta_C$ (101 MHz, d₆-DMSO) 165.2, 158.2, 138.9, 131.9, 129.8, 127.9, 41.8; LRMS (ESI⁺): m/z 188 (100% [M+H]⁺).

E-5-hydroxycyclooctene and E-exo-Bicyclo[6.1.0]non-4-ene-9-ylmethanol were either made by previously described photochemical procedures[5,6], or by the non-photochemical protocols described below.

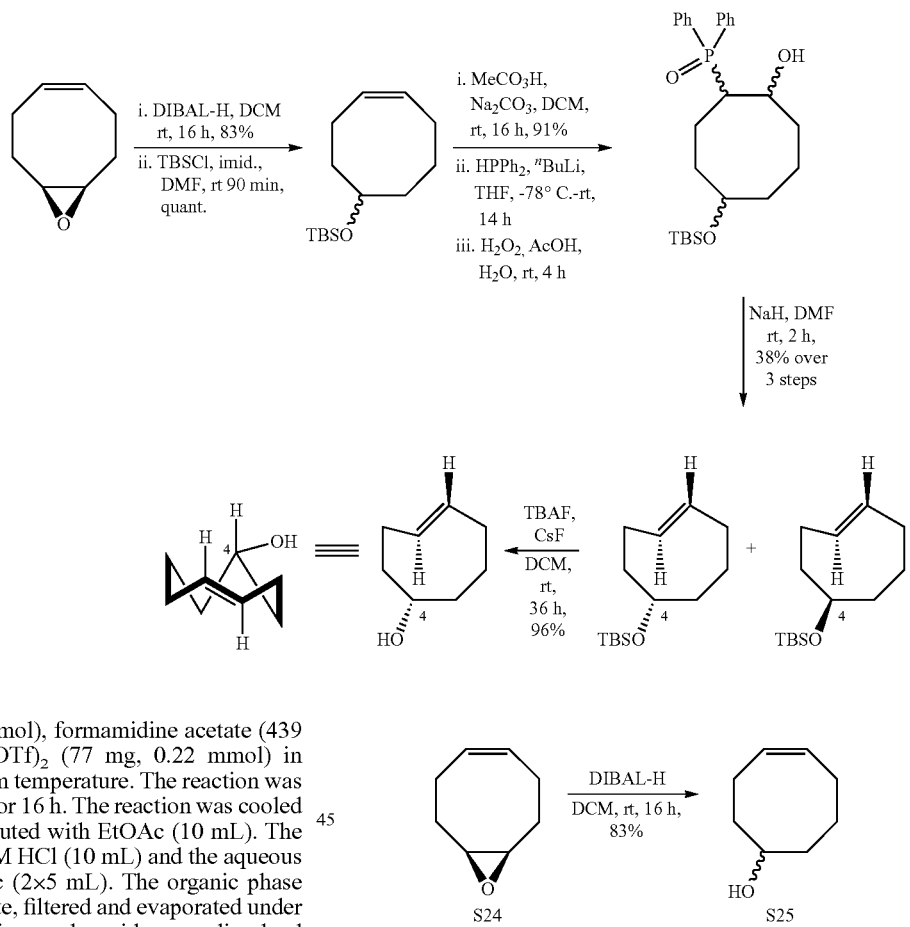

Diisobutylaluminium hydride (1.0 M solution in cyclohexane, 89 mL, 89 mmol) was added drop-wise to a stirring solution of commercially available 9-oxabicyclo[6.1.0]non-4-ene S24 (10 g, 80.53 mmol) in DCM (300 mL) at 0° C. The solution was stirred at 0° C. for 30 min, warmed to room temperature and stirred for 16 h. After this time, the reaction was cooled to 0° C. and propan-2-ol (50 mL) was added slowly followed by HCl (1M, aq., 100 mL). The aqueous phase was extracted with DCM (3×200 mL). The combined organics were washed with brine, dried over sodium sulfate, filtered and concentrated under reduced pressure. The crude material was purified by silica gel chromatography (10-20% EtOAc in hexanes) to yield cyclooctene-4-ol S25 as a colorless oil (8.42 g, 83%). Spectral data was in accordance with the literature.[7]

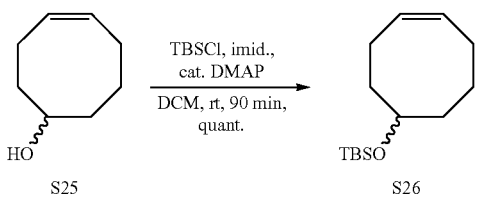 [SMILES: OC1CC/C=C\CCC1 ; CC(C)(C)[Si](C)(C)OC1CC/C=C\CCC1 ; "S25" ; "S26"]

tert-Butyl(chloro)dimethylsilane (13.3 g, 88.0 mmol) was added to a stirring solution of cyclooctene-4-ol S25 (5.6 g, 44.0 mmol), imidazole (7.5 g, 0.11 mol) and DMAP (1 crystal) in DCM (30 mL) at 0° C. The solution was warmed to room temperature and stirred for 90 min, during which time a white precipitate formed. The reaction was cooled to 0° C., diluted with DCM (100 mL) and sodium bicarbonate (sat., aq., 100 mL) was added. The phases were separated and the aqueous phase was extracted with DCM (3×100 mL). The combined organics were washed with brine (200 mL), dried over sodium sulfate, filtered and concentrated under reduced pressure. The crude material was purified by silica gel chromatography (10-20% DCM in hexane) to yield silyl ether S26 as colorless oil (10.55 g, quant.). $\delta_H$ (400 MHz, CDCl$_3$) 5.71-5.63 (1H, m), 5.60-5.52 (1H, m), 3.80 (1H, app td, J 8.6,4.2), 2.34 (1H, dtd, J 13.8, 8.2,3.8), 2.25-2.15 (1H, m), 2.13-2.05 (1H, m), 2.02-1.93 (1H, m), 1.87-1.52 (5H, m), 1.47-1.35 (1H, m), 0.88 (9H, s), 0.04 (3H, s), 0.03 (3H, s); $\delta_C$ (101 MHz, CDCl$_3$) 130.4, 129.4, 73.1, 38.0, 36.5, 26.1, 25.8, 25.1, 22.7, 18.4, −3.4; LRMS (ESI$^+$): m/z 241 (11% [M+H]$^+$).

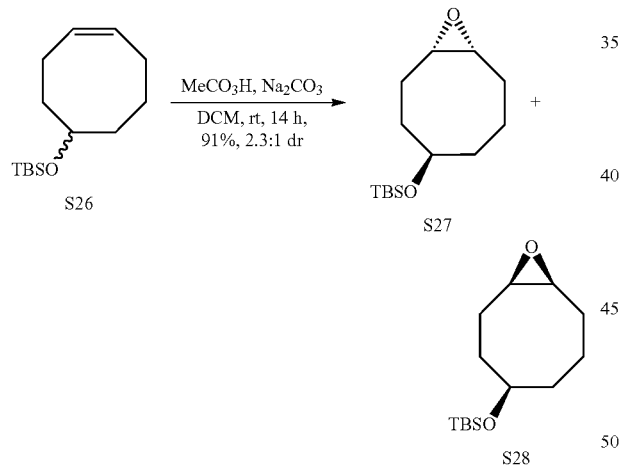

Peracetic acid (39% in acetic acid, 10.3 ml, 52.7 mmol) was added drop-wise to a stirred solution of silyl ether S26 (10.6 g, 43.9 mmol) and sodium carbonate (7.0 g, 65.8 mmol) in DCM (80 mL) at 0° C. The mixture was warmed to room temperature and stirred for 14 h. The reaction was cooled to 0° C., diluted with DCM (50 mL) and sodium thiosulfate (sat., aq., 100 mL) was added. The mixture was stirred at room temperature for 10 min and then basified to pH 12 with NaOH (2M, aq.). The phases were separated and the organic phase washed with H$_2$O (100 mL), brine (100 mL), dried over sodium sulfate, filtered and concentrated under reduced pressure. The crude material was purified by silica gel chromatography (80%-90% DCM in hexane) to yield epoxides S27/S28, as an inseparable mixture of diastereomers (2.3:1 by $^1$H-NMR) and as a colorless oil (10.2 g, 91%). Major diastereomer. $\delta_H$ (400 MHz, CDCl$_3$) 3.90 (1H, app sext, J 4.2), 2.90 (2H, ddd, J 16.7, 8.3, 4.4), 2.21-2.09 (1H, m), 1.85-1.60(6H, m), 1.50-1.38 (2H, m), 1.34-1.23 (1H, m), 0.88 (9H, s), 0.04 (3H, s), 0.03 (3H, s); $\delta_C$ (101 MHz, CDCl$_3$) 171.9, 55.5, 55.4, 36.3, 34.3, 27.7, 26.0, 25.8, 22.6, 18.3, −3.4; LRMS (ESI$^+$): m/z 257 (8% [M+H]$^+$).

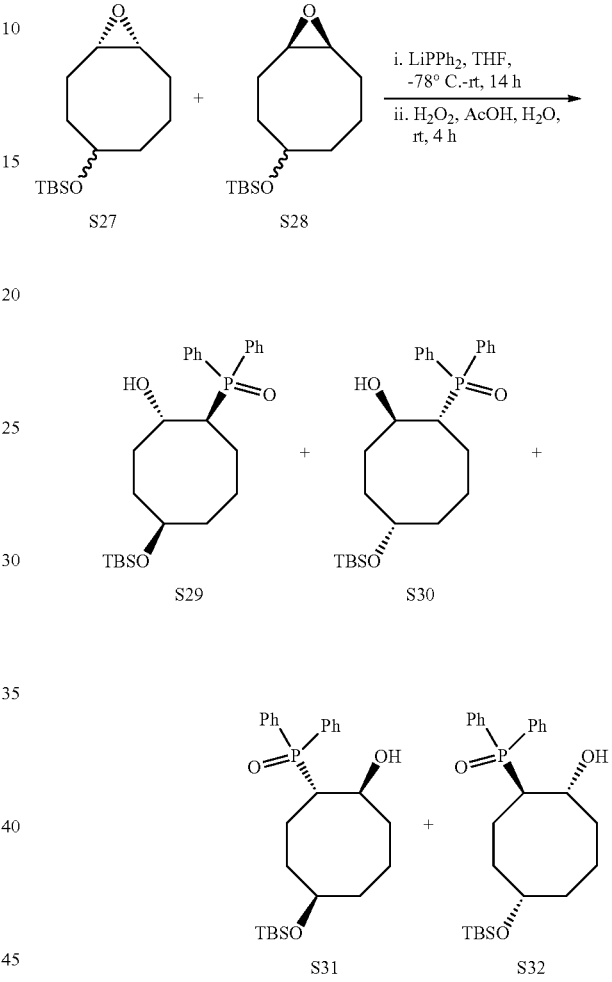

n-Butyllithium (2.5 M in hexanes, 14.8 mL, 37.0 mmol) was added drop-wise over 15 min to a stirring solution of epoxides S27/S28 (7.9 g, 30.8 mmol) and diphenylphosphine (6.43 mL, 37.0 mmol) in THF (80 mL) at −78° C. The resulting mixture was stirred at −78° C. for 1 h, warmed to room temperature and stirred for 14 h. The reaction mixture was diluted with THF (80 mL) and cooled to 0° C. Acetic acid (5.54 mL, 92.4 mmol) was added followed by hydrogen peroxide (30% solution in H$_2$O, 7.68 mL, 67.7 mmol). The reaction mixture was warmed to room temperature and stirred for 4 h. Sodium thiosulfate (sat., aq., 100 mL) was added and the mixture stirred for 10 min. The aqueous phase was extracted with EtOAc (3×200 mL). The combined organics were washed with brine (3 ×200 mL), dried over sodium sulfate, filtered and concentrated under reduced pressure to yield phosphine oxides S29/S30/S31/S32 as a mixture of four diastereomers, which were used without further purification. $\delta_P$ (162 MHz, CDCl$_3$) 45.2, 44.8, 44.4, 43.8; LRMS (ESI$^+$): m/z 459 (100% [M+H]$^+$).

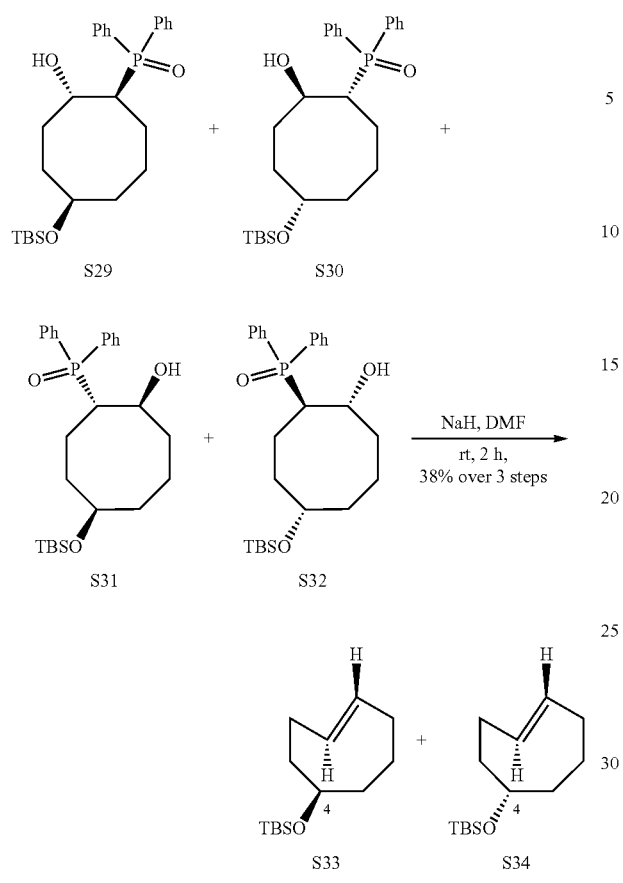

Sodium hydride (60% dispersion in mineral oil, 2.46 g, 61.5 mmol) was added to a stirring solution of crude hydroxyl phosphine oxides S29/S30/S31/S32 in DMF (100 mL) at 0° C. The resulting mixture was warmed to room temperature, wrapped in tin foil and stirred for 2 h. The reaction was cooled to 0° C., diluted with Et$_2$O (200 mL) and H$_2$O (200 mL) was added. The phases were separated and the combined organics washed with brine (2 ×200 mL), dried over sodium sulfate, filtered and concentrated under reduced pressure. The crude mixture was purified by silica gel chromatography (1-15% DCM in hexane) to yield trans-cyclooctenes S33/S34 as a separable mixture of diastereomers, with exclusive E-selectivity, and as colorless oils (2.78 g, 1.2:1 dr, 38% over 3 steps). S33: $\delta_H$ (400 MHz, CDCl$_3$) 5.64 (1H, ddd, J 16.0, 10.8, 3.6), 5.45 (1H, ddd, J 15.9, 11.1, 3.2), 4.01 (1H, app dd, J 10.2, 5.4), 2.41 (1H, qd, J 11.5, 4.4), 2.26-2.19 (1H, m), 2.09-1.94 (3H, m), 1.92-1.73 (2H, m), 1.71-1.63 (1H, m), 1.54 (1H, tdd, J 14.0, 4.7, 1.1), 1.30-1.08 (1H, m), 0.94 (9H, s), 0.03 (3H, s), 0.01 (3H, s); $\delta_C$ (101 MHz, CDCl$_3$) 135.9, 131.5, 67.6, 44.0, 35.2, 34.8, 29.7, 27.7, 26.2, 18.4, -4.7, -4.8; LRMS (ESI$^+$): m/z 241 (8% [M+H]$^+$). S34: $\delta_H$ (400 MHz, CDCl$_3$) 5.55 (1H, ddd, J 15.9, 11.0, 3.6), 5.36 (1H, ddd, J 16.1, 10.8, 3.4), 3.42-3.37 (1H, m), 2.36-2.28 (2H, m), 2.22 (1H, app qd, J 11.2, 6.3), 2.02-1.87 (4H, m), 1.73 (1H, dd, J 14.9, 6.2), 1.67-1.45 (2H, m), 0.87 (9H, s), 0.03 (6H, s); $\delta_C$ (101 MHz, CDCl$_3$) 135.5, 132.5, 78.6, 44.9, 42.0, 34.6, 33.0, 31.3, 26.1, 18.3, -4.4, -4.5; LRMS (ESI$^+$): m/z 241 (12% [M+H]$^+$). For all further experiments trans-cyclooctcne S34 was used, where the C4-oxygen substituent occupies an equatorial position.

Tetrabutylammonium fluoride (1M solution in THF, 23.8 mL 23.8 mmol) and cesium fluoride (1.08 g, 7.14 mmol) were added to a stirring solution of silyl ether S34 (573 mg, 2.38 mmol) in MeCN (5 mL) at room temperature. The resulting mixture was wrapped in tin foil and stirred at room temperature for 36 h. After this period the reaction was cooled to 0° C., diluted with DCM (100 mL) and H$_2$O (100 mL) was added. The phases were separated, the organic phase washed with brine (2×100 mL), dried over sodium sulfate, filtered and concentrated under reduced pressure. The crude material was purified by silica gel chromatography (20% EtOAc in hexane) to yield secondary alcohol S35 as a colorless oil (289 mg, 96%) $\delta_H$ (400 MHz, CDCl$_3$) 5.60 (1H, ddd, J 16.0, 10.7, 4.2), 5.41 (1H, ddd, J 16.0, 11.1, 3.7), 3.52-3.45 (2H, m), 2.40-2.25 (3H, m), 2.03-1.90 (4H, m), 1.75-1.53 (3H, m), 1.25-1.18 (1H, m); $\delta_C$ (101 MHz, CDCl$_3$) 135.1, 132.8, 77.7, 44.6, 41.1, 34.3, 32.6, 32.1; LRMS (ESI$^+$): m/z 127 (14% [M+H]$^+$).

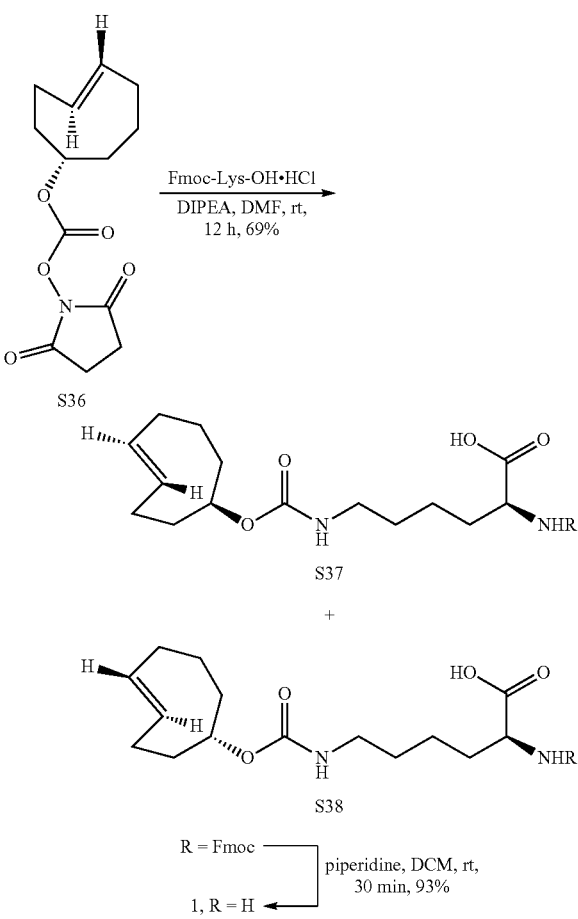

Succimidyl carbonate S36 (200 mg, 0.75 mmol) was added to a stirring solution of Fmoc-Lys-OH.HCl (303 mg, 0.75 mmol) and DIPEA (0.19 g, 1.50 mmol) in DMF (7.5 mL) at 0° C. The solution was warmed to room temperature, wrapped in tin foil and stirred for 12 h. After this period the solution was concentrated under reduced pressure and purified by silica gel chromatography (0-10% MeOH in DCM) toyicld Fmoc-TCOK-OH S37/S38 as a yellow oil that still contained DMF (350 mg, 81%). $\delta_H$ (400 MHz, CDCl$_3$) 7.75-7.69 (2H, m), 7.63-7.52 (2H, m), 7.41-7.33 (2H, m), 7.32-7.25 (2H, m), 5.82-5.34 (3H, m), 5.27 (1H, br s), 4.90-4.50 (1H, m), 4.47-4.01 (5H, m), 3.32-3.30 (lH,m), 2.39-1.08 (17H, m); $\delta_C$ (100 MHz, CDCl$_3$) 174.3, 156.3, 155.9, 143.8, 143.6, 141.1, 135.0, 134.8, 132.8, 132.6, 127.5, 126.9, 125.0, 119.8, 80.3, 66.8, 53.4, 47.0, 41.0, 40.4, 38.5, 34.1, 32.5, 32.3, 32.1, 30.8, 29.3, 22.3; ESI-MS (m/z): [M+Na]$^+$ calcd. for C$_{30}$H$_{36}$N$_2$O$_6$Na 543.2471, found 543.2466.

Piperidine (1 mL) was added to a stirring solution of Fmoc-TCOK-OH S37/S38 (0.269 g, 0.517 mmol) in DCM (4 mL). The mixture was wrapped in tin foil and stirred at room temperature for 30 min. The reaction mixture was concentrated under reduced pressure and the crude material was purified by silica gel chromatography (30-50% MeOH in DCM) to yield H-TCOK-OH 1 as an ivory-colored solid. $\delta_H$ (400 MHz, d$_4$-MeOD) 5.63-5.56 (1H, m), 5.50-5.43 (1H, m), 4.31-4.25 (1H, m), 3.60-3.53 (1H, m), 3.11-3.03 (2H, m), 2.37-2.26 (3H, m), 2.02-1.36 (13H, m); $\delta_C$ (100 MHz, d$_4$-MeOD) 174.3, 159.0, 136.3, 133.9, 81.8, 56.0, 42.4, 41.4, 39.8, 35.4, 33.7, 32.3, 32.1, 30.9, 23.6; ESI-MS (m/z): [M−H]$^-$ calcd. for C$_{15}$H$_{25}$N$_2$O$_4$ 297.1814, found 297.1811.

exo-Bicyclo[6.1.0]non-4-ene-9-ylmethanol S18 was synthesised according to a literature procedure.[5]

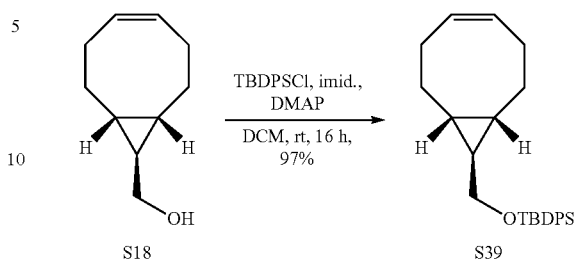

tert-Butyl(chloro)diphenylsilane (7.45 g, 27.1 mmol) was added to a stirring solution of exo-bicyclo[6.1.0]non-4-ene-9-ylmethanol S18 (2.75 g, 18.1 mmol), imidazole (2.15 g, 31.6 mmol) and DMAP (2.21 g, 18.1 mmol) in DCM (35 ml) at 0° C. The solution was warmed to room temperature and stirred for 24 h, during which a white precipitate formed. The reaction was cooled to 0° C., diluted with DCM (100 mL) and sodium bicarbonate (sat., aq., 100 mL) was added. The phases were separated and the aqueous phase was extracted with DCM (3×100 mL). The combined organics were washed with brine (200 mL), dried over sodium sulfate, filtered and concentrated under reduced pressure. The crude material was purified by silica gel chromatography (20% DCM in hexane) to yield silyl ether S39 as a colorless oil (6.85 g, 97%), $\delta_H$ (400 MHz, CDCl$_3$) 7.79-7.64 (4H, m), 7.50-7.32 (6H, m), 5.63 (2H, dm, J 11.5), 3.59 (2H,

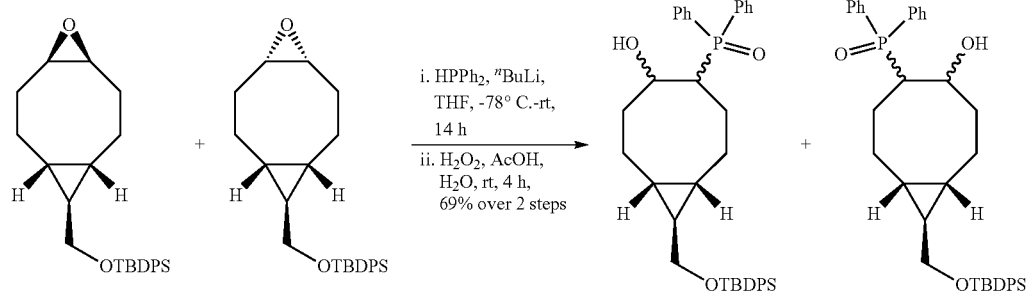

i. TBDPSCl, imid., DMAP
   DCM, rt, 16 h, 97%
ii. MeCO$_3$H, Na$_2$CO$_3$,
    AcOH, DCm, rt, 24 h, 88% i. NaH, DMF,
   rt, 2 h, 69%
ii. TBAF, THF, rt
    45 min, 96%

d, J 6.2), 2.40-2.21 (2H, m), 2.18-1.96 (4H, m), 1.45-1.33 (2H, m), 1.07 (9H, s), 0.72-0.56 (3H, m); $\delta_C$ (101 MHz, CDCl$_3$) 135.7, 134.3, 130.2, 129.5, 127.6, 67.9, 29.1, 28.6, 27.2, 26.9, 22.0, 19.3; LRMS (ESI$^+$): m/z 408 (10%, [M+NH$_4$]$^+$).

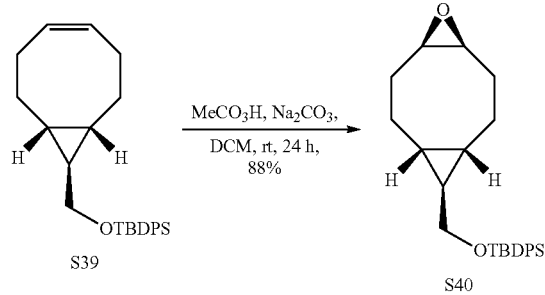

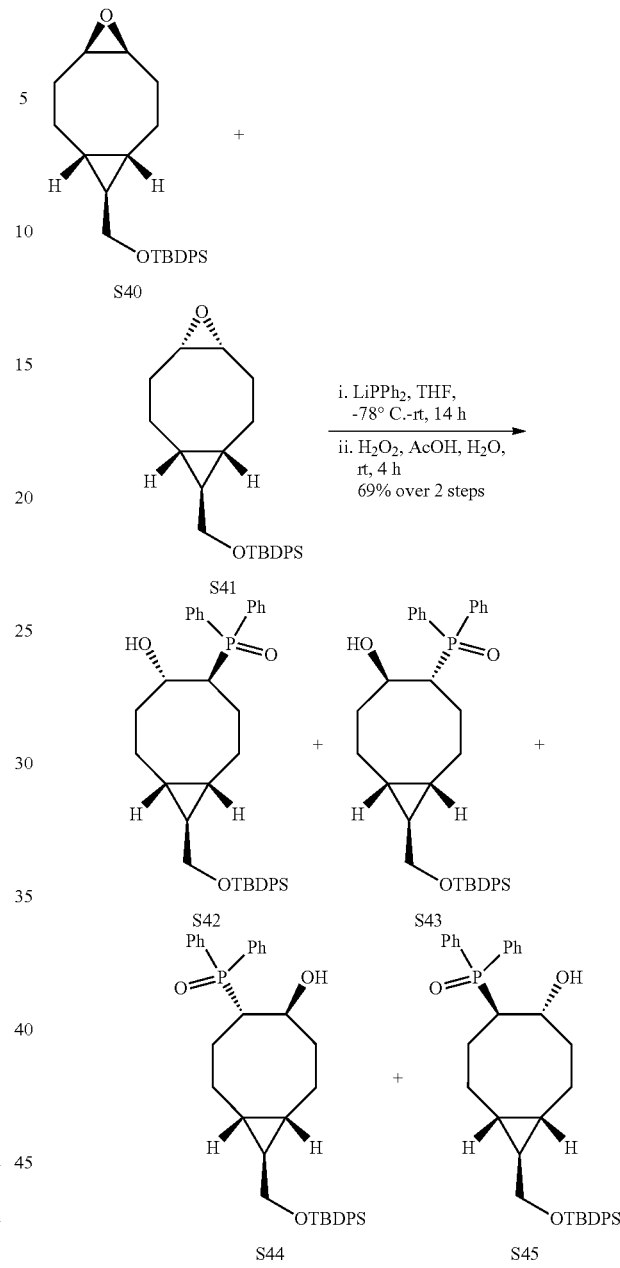

Peracetic acid (3.38 ml, 39% in acetic acid, 19.9 mmol) was added to a stirred solution of silyl ether S39 (6.49 g, 16.6 mmol) and anhydrous sodium carbonate (2.64 g, 24.9 mmol) in DCM (65 mL) at 0° C. The mixture was warmed to room temperature and stirred for 24 h. The reaction was then cooled to 0° C., diluted with DCM (100 mL) and sodium thiosulfate (sat., aq., 150 mL) was added. The mixture was stirred at room temperature for 30 min and then basified to pH 12 with NaOH (2M, aq.,). The phases were separated and the organic phase was washed with H$_2$O (200 mL), brine (200 mL), dried over sodium sulfate, filtered and concentrated under reduced pressure. The crude material was purified by silica gel chromatography (100% DCM) to yield epoxides S40 and S41 as an inseparable mixture of diastcreomers (1:1 by $^1$H NMR spectroscopy) and as a colorless oil (5.97 g, 88%). $\delta_H$ (400 MHz, CDCl$_3$) 7.72-7.63 (8H, m), 7.47-7.34 (12H, m), 3.57 (2H, d, J 5.6), 3.54 (2H, d, J 5.9), 3.03-3.10 (2H, m), 3.02-2.91 (2H, m), 2.36-2.24 (2H, m), 2.21-2.08 (2H, m), 2.06-1.85 (6H, m), 1.35-1.12 (4H, m), 1.06 (9H,s), 1.05 (9H, s), 0.92-0.80 (2H, m), 0.78-0.47 (6H, m); $\delta_C$ (101 MHz, CDCl$_3$) 135.65, 135.63, 134.2, 134.1, 129.6 (2×CH), 127.6 (2×CH), 67.4, 67.0, 56.91, 56.85, 29.7, 27.7, 26.9 (2×3CH$_3$), 26.6, 26.5, 23.31, 23.25, 21.7, 20.4, 19.2 (2×2C); LRMS (ESI$^+$): m/z 407 (9%, [M+H]$^+$).

n-Butyllithium (2.5 M in hexanes, 5.92 mL, 14.8 mmol) was added drop wise over 15 min to a stirring solution of epoxides S40/S41 (5.47 g, 13.5 mmol) and diphenylphosphine (2.57 mL, 14.80 mmol) in THF (50 mL) at −78° C. The resulting mixture was stirred at −78° C. for 1 h, warmed to room temperature and stirred for additional 14 h. The reaction mixture was diluted with THF (80 mL) and cooled to 0° C. Acetic acid (1.54 mL, 26.9 mmol) was added followed by addition of hydrogen peroxide (30% solution in H$_2$O, 3.05 mL, 26.9 mmol). The reaction mixture was warmed to room temperature and stirred for 4 h. Sodium thiosulfate (sat., aq., 100 mL) was added and the mixture stirred for 10 min. The aqueous phase was extracted with EtOAc (3×200 mL). The combined organics were washed with brine (3×200 mL), dried over sodium sulfate, filtered and concentrated under reduced pressure. The crude mixture was purified by silica gel chromatography (40-100% EtOAc in hexane) to yield phosphine oxides S42/S43/S44/S45 as a 51:18 mixture of two diasteroisomers (5.61 g, 69% over 2 steps), each of which is a 1:1 mixture of regioisomers (S42/S45 and S43/S44). Major diastereomer: δ$_H$ (400 MHz, CDCl$_3$) 7.82-7.68 (4H, m), 7.68-7.58 (4H, m), 7.52-7.32 (12H, m), 4.58-4.45 (1H, m), 4.16 (1H, d, J 5.3), 3.54 (2H, d, J 6.0), 2.47 (1H, ddd, J 12.0, 11.7, 4.3), 2.21-2.07 (1H, m), 2.05-1.85 (2H, m), 1.78-1.55 (3H, m), 1.22-1.05 (1H, m), 1.03 (9H, s), 0.91-0.75 (1H, m), 0.62-0.35 (3H, m); δ$_P$ (162 MHz, CDCl$_3$) 39.7; LRMS (ESI$^+$): m/z 609 [100%, (M+H)$^+$]. Minor diastereomer: δ$_H$ (400 MHz, CDCl$_3$) 7.87-7.77 (2H, m), 7.74-7.60 (6H, m), 7.52-7.30 (12H, m), 4.26 (1H, d, J 4.0), 3.89-3.78 (1H, m), 3.63 (1H, dd, J 10.7, 5.8), 3.54 (1H, dd, J 10.7, 6.2), 3.26-3.10 (1H, m), 2.22-2.12 (1H, m), 2.00-1.78 (3H,m), 1.70-1.62 (1H, m), 1.42-1.28 (1H, m), 1.04 (9H, s), 1.04-0.92 (2H, m), 0.79-0.65 (1H, m), 0.55-0.41 (1H, m), 0.27-0.12 (1H, m); δ$_P$ (162 MHz, CDCl$_3$) 39.6; LRMS (ESI$^+$): m/z 609 [100%, (M+H)$^+$].

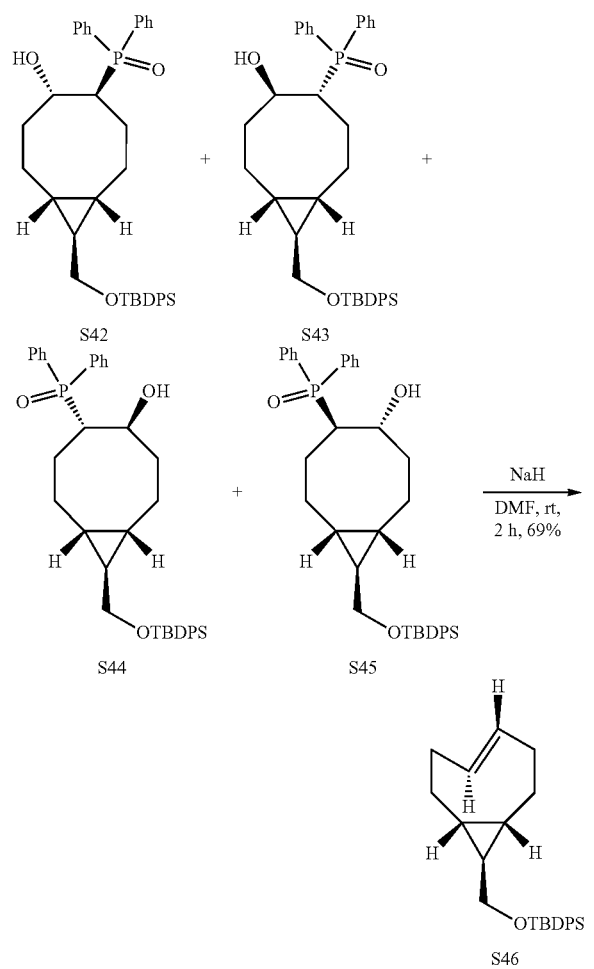

Sodium hydride (60% dispersion in mineral oil, 0.46 g, 11.5 mmol) was added to a stirring solution of hydroxyl phosphine oxides S42/S43/S44/S45 (4.68 g, 7.69 mol) in anhydrous DMF (60 mL) at 0° C. The resulting mixture was warmed to room temperature, wrapped in tin foil and stirred for 2 h. The reaction mixture was cooled to 0° C., diluted with Et$_2$O (200 mL) and H$_2$O (200 mL), the phases were separated and aqueous phase was extracted with hexane (150 mL). The combined organics were washed with brine (sat., aq., 5×250 mL), dried over sodium sulfate, filtered and concentrated under reduced pressure. The crude mixture was purified by silica gel chromatography (1-20% DCM in hexane) to yield Pww-cyclooctene S46 as a single diastereomer and with exclusive E-selectivity (2.08 g, 69%); δ$_H$ (400 MHZ, CDCl$_3$) 7.72-7.62 (4H, m), 7.46-7.34 (6H, m), 5.83 (1H, ddd, J 16.1, 9.2, 6.2), 5.11 (1H, ddd, J 16.1, 10.6, 3.3), 3.59 (2H, d, J 5.7), 2.28-2.40 (1H, m), 2.12-2.27 (3H, m), 1.80-1.95 (2H, m), 1.04 (9H, s), 0.74-0.90 (1H, m), 0.46-0.60 (1H, dm, J 14.0), 0.31-0.42 (2H, m), 0.18-0.29 (1H, m); δ$_C$ (101 MHz, CDCl$_3$) 138.6, 135.8, 134.4, 131.3, 129.6, 127.7, 68.1, 39.0, 34.1, 32.9, 28.2, 27.9, 27.0, 21.6, 20.5, 19.4.

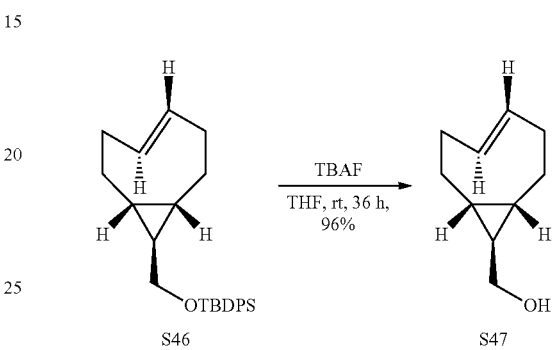

Tetrabutylammonium fluoride (1M solution in THF, 10.0 ml, 10.0 mmol) was added to a stirring solution of silyl ether S46 (0.78 g, 2 mmol) in THF (5 ml.) at room temperature, wrapped in tin foil and stirred for 45 min. After this period, the reaction mixture was concentrated under reduced pressure, diluted with DCM (100 mL) and washed with brine (100 mL). The phases were separated and the organic phase washed with brine (2×100 mL). The combined organics were dried over sodium sulfate, filtered and concentrated under reduced pressure. The crude material was purified by silica gel chromatography (20% EtOAc in hexane) to yield primary alcohol S47 as a colorless oil (0.29 g, 96%); δ$_H$ (400 MHz, d$_4$-MeOD) 5.87 (1H, ddd, J 16.5, 9.3, 6.2), 5.13 (1H, dddd, J 16.5, 10.4, 3.9, 0.8), 3.39-3.47 (2H, dd, J 6.2, 1.5), 2.34-2.44 (1H, m), 2.12-2.33 (3H, m), 1.82-1.98 (2H, m), 0.90 (1H, dtd, J 12.5, 12.5, 7.1), 0.55-0.70 (1H, m), 0.41-0.55 (1H, m), 0.27-0.41 (2H, m); δ$_C$ (101 MHz, d$_4$-MeOD) 139.3, 132.2, 67.5, 39.9, 34.8, 33.8, 29.2, 28.7, 23.0, 21.9; MS-CI (NH$_3$): m/z [M-OH] calcd. for C$_{10}$H$_{15}$, 135.1174; found 135.1173.

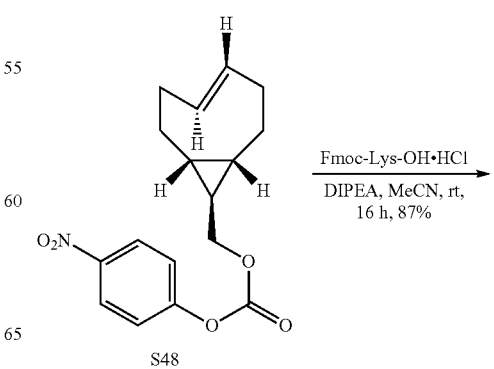

-continued

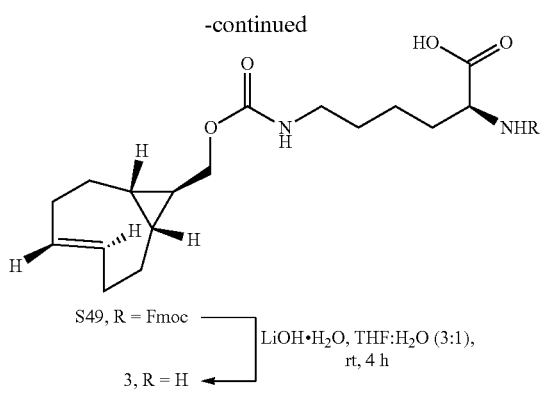

S49, R = Fmoc
3, R = H

LiOH·H₂O, THF:H₂O (3:1), rt, 4 h pNO₂-phenyl carbonate S48 (250 mg, 0.79 mmol) was added to a stirring solution of Fmoc-Lys-OH.HCl (478 mg, 1.18 mmol) and DIPEA (0.27 mL, 1.58 mmol) in DMF (3 mL) at 0° C. The solution was warmed to room temperature, wrapped in tin foil and stirred for 16 h. After this period the solution was concentrated under reduced pressure and purified by silica gel chromatography (0-5% MeOH in DCM) to yield Fmoc-exo-sTCOK. S49 as a white foam (373 mg, 87%). $\delta_H$ (400 MHz, d₆-DMSO) 13.09-12.06 (1H, br s), 7.90 (2H, d, J 7.5), 7.73 (2H, d, J 7.5), 7.66-7.56 (1H, m), 7.43 (2H, t, J 7.4), 7.34 (2H, J 7.4), 7.08 (1H, t, J 5.4), 5.84-5.72 (1H, m), 5.13-5.01 (1H, m), 4.31- 4.19 (3H, m), 3.93- 3.79 (3H, m), 3.00-2.90 (2H, m), 2.31-2.07 (4H, m), 1.91-1.78 (2H, m), 1.75-1.49 (2H, m), 1.45-1.22 (4H, m), 0.91-0.75 (1H, m), 0.62-0.45 (2H, m), 0.43-0.32 (2H, m); $\delta_C$ (101 MHz, d₆-DMSO) 173.9, 156.4, 156.1, 143.8, 140.7, 137.9, 131.0, 127.6, 127.0, 125.2, 120.1, 79.1, 67.9, 65.6, 53.8, 46.6, 38.1, 33.4, 31.9, 30.4, 29.0, 27.2, 24.3, 22.8, 21.2, 20.2; LRMS (ESI⁺): m/z 545 (100% [M−H]⁻).

Lithium hydroxide monohydrate (94 mg, 0.75 mmol) was added to a stirring solution of exo-sTCOK S49 in THF:H₂O (3:1, 8 mL). The solution was wrapped in tin foil, stirred for 4 h at room temperature and EtOAc (100 mL) and H₂O (100 mL) were added. The aqueous phase was carefully acidified to pH 4 by the addition of AcOH and extracted with EtOAc (4×100 mL). The aqueous phase was evaporated under reduced pressure and ffecze-dried to yield exo-sTCOK 3 as a white solid. For all subsequent labeling experiments using mammalian cells exo-H-benK-OH 1 was further purified by reverse -phase HPLC (0:1 H₂O:MeCN to 9:1 H₂O:MeCN gradient). $\delta_H$ (400 MHz, d₆-DMSO) 7.21-7.09 (1H, br m), 5.85-5.72 (1H, m), 5.14-5.02 (1H, m), 3.80 (2H, d, J 2.6), 3.14-3.05 (1H, m), 2.98-2.86 (2H, m), 2.31-2.08 (4H, m), 1.92-1.78 (2H, m), 1.73-1.65 (1H, m), 1.55-1.44 (1H, m), 1.41-1.25 (4H, m), 0.90-0.62 (1H, m), 0.65-0.45 (2H, m), 0.43-0.32 (2H, m); $\delta_C$ (101 MHz, d₆-DMSO) 175.5, 156.3, 137.9, 131.1, 67.8, 54.5, 38.1, 33.4, 32.1, 32.0, 29.2, 27.2, 24.7, 24.3, 22.5, 21.2, 20.2; LRMS (ESI⁺): m/z 325 (100% [M+H]⁺).

REFERENCES TO SUPPLEMENTARY EXAMPLES

1. Gautier, A. et al. Genetically encoded photocontrol of protein localization in mammalian cells. *J Am Chem Soc* 132, 4086-8 (2010).
2. Lang, K. et al. Genetically encoded norbornene directs site-specific cellular protein labelling via a rapid bioorthogonal reaction. *Nature chemistry* 4, 298-304 (2012).
3. Dommerholt, J. et al. Readily Accessible Bicyclononynes for Bioorthogonal Labeling and Three-Dimensional Imaging of Living Cells. *Angewandte Chemie-International Edition* 49, 9422-9425 (2010).
4. Yang, J., Karver, M. R., Li, W., Sahu, S. & Devaraj. N. K. Metal-catalyzed one-pot synthesis of tetrazines directly from aliphatic nitriles and hydrazine. *Angewandte Chemie* 51, 5222-5 (2012).
5. Taylor, M. T., Blackman, M. L., Dmitrenko, O. & Fox, J. M. Design and synthesis of highly reactive dienophiles for the tetrazine-trans-cyclooctene ligation. *Journal of the American Chemical Society* 133, 9646-9 (2011).
6. Royzen, M., Yap, G. P. & Fox, J. M. A photochemical synthesis of functionalized trans-cyclooctenes driven by metal complexation. *Journal of the American Chemical Society* 130,3760-1 (2008).
7. Zhang, K., Lackey, M. A., Cui, J. & Tew, G. N. Gels based on cyclic polymers. *Journal of the American Chemical Society* 133,4140-8 (2011).

REFERENCES TO MAIN TEXT (1) Devaraj, N. K.; Weissleder, R.; Hilderbrand, S. A. *Bioconjug Chem* 2008, 19, 2297.
(2) Devaraj, N. K.; Weissleder, R. *Acc Chem Res* 2011.
(3) Blackman, M. L.; Royzen, M.; Fox, J. M. *J Am Chem Soc* 2008, 130, 13518.
(4) Taylor, M. T.; Blackman, M. L; Dmitrenko, O.; Fox, J. M. *Journal of the American Chemical Society* 2011, 133, 9646.
(5) Liu, D. S.; Tangpeerachaikul, A.; Selvoraj, R.; Taylor, M. T.; Fox, J. M.; Ting, A. Y. *Journal of the American Chemical Society* 2012, 134, 792.
(6) Seitchik, J. L.; Peeler, J. C.; Taylor, M. T.; Blackman, M. L.; Rhoads, T. W.; Cooley, R. B.; Refakis, C.; Fox, J. M.; Mehl, R. A. *Journal of the American Chemical Society* 2012, 134, 2898.
(7) Lang, K.; Davis, L.; Torres-Kolbus, J.; Chou, C.; Deiters, A.; Chin, J. W. *Nature chemistry* 2012, 4, 298.
(8) Kaya, E.; Vrabel, M.; Deiml, C.; Prill, S.; Fluxa, V. S.; Carell, T. *Angewandte Chemie* 2012, 51, 4466.
(9) Plass, T.; Milles, S.; Koehler, C.; Szymanski, J.; Mueller, R.; Wiessler, M.; Schultz, C.; Lemke, E. A. *Angew Chem Int Edit* 2012, 51, 4166.
(10) Dommerholt, J.; Schmidt, S.; Temming, R.: Hendriks, L. J. A.; Rutjes, F. P. J. T.; van Hest, J. C. M.; Lefeber, D. J.; Frledl, P.; van Delft, F. L. *Angew Chem Int Edit* 2010, 49, 9422.
(11) Chen, W. X.; Wang, D. Z.; Dai, C. F.; Hamelberg, D.; Wang, B. H. *Chem Commun* 2012, 48, 1736.
(12) McKay, C. S.; Blake, J. A.; Cheng, J.; Danielson, D. C.; Pezacki, J. P. *Chem Commun* 2011, 47, 10040.
(13) McKay, C. S.; Chigrinova, M.; Blake, J. A.; Pezacki, J. P. *Organic & biomolecular chemistry* 2012.
(14) Ning, X.; Temming, R. P.; Dommerholt, J.; Guo, J.; Ania, D. B.; Debets, M. F,; Wolfert, M. A.; Boons, G. J.; van Delft, F. L. *Angewandte Chemie* 2010, 49, 3065.
(15) J.; Prescher, J. A.; Bertozzi, C. R. *Journal of the American Chemical Society* 2004, 126, 15046.
(16) Sletten, E. M.; Bertozzi, C. R. *Accounts of chemical research* 2011, 44, 666.
(17) Karver, M. R.; Weissleder, R.; Hilderbrand, S. A. *Angewandte Chemie* 2012, 51, 920.
(18) Devaraj, N. K.; Hilderbrand, S.; Upadhyay, R.; Mazitschek, R.; Weissleder, R. *Angew Chem Int Ed Engl* 2010, 49, 2869.
(19) Fekner, T.; Li, X.; Lee, M. M.; Chan, M. K. *Angew Chem Int Ed Engl* 2009, 48, 1633.

(20) Nguyen, D. P.; Garcia Alai, M. M.; Kapadnis, P. 8.; Neumann, H.; Chin, J. W. *J Am Chem Soc* 2009, 131, 14194.

(21) Nguyen, D. P.; Lusic, H.; Neumann, H.; Kapadnis, P. B.; Deiters, A.; Chin, J. W. *J Am Chem Soc* 2009, 131, 8720.

(22) Nguyen, D. P.; Elliott, T.; Holt, M.; Muir, T. W.; Chin, J. W. *J Am Chem Soc* 2011, 133, 11418.

(23) Neumann, H.; Peak-Chew, S. Y.; Chin, J. W. *Nat Chem Biol* 2008, 4, 232.

(24) Polycarpo, C. R.; Herring, S.; Berube, A.; Wood, J. L.; Soli, D.; Ambrogelly, A. *FEBS Lett* 2006, 580, 6695.

(25) Li, X.; Fekner, T.; Ottesen, J. J.; Chan, M. K. *Angew Chem Int Ed Engl* 2009, 48, 9184.

(26) Wang, Y. S.; Fang, X.; Wallace, A. L.; Wu, B.; Liu, W. R. *Journal of the American Chemical Society* 2012, 134, 2950.

(27) Mukai, T.; Kobayashi, T.; Hino, N.; Yanagisawa, T.; Sakamoto, K.; Yokoyama, S. *Biochem Biophys Res Commun* 2008, 371, 818.

(28) Hancock, S. M.; Uprety, R.; Deiters, A.; Chin, J. W. *J Am Chem Soc* 2010, 132, 14819.

(29) Greiss, S.; Chin, J. W. *J Am Chem Soc* 2011.

(30) Lin, S. X.; Zhang, Z. R.; Xu, H.; Li, L.; Chen, S.; Li, J.; Hao, Z. Y.; Chen, P. R. *Journal of the American Chemical Society* 2011, 133, 20581.

(31) Gautier, A.; Nguyen. D. P.; Lusic, H.; An, W.; Deiters, A.; Chin, J. W. *J Am Chem Soc* 2010, 132, 4086.

(32) Virdee, S.; Kapadnis, P. B.; Elliott, T.; Lang, K.; Madreak, J.; Nguyen, D. P.; Riechmann, L.; Chin, J. W. *Journal of the American Chemical Society* 2011, 133, 10708.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method of producing a polypeptide comprising a bicyclo[6.1.0]non-4-yn-9-ylmethanol (BCN) group in a cell, said method comprising genetically incorporating an amino acid comprising a BCN group into a polypeptide in a cell, wherein said amino acid comprising a BCN group is a BCN lysine, and wherein producing the polypeptide comprises (i) providing a nucleic acid encoding the polypeptide which nucleic acid comprises an orthogonal codon encoding the amino acid having a BCN group; and (ii) translating said nucleic acid in the cell in the presence of an orthogonal tRNA synthetase/tRNA pair capable of recognizing said orthogonal codon and incorporating said amino acid having a BCN group into the polypeptide chain, wherein the tRNA synthetase consists of SEQ ID NO: 1 with the three following mutations: Y271M, 274G, and C313A; and wherein said BCN group is in the exo form, wherein said BCN lysine has the structure:

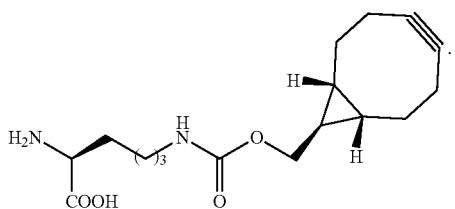

2. The method according to claim 1, wherein said orthogonal codon comprises an amber codon (TAG) and said tRNA is mbtRNA$_{CUA}$.

3. The method according to claim 1, wherein said amino acid having a BCN group is incorporated at a position corresponding to a lysine residue in the wild type polypeptide.

4. The method according to claim 1, wherein the method produces a polypeptide comprising a single BCN group.

5. The method according to claim 1, further comprising:
(iii) contacting the translated polypeptide with a tetrazine compound, and incubating to allow joining of the tetrazine compound to the BCN group by an inverse electron demand Diels-Alder cycloaddition reaction.

6. The method according to claim 5, wherein the tetrazine compound has the chemical formula of a)

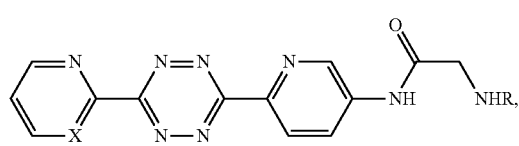

Formula VI wherein:
(i) X=CH, R=BOC (Formula VI-1);
(ii) X=N, R=BOC (Formula VI-2);
(iii) X=CH, R=TAMRA-X (Formula VI-3);
(iv) X=N, R=TAMRA-X (Formula VI-4);
(v) X=CH, R=Bodipy TMR-X (Formula VI-5); or
(vi) X=CH, R=TAMRA (Formula VI-6), b)

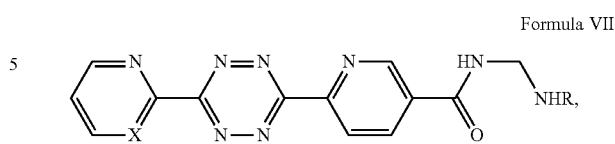

Formula VII wherein:
(i) R=BOC (Formula VII-1):
(ii) R=TAMRA-X (Formula VII-2); or
(iii) R=Bodipy-FL (Formula VII-3), c)

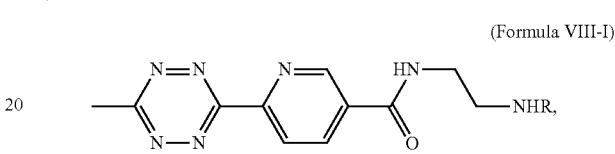

(Formula VIII-I)

wherein R = BOC or d)

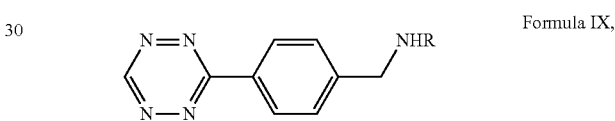

Formula IX, wherein:
(i) R=BOC (Formula IX-I); or
(ii) R=CFDA (Formula IX-2).

7. The method according to claim 6, wherein the tetrazine compound has the chemical formula selected from the group consisting of Formula VI-1, Formula VI-2, Formula VII-1 and Formula VIII-1, and wherein the pseudo first order rate constant for the reaction is at least 80 $M^{-1}S^{-1}$.

8. The method according to claim 5, wherein said reaction of step (iii) is allowed to proceed for 10 minutes or less.

9. The method according to claim 5, wherein said reaction of step (iii) is allowed to proceed for 1 minute or less.

10. The method according to claim 5, wherein said reaction of step (iii) is allowed to proceed for 30 seconds or less.

11. The method according to claim 6, wherein said tetrazine compound has the chemical formula selected from the group consisting of Formula VI-3, Formula VI-4, Formula VI-5, Formula VI-6, Formula VII-2, Formula VII-3, and Formula IX-2.

12. The method according to claim 5, wherein said tetrazine compound is further joined to a fluorophore.

13. The method according to claim 12, wherein said fluorophore comprises fluorescein, tetramethyl rhodamine (TAMRA) or boron-dipyrromethene (BODIPY).

* * * * *

SEQUENCE LISTING

<160> NUMBER OF SEQ ID NOS: 18

<210> SEQ ID NO 1
<211> LENGTH: 419
<212> TYPE: PRT
<213> ORGANISM: Methanosarcina barkeri

<400> SEQUENCE: 1

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Ala Pro Lys Val Lys Lys Ala Met Pro Lys Ser Val Ser
                100                 105                 110

Arg Ala Pro Lys Pro Leu Glu Asn Pro Val Ser Ala Lys Ala Ser Thr
            115                 120                 125

Asp Thr Ser Arg Ser Val Pro Ser Pro Ala Lys Ser Thr Pro Asn Ser
        130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
                180                 185                 190

Lys Asn Asp Phe Gln Arg Leu Tyr Thr Asn Asp Arg Glu Asp Tyr Leu
            195                 200                 205

Gly Lys Leu Glu Arg Asp Ile Thr Lys Phe Phe Val Asp Arg Asp Phe
        210                 215                 220
```

```
Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
            245                 250                 255

Asp Lys Asn Leu Cys Leu Arg Pro Met Leu Ala Pro Thr Leu Tyr Asn
        260                 265                 270

Tyr Leu Arg Lys Leu Asp Arg Ile Leu Pro Asp Pro Ile Lys Ile Phe
    275                 280                 285

Glu Val Gly Pro Cys Tyr Arg Lys Glu Ser Asp Gly Lys Glu His Leu
290                 295                 300

Glu Glu Phe Thr Met Val Asn Phe Cys Gln Met Gly Ser Gly Cys Thr
305                 310                 315                 320

Arg Glu Asn Leu Glu Ser Leu Ile Lys Glu Phe Leu Asp Tyr Leu Glu
            325                 330                 335

Ile Asp Phe Glu Ile Val Gly Asp Ser Cys Met Val Tyr Gly Asp Thr
        340                 345                 350

Leu Asp Ile Met His Gly Asp Leu Glu Leu Ser Ser Ala Val Val Gly
    355                 360                 365

Pro Val Pro Leu Asp Arg Glu Trp Gly Ile Asp Lys Pro Trp Ile Gly
370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
            405                 410                 415

Thr Asn Leu

<210> SEQ ID NO 2
<211> LENGTH: 419
<212> TYPE: PRT
<213> ORGANISM: Methanosarcina barkeri

<400> SEQUENCE: 2

Met Asp Lys Lys Pro Leu Asp Val Leu Ile Ser Ala Thr Gly Leu Trp
1               5                   10                  15

Met Ser Arg Thr Gly Thr Leu His Lys Ile Lys His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
            85                  90                  95

Val Val Ser Ala Pro Lys Val Lys Ala Met Pro Lys Ser Val Ser
        100                 105                 110

Arg Ala Pro Lys Pro Leu Glu Asn Ser Val Ser Ala Lys Ala Ser Thr
    115                 120                 125

Asn Thr Ser Arg Ser Val Pro Ser Pro Ala Lys Ser Thr Pro Asn Ser
130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
            165                 170                 175
```

Met Ala Lys Pro Phe Arg Glu Leu Glu Pro Glu Leu Val Thr Arg Arg
              180                 185                 190

Lys Asn Asp Phe Gln Arg Leu Tyr Thr Asn Asp Arg Glu Asp Tyr Leu
            195                 200                 205

Gly Lys Leu Glu Arg Asp Ile Thr Lys Phe Phe Val Asp Arg Gly Phe
        210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
              245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
              325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
              405                 410                 415

Thr Asn Leu

<210> SEQ ID NO 3
<211> LENGTH: 419
<212> TYPE: PRT
<213> ORGANISM: Methanosarcina barkeri

<400> SEQUENCE: 3

Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Val Ser
              20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
              85                  90                  95

Val Val Ser Ala Pro Lys Val Lys Lys Ala Met Pro Lys Ser Val Ser
            100                 105                 110

Arg Ala Pro Lys Pro Leu Glu Asn Pro Val Ser Ala Lys Ala Ser Thr
        115                 120                 125

```
Asp Thr Ser Arg Ser Val Pro Ser Pro Ala Lys Ser Thr Pro Asn Ser
    130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Asp Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Asp Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ser Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Pro Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 4
<211> LENGTH: 454
<212> TYPE: PRT
<213> ORGANISM: Methanosarcina mazeii

<400> SEQUENCE: 4

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80
```

```
Lys Phe Leu Thr Lys Ala Asn Glu Asp Gln Thr Ser Val Lys Val Lys
                 85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 5
<211> LENGTH: 443
<212> TYPE: PRT
<213> ORGANISM: Methanosarcina acetivorans

<400> SEQUENCE: 5
```

```
Met Asp Lys Lys Pro Leu Asp Thr Leu Ile Ser Ala Thr Gly Leu Trp
1               5                   10                  15

Met Ser Arg Thr Gly Met Ile His Lys Ile Lys His Glu Val Ser
            20                  25                  30

Arg Ser Lys Ile Tyr Ile Glu Met Ala Cys Gly Glu Arg Leu Val Val
            35                  40                  45

Asn Asn Ser Arg Ser Ser Arg Thr Ala Arg Ala Leu Arg His His Lys
        50                  55                  60

Tyr Arg Lys Thr Cys Arg His Cys Arg Val Ser Asp Glu Asp Ile Asn
65                  70                  75                  80

Asn Phe Leu Thr Lys Thr Ser Glu Glu Lys Thr Thr Val Lys Val Lys
                85                  90                  95

Val Val Ser Ala Pro Arg Val Arg Lys Ala Met Pro Lys Ser Val Ala
                100                 105                 110

Arg Ala Pro Lys Pro Leu Glu Ala Thr Ala Gln Val Pro Leu Ser Gly
            115                 120                 125

Ser Lys Pro Ala Pro Ala Thr Pro Val Ser Ala Pro Ala Gln Ala Pro
        130                 135                 140

Ala Pro Ser Thr Gly Ser Ala Ser Ala Thr Ser Ala Ser Ala Gln Arg
145                 150                 155                 160

Met Ala Asn Ser Ala Ala Ala Pro Ala Ala Pro Val Pro Thr Ser Ala
                165                 170                 175

Pro Ala Leu Thr Lys Gly Gln Leu Asp Arg Leu Glu Gly Leu Leu Ser
            180                 185                 190

Pro Lys Asp Glu Ile Ser Leu Asp Ser Glu Lys Pro Phe Arg Glu Leu
            195                 200                 205

Glu Ser Glu Leu Leu Ser Arg Arg Lys Lys Asp Leu Lys Arg Ile Tyr
210                 215                 220

Ala Glu Glu Arg Glu Asn Tyr Leu Gly Lys Leu Glu Arg Glu Ile Thr
225                 230                 235                 240

Lys Phe Phe Val Asp Arg Gly Phe Leu Glu Ile Lys Ser Pro Ile Leu
                245                 250                 255

Ile Pro Ala Glu Tyr Val Glu Arg Met Gly Ile Asn Ser Asp Thr Glu
                260                 265                 270

Leu Ser Lys Gln Val Phe Arg Ile Asp Lys Asn Phe Cys Leu Arg Pro
        275                 280                 285

Met Leu Ala Pro Asn Leu Tyr Asn Tyr Leu Arg Lys Leu Asp Arg Ala
        290                 295                 300

Leu Pro Asp Pro Ile Lys Ile Phe Glu Ile Gly Pro Cys Tyr Arg Lys
305                 310                 315                 320

Glu Ser Asp Gly Lys Glu His Leu Glu Glu Phe Thr Met Leu Asn Phe
                325                 330                 335

Cys Gln Met Gly Ser Gly Cys Thr Arg Glu Asn Leu Glu Ala Ile Ile
            340                 345                 350

Thr Glu Phe Leu Asn His Leu Gly Ile Asp Phe Glu Ile Ile Gly Asp
            355                 360                 365

Ser Cys Met Val Tyr Gly Asn Thr Leu Asp Val Met His Asp Asp Leu
        370                 375                 380

Glu Leu Ser Ser Ala Val Val Gly Pro Val Pro Leu Asp Arg Glu Trp
385                 390                 395                 400

Gly Ile Asp Lys Pro Trp Ile Gly Ala Gly Phe Gly Leu Glu Arg Leu
                405                 410                 415
```

```
Leu Lys Val Met His Gly Phe Lys Asn Ile Lys Arg Ala Ala Arg Ser
            420                 425                 430

Glu Ser Tyr Tyr Asn Gly Ile Ser Thr Asn Leu
        435                 440

<210> SEQ ID NO 6
<211> LENGTH: 478
<212> TYPE: PRT
<213> ORGANISM: Methanosarcina thermophila

<400> SEQUENCE: 6

Met Asp Lys Lys Pro Leu Asn Thr Leu Ile Ser Ala Thr Gly Leu Trp
1               5                   10                  15

Met Ser Arg Thr Gly Lys Leu His Lys Ile Arg His His Glu Val Ser
            20                  25                  30

Lys Arg Lys Ile Tyr Ile Glu Met Glu Cys Gly Glu Arg Leu Val Val
        35                  40                  45

Asn Asn Ser Arg Ser Cys Arg Ala Ala Arg Ala Leu Arg His His Lys
    50                  55                  60

Tyr Arg Lys Ile Cys Lys His Cys Arg Val Ser Asp Glu Asp Leu Asn
65                  70                  75                  80

Lys Phe Leu Thr Arg Thr Asn Glu Asp Lys Ser Asn Ala Lys Val Thr
                85                  90                  95

Val Val Ser Ala Pro Lys Ile Arg Lys Val Met Pro Lys Ser Val Ala
            100                 105                 110

Arg Thr Pro Lys Pro Leu Glu Asn Thr Ala Pro Val Gln Thr Leu Pro
        115                 120                 125

Ser Glu Ser Gln Pro Ala Pro Thr Thr Pro Ile Ser Ala Ser Thr Thr
    130                 135                 140

Ala Pro Ala Ser Thr Ser Thr Thr Ala Pro Ala Pro Ala Ser Thr Thr
145                 150                 155                 160

Ala Pro Ala Pro Ala Ser Thr Thr Ala Pro Ala Ser Ala Ser Thr Thr
                165                 170                 175

Ile Ser Thr Ser Ala Met Pro Ala Ser Thr Ser Ala Gln Gly Thr Thr
            180                 185                 190

Lys Phe Asn Tyr Ile Ser Gly Gly Phe Pro Arg Pro Ile Pro Val Gln
        195                 200                 205

Ala Ser Ala Pro Ala Leu Thr Lys Ser Gln Ile Asp Arg Leu Gln Gly
    210                 215                 220

Leu Leu Ser Pro Lys Asp Glu Ile Ser Leu Asp Ser Gly Thr Pro Phe
225                 230                 235                 240

Arg Lys Leu Glu Ser Glu Leu Leu Ser Arg Arg Lys Asp Leu Lys
                245                 250                 255

Gln Ile Tyr Ala Glu Glu Arg Glu His Tyr Leu Gly Lys Leu Glu Arg
            260                 265                 270

Glu Ile Thr Lys Phe Phe Val Asp Arg Gly Phe Leu Glu Ile Lys Ser
        275                 280                 285

Pro Ile Leu Ile Pro Met Glu Tyr Ile Glu Arg Met Gly Ile Asp Asn
    290                 295                 300

Asp Lys Glu Leu Ser Lys Gln Ile Phe Arg Val Asp Asn Asn Phe Cys
305                 310                 315                 320

Leu Arg Pro Met Leu Ala Pro Asn Leu Tyr Asn Tyr Leu Arg Lys Leu
                325                 330                 335

Asn Arg Ala Leu Pro Asp Pro Ile Lys Ile Phe Glu Ile Gly Pro Cys
            340                 345                 350
```

-continued

Tyr Arg Lys Glu Ser Asp Gly Lys Glu His Leu Glu Glu Phe Thr Met
        355                 360                 365

Leu Asn Phe Cys Gln Met Gly Ser Gly Cys Thr Arg Glu Asn Leu Glu
    370                 375                 380

Ala Ile Ile Lys Asp Phe Leu Asp Tyr Leu Gly Ile Asp Phe Glu Ile
385                 390                 395                 400

Val Gly Asp Ser Cys Met Val Tyr Gly Asp Thr Leu Asp Val Met His
                405                 410                 415

Gly Asp Leu Glu Leu Ser Ser Ala Val Val Gly Pro Val Pro Met Asp
            420                 425                 430

Arg Asp Trp Gly Ile Asn Lys Pro Trp Ile Gly Ala Gly Phe Gly Leu
        435                 440                 445

Glu Arg Leu Leu Lys Val Met His Asn Phe Lys Asn Ile Lys Arg Ala
450                 455                 460

Ser Arg Ser Glu Ser Tyr Tyr Asn Gly Ile Ser Thr Asn Leu
465                 470                 475

<210> SEQ ID NO 7
<211> LENGTH: 416
<212> TYPE: PRT
<213> ORGANISM: Methanococcoides burtonii

<400> SEQUENCE: 7

Met Glu Lys Gln Leu Leu Asp Val Leu Val Glu Leu Asn Gly Val Trp
1               5                   10                  15

Leu Ser Arg Ser Gly Leu Leu His Gly Ile Arg Asn Phe Glu Ile Thr
            20                  25                  30

Thr Lys His Ile His Ile Glu Thr Asp Cys Gly Ala Arg Phe Thr Val
        35                  40                  45

Arg Asn Ser Arg Ser Arg Ser Ala Arg Ser Leu Arg His Asn Lys
50                  55                  60

Tyr Arg Lys Pro Cys Lys Arg Cys Arg Pro Ala Asp Glu Gln Ile Asp
65                  70                  75                  80

Arg Phe Val Lys Lys Thr Phe Lys Glu Lys Arg Gln Thr Val Ser Val
                85                  90                  95

Phe Ser Ser Pro Lys Lys His Val Pro Lys Pro Lys Val Ala Val
            100                 105                 110

Ile Lys Ser Phe Ser Ile Ser Thr Pro Ser Pro Lys Glu Ala Ser Val
        115                 120                 125

Ser Asn Ser Ile Pro Thr Pro Ser Ile Ser Val Val Lys Asp Glu Val
    130                 135                 140

Lys Val Pro Glu Val Lys Tyr Thr Pro Ser Gln Ile Glu Arg Leu Lys
145                 150                 155                 160

Thr Leu Met Ser Pro Asp Asp Lys Ile Pro Ile Gln Asp Glu Leu Pro
                165                 170                 175

Glu Phe Lys Val Leu Glu Lys Glu Leu Ile Gln Arg Arg Asp
            180                 185                 190

Leu Lys Lys Met Tyr Glu Glu Asp Arg Glu Asp Arg Leu Gly Lys Leu
        195                 200                 205

Glu Arg Asp Ile Thr Glu Phe Phe Val Asp Arg Gly Phe Leu Glu Ile
    210                 215                 220

Lys Ser Pro Ile Met Ile Pro Phe Glu Tyr Ile Glu Arg Met Gly Ile
225                 230                 235                 240

Asp Lys Asp Asp His Leu Asn Lys Gln Ile Phe Arg Val Asp Glu Ser

```
                   245                 250                 255
Met Cys Leu Arg Pro Met Leu Ala Pro Cys Leu Tyr Asn Tyr Leu Arg
                260                 265                 270

Lys Leu Asp Lys Val Leu Pro Asp Pro Ile Arg Ile Phe Glu Ile Gly
            275                 280                 285

Pro Cys Tyr Arg Lys Glu Ser Asp Gly Ser Ser His Leu Glu Glu Phe
290                 295                 300

Thr Met Val Asn Phe Cys Gln Met Gly Ser Gly Cys Thr Arg Glu Asn
305                 310                 315                 320

Met Glu Ala Leu Ile Asp Glu Phe Leu Glu His Leu Gly Ile Glu Tyr
                325                 330                 335

Glu Ile Glu Ala Asp Asn Cys Met Val Tyr Gly Asp Thr Ile Asp Ile
                340                 345                 350

Met His Gly Asp Leu Glu Leu Ser Ser Ala Val Val Gly Pro Ile Pro
                355                 360                 365

Leu Asp Arg Glu Trp Gly Val Asn Lys Pro Trp Met Gly Ala Gly Phe
            370                 375                 380

Gly Leu Glu Arg Leu Leu Lys Val Arg His Asn Tyr Thr Asn Ile Arg
385                 390                 395                 400

Arg Ala Ser Arg Ser Glu Leu Tyr Tyr Asn Gly Ile Asn Thr Asn Leu
                405                 410                 415

<210> SEQ ID NO 8
<211> LENGTH: 279
<212> TYPE: PRT
<213> ORGANISM: Desulfitobacterium hafniense

<400> SEQUENCE: 8

Met Ser Ser Phe Trp Thr Lys Val Gln Tyr Gln Arg Leu Lys Glu Leu
1               5                   10                  15

Asn Ala Ser Gly Glu Gln Leu Glu Met Gly Phe Ser Asp Ala Leu Ser
            20                  25                  30

Arg Asp Arg Ala Phe Gln Gly Ile Glu His Gln Leu Met Ser Gln Gly
        35                  40                  45

Lys Arg His Leu Glu Gln Leu Arg Thr Val Lys His Arg Pro Ala Leu
    50                  55                  60

Leu Glu Leu Glu Glu Gly Leu Ala Lys Ala Leu His Gln Gln Gly Phe
65                  70                  75                  80

Val Gln Val Val Thr Pro Thr Ile Ile Thr Lys Ser Ala Leu Ala Lys
                85                  90                  95

Met Thr Ile Gly Glu Asp His Pro Leu Phe Ser Gln Val Phe Trp Leu
            100                 105                 110

Asp Gly Lys Lys Cys Leu Arg Pro Met Leu Ala Pro Asn Leu Tyr Thr
        115                 120                 125

Leu Trp Arg Glu Leu Glu Arg Leu Trp Asp Lys Pro Ile Arg Ile Phe
    130                 135                 140

Glu Ile Gly Thr Cys Tyr Arg Lys Glu Ser Gln Gly Ala Gln His Leu
145                 150                 155                 160

Asn Glu Phe Thr Met Leu Asn Leu Thr Glu Leu Gly Thr Pro Leu Glu
                165                 170                 175

Glu Arg His Gln Arg Leu Glu Asp Met Ala Arg Trp Val Leu Glu Ala
            180                 185                 190

Ala Gly Ile Arg Glu Phe Glu Leu Val Thr Glu Ser Ser Val Val Tyr
        195                 200                 205
```

Gly Asp Thr Val Asp Val Met Lys Gly Asp Leu Glu Leu Ala Ser Gly
    210                 215                 220

Ala Met Gly Pro His Phe Leu Asp Glu Lys Trp Glu Ile Val Asp Pro
225                 230                 235                 240

Trp Val Gly Leu Gly Phe Gly Leu Glu Arg Leu Leu Met Ile Arg Glu
                245                 250                 255

Gly Thr Gln His Val Gln Ser Met Ala Arg Ser Leu Ser Tyr Leu Asp
            260                 265                 270

Gly Val Arg Leu Asn Ile Asn
            275

<210> SEQ ID NO 9
<211> LENGTH: 312
<212> TYPE: PRT
<213> ORGANISM: Desulfitobacterium hafniense

<400> SEQUENCE: 9

Met Asp Arg Ile Asp His Thr Asp Ser Lys Phe Val Gln Ala Gly Glu
1               5                   10                  15

Thr Pro Val Leu Pro Ala Thr Phe Met Phe Leu Thr Arg Arg Asp Pro
            20                  25                  30

Pro Leu Ser Ser Phe Trp Thr Lys Val Gln Tyr Gln Arg Leu Lys Glu
        35                  40                  45

Leu Asn Ala Ser Gly Glu Gln Leu Glu Met Gly Phe Ser Asp Ala Leu
    50                  55                  60

Ser Arg Asp Arg Ala Phe Gln Gly Ile Glu His Gln Leu Met Ser Gln
65                  70                  75                  80

Gly Lys Arg His Leu Glu Gln Leu Arg Thr Val Lys His Arg Pro Ala
                85                  90                  95

Leu Leu Glu Leu Glu Gly Leu Ala Lys Ala Leu His Gln Gln Gly
            100                 105                 110

Phe Val Gln Val Val Thr Pro Thr Ile Ile Thr Lys Ser Ala Leu Ala
        115                 120                 125

Lys Met Thr Ile Gly Glu Asp His Pro Leu Phe Ser Gln Val Phe Trp
130                 135                 140

Leu Asp Gly Lys Lys Cys Leu Arg Pro Met Leu Ala Pro Asn Leu Tyr
145                 150                 155                 160

Thr Leu Trp Arg Glu Leu Glu Arg Leu Trp Asp Lys Pro Ile Arg Ile
                165                 170                 175

Phe Glu Ile Gly Thr Cys Tyr Arg Lys Glu Ser Gln Gly Ala Gln His
            180                 185                 190

Leu Asn Glu Phe Thr Met Leu Asn Leu Thr Glu Leu Gly Thr Pro Leu
        195                 200                 205

Glu Glu Arg His Gln Arg Leu Glu Asp Met Ala Arg Trp Val Leu Glu
    210                 215                 220

Ala Ala Gly Ile Arg Glu Phe Glu Leu Val Thr Glu Ser Ser Val Val
225                 230                 235                 240

Tyr Gly Asp Thr Val Asp Val Met Lys Gly Asp Leu Glu Leu Ala Ser
                245                 250                 255

Gly Ala Met Gly Pro His Phe Leu Asp Glu Lys Trp Glu Ile Val Asp
            260                 265                 270

Pro Trp Val Gly Leu Gly Phe Gly Leu Glu Arg Leu Leu Met Ile Arg
        275                 280                 285

Glu Gly Thr Gln His Val Gln Ser Met Ala Arg Ser Leu Ser Tyr Leu
    290                 295                 300

Asp Gly Val Arg Leu Asn Ile Asn
305                 310

<210> SEQ ID NO 10
<211> LENGTH: 288
<212> TYPE: PRT
<213> ORGANISM: Desulfitobacterium hafniense

<400> SEQUENCE: 10

Met Phe Leu Thr Arg Arg Asp Pro Pro Leu Ser Ser Phe Trp Thr Lys
1               5                   10                  15

Val Gln Tyr Gln Arg Leu Lys Glu Leu Asn Ala Ser Gly Glu Gln Leu
            20                  25                  30

Glu Met Gly Phe Ser Asp Ala Leu Ser Arg Asp Arg Ala Phe Gln Gly
        35                  40                  45

Ile Glu His Gln Leu Met Ser Gln Gly Lys Arg His Leu Glu Gln Leu
    50                  55                  60

Arg Thr Val Lys His Arg Pro Ala Leu Leu Glu Leu Glu Glu Lys Leu
65                  70                  75                  80

Ala Lys Ala Leu His Gln Gln Gly Phe Val Gln Val Val Thr Pro Thr
                85                  90                  95

Ile Ile Thr Lys Ser Ala Leu Ala Lys Met Thr Ile Gly Glu Asp His
            100                 105                 110

Pro Leu Phe Ser Gln Val Phe Trp Leu Asp Gly Lys Lys Cys Leu Arg
        115                 120                 125

Pro Met Leu Ala Pro Asn Leu Tyr Thr Leu Trp Arg Glu Leu Glu Arg
    130                 135                 140

Leu Trp Asp Lys Pro Ile Arg Ile Phe Glu Ile Gly Thr Cys Tyr Arg
145                 150                 155                 160

Lys Glu Ser Gln Gly Ala Gln His Leu Asn Glu Phe Thr Met Leu Asn
                165                 170                 175

Leu Thr Glu Leu Gly Thr Pro Leu Glu Glu Arg His Gln Arg Leu Glu
            180                 185                 190

Asp Met Ala Arg Trp Val Leu Glu Ala Ala Gly Ile Arg Glu Phe Glu
        195                 200                 205

Leu Val Thr Glu Ser Ser Val Val Tyr Gly Asp Thr Val Asp Val Met
    210                 215                 220

Lys Gly Asp Leu Glu Leu Ala Ser Gly Ala Met Gly Pro His Phe Leu
225                 230                 235                 240

Asp Glu Lys Trp Glu Ile Phe Asp Pro Trp Val Gly Leu Gly Phe Gly
                245                 250                 255

Leu Glu Arg Leu Leu Met Ile Arg Glu Gly Thr Gln His Val Gln Ser
            260                 265                 270

Met Ala Arg Ser Leu Ser Tyr Leu Asp Gly Val Arg Leu Asn Ile Asn
        275                 280                 285

<210> SEQ ID NO 11
<211> LENGTH: 277
<212> TYPE: PRT
<213> ORGANISM: Desulfotomaculum acetoxidans

<400> SEQUENCE: 11

Met Ser Phe Leu Trp Thr Val Ser Gln Gln Lys Arg Leu Ser Glu Leu
1               5                   10                  15

Asn Ala Ser Glu Glu Glu Lys Asn Met Ser Phe Ser Ser Thr Ser Asp
            20                  25                  30

Arg Glu Ala Ala Tyr Lys Arg Val Glu Met Arg Leu Ile Asn Glu Ser
            35                  40                  45

Lys Gln Arg Leu Asn Lys Leu Arg His Glu Thr Arg Pro Ala Ile Cys
    50                  55                  60

Ala Leu Glu Asn Arg Leu Ala Ala Leu Arg Gly Ala Gly Phe Val
65                  70                  75                  80

Gln Val Ala Thr Pro Val Ile Leu Ser Lys Leu Leu Gly Lys Met
                85                  90                  95

Thr Ile Thr Asp Glu His Ala Leu Phe Ser Gln Val Phe Trp Ile Glu
                    100                 105                 110

Glu Asn Lys Cys Leu Arg Pro Met Leu Ala Pro Asn Leu Tyr Tyr Ile
            115                 120                 125

Leu Lys Asp Leu Leu Arg Leu Trp Glu Lys Pro Val Arg Ile Phe Glu
    130                 135                 140

Ile Gly Ser Cys Phe Arg Lys Glu Ser Gln Gly Ser Asn His Leu Asn
145                 150                 155                 160

Glu Phe Thr Met Leu Asn Leu Val Glu Trp Gly Leu Pro Glu Glu Gln
                165                 170                 175

Arg Gln Lys Arg Ile Ser Glu Leu Ala Lys Leu Val Met Asp Glu Thr
            180                 185                 190

Gly Ile Asp Glu Tyr His Leu Glu His Ala Glu Ser Val Val Tyr Gly
    195                 200                 205

Glu Thr Val Asp Val Met His Arg Asp Ile Glu Leu Gly Ser Gly Ala
210                 215                 220

Leu Gly Pro His Phe Leu Asp Gly Arg Trp Gly Val Val Gly Pro Trp
225                 230                 235                 240

Val Gly Ile Gly Phe Gly Leu Glu Arg Leu Leu Met Val Glu Gln Gly
                245                 250                 255

Gly Gln Asn Val Arg Ser Met Gly Lys Ser Leu Thr Tyr Leu Asp Gly
            260                 265                 270

Val Arg Leu Asn Ile
        275

<210> SEQ ID NO 12
<211> LENGTH: 419
<212> TYPE: PRT
<213> ORGANISM: Methanosarcina barkeri

<400> SEQUENCE: 12

Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Ala Pro Lys Val Lys Lys Ala Met Pro Lys Ser Val Ser
                100                 105                 110

Arg Ala Pro Lys Pro Leu Glu Asn Pro Val Ser Ala Lys Ala Ser Thr

```
            115                 120                 125
Asp Thr Ser Arg Ser Val Pro Ser Pro Ala Lys Ser Thr Pro Asn Ser
    130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Asp Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Asp Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ser Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Pro Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 13
<211> LENGTH: 419
<212> TYPE: PRT
<213> ORGANISM: Artificial Sequence
<220> FEATURE:
<223> OTHER INFORMATION: MbPylS

<400> SEQUENCE: 13

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60
```

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
            85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
            115                 120                 125

Asn Thr Ser Arg Ser Val Pro Ser Pro Ala Lys Ser Thr Pro Asn Ser
130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
            165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
            195                 200                 205

Gly Lys Leu Glu Arg Asp Ile Thr Lys Phe Phe Val Asp Arg Gly Phe
210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
            245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Gly Pro Ile Lys Ile Phe
            275                 280                 285

Glu Val Gly Pro Cys Tyr Arg Lys Glu Ser Asp Gly Lys Glu His Leu
            290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
            325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
            355                 360                 365

Pro Val Ser Leu Asp Arg Glu Trp Gly Ile Asp Lys Pro Trp Ile Gly
            370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
            405                 410                 415

Thr Asn Leu

<210> SEQ ID NO 14
<211> LENGTH: 419
<212> TYPE: PRT
<213> ORGANISM: Artificial Sequence
<220> FEATURE:
<223> OTHER INFORMATION: Mb_AckRS

<400> SEQUENCE: 14

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Gly Glu Asp Ile Asn
65                  70                  75                  80

Asn Phe Leu Thr Arg Ser Thr Glu Ser Lys Asn Ser Val Lys Val Arg
            85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
            115                 120                 125

Asn Thr Ser Arg Ser Val Pro Ser Pro Ala Lys Ser Thr Pro Asn Ser
        130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
            165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
            245                 250                 255

Asp Lys Asn Leu Cys Leu Arg Pro Met Val Ala Pro Thr Ile Phe Asn
        260                 265                 270

Tyr Ala Arg Lys Leu Asp Arg Ile Leu Pro Gly Pro Ile Lys Ile Phe
275                 280                 285

Glu Val Gly Pro Cys Tyr Arg Lys Glu Ser Asp Gly Lys Glu His Leu
    290                 295                 300

Glu Glu Phe Thr Met Val Asn Phe Phe Gln Met Gly Ser Gly Cys Thr
305                 310                 315                 320

Arg Glu Asn Leu Glu Ala Leu Ile Lys Glu Phe Leu Asp Tyr Leu Glu
            325                 330                 335

Ile Asp Phe Glu Ile Val Gly Asp Ser Cys Met Val Tyr Gly Asp Thr
        340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
            405                 410                 415

Thr Asn Leu
```

<210> SEQ ID NO 15
<211> LENGTH: 419
<212> TYPE: PRT
<213> ORGANISM: Artificial Sequence
<220> FEATURE:
<223> OTHER INFORMATION: MbPCKRS

<400> SEQUENCE: 15

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
                100                 105                 110

Arg Ala Pro Lys Pro Leu Glu Asn Ser Val Ser Ala Lys Ala Ser Thr
            115                 120                 125

Asn Thr Ser Arg Ser Val Pro Ser Pro Ala Lys Ser Thr Pro Asn Ser
        130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
                180                 185                 190

Lys Asn Asp Phe Gln Arg Leu Tyr Thr Asn Asp Arg Glu Asp Tyr Leu
            195                 200                 205

Gly Lys Leu Glu Arg Asp Ile Thr Lys Phe Phe Val Asp Arg Gly Phe
        210                 215                 220

Leu Glu Ile Lys Ser Pro Ile Leu Ile Pro Ala Glu Tyr Val Glu Arg
225                 230                 235                 240

Phe Gly Ile Asn Asn Asp Thr Glu Leu Ser Lys Gln Ile Phe Arg Val
                245                 250                 255

Asp Lys Asn Leu Cys Leu Arg Pro Met Leu Ser Pro Thr Leu Cys Asn
                260                 265                 270

Tyr Met Arg Lys Leu Asp Arg Ile Leu Pro Gly Pro Ile Lys Ile Phe
            275                 280                 285

Glu Val Gly Pro Cys Tyr Arg Lys Glu Ser Asp Gly Lys Glu His Leu
        290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365
```

```
Pro Val Ser Leu Asp Arg Glu Trp Gly Ile Asp Lys Pro Trp Ile Gly
        370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 16
<211> LENGTH: 454
<212> TYPE: PRT
<213> ORGANISM: Artificial Sequence
<220> FEATURE:
<223> OTHER INFORMATION: MmPylS

<400> SEQUENCE: 16

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
                100                 105                 110

Ala Arg Ala Pro Lys Pro Leu Glu Asn Thr Glu Ala Ala Gln Ala Gln
            115                 120                 125

Pro Ser Gly Ser Lys Phe Ser Pro Ala Ile Pro Val Ser Thr Gln Glu
        130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300
```

```
Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
            325                 330                 335

Glu His Leu Glu Glu Phe Thr Met Leu Asn Phe Cys Gln Met Gly Ser
        340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
            405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 17
<211> LENGTH: 454
<212> TYPE: PRT
<213> ORGANISM: Artificial Sequence
<220> FEATURE:
<223> OTHER INFORMATION: Mm_AcKRS

<400> SEQUENCE: 17

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205
```

```
Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Val Ala Pro Asn
    290                 295                 300

Ile Phe Asn Tyr Ala Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Phe Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 18
<211> LENGTH: 454
<212> TYPE: PRT
<213> ORGANISM: Artificial Sequence
<220> FEATURE:
<223> OTHER INFORMATION: MmPCKRS

<400> SEQUENCE: 18

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
                100                 105                 110
```

```
Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
        130                 135             140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
        210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
                260                 265                 270

Ile Glu Arg Phe Gly Ile Asp Asn Asp Thr Glu Leu Ser Lys Gln Ile
            275                 280                 285

Phe Arg Val Asp Lys Asn Phe Cys Leu Arg Pro Met Leu Ser Pro Asn
        290                 295                 300

Leu Cys Asn Tyr Met Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
        370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
                420                 425                 430

Asp Phe Lys Asn Ile Lys Arg Ala Ala Arg Ser Glu Ser Tyr Tyr Asn
        435                 440                 445

Gly Ile Ser Thr Asn Leu
        450
```